US010028938B2

(12) United States Patent
Von Itzstein et al.

(10) Patent No.: US 10,028,938 B2
(45) Date of Patent: Jul. 24, 2018

(54) ANTIVIRAL AGENTS AND USES THEREOF

(71) Applicant: Griffith University, Nathan (AU)

(72) Inventors: Mark Von Itzstein, Palm Beach (AU); Ibrahim El-Deeb, Biggera Waters (AU); Larissa Dirr, Main Beach (AU); Patrice Guillon, Southport (AU); Moritz Winger, Broadbeach (AU)

(73) Assignee: Griffith University, Nathan (AU)

( * ) Notice: Subject to any disclaimer, the term of this patent is extended or adjusted under 35 U.S.C. 154(b) by 0 days.

(21) Appl. No.: 15/508,055

(22) PCT Filed: Sep. 7, 2015

(86) PCT No.: PCT/AU2015/050526
§ 371 (c)(1),
(2) Date: Mar. 1, 2017

(87) PCT Pub. No.: WO2016/033660
PCT Pub. Date: Mar. 10, 2016

(65) Prior Publication Data
US 2017/0290809 A1    Oct. 12, 2017

(30) Foreign Application Priority Data
Sep. 5, 2014 (NL) ...................... 2013420

(51) Int. Cl.
*A61K 31/4192* (2006.01)
*A61K 31/351* (2006.01)
*A61K 31/36* (2006.01)
*A61K 31/4025* (2006.01)
*A61K 31/403* (2006.01)
*A61K 31/41* (2006.01)

(52) U.S. Cl.
CPC ........ *A61K 31/4192* (2013.01); *A61K 31/351* (2013.01); *A61K 31/36* (2013.01); *A61K 31/403* (2013.01); *A61K 31/4025* (2013.01); *A61K 31/41* (2013.01); *A61K 2300/00* (2013.01)

(58) Field of Classification Search
CPC ................................ A61K 31/4192
USPC ........................................ 549/365
See application file for complete search history.

(56) References Cited

FOREIGN PATENT DOCUMENTS

WO    WO 2002/076971    3/2002
WO    WO 2011/006237    1/2011

OTHER PUBLICATIONS

King, Med. Chem., Principle and Practice (1994), pp. 206-208.*
Alymova et al., "Efficacy of Novel Hemagglutinin-Neuraminidase Inhibitors BCX 2798 and BCX 2855 against Human Parainfluenza Viruses In Vitro and In Vivo," *Antimicrobial Agents and Chemotherapy*, 48(5): 1495-1502, May 2004.
Feng et al., "Recent Advances in Neuraminidase Inhibitor Development as Anti-Influenza Drugs," *Chem Med Chem*, vol. 7, pp. 1527-1536, Jul. 16, 2012.
International Search Report and Written Opinion issued for International Application No. PCT/AU2015/050526.
International Search Report and Written Opinion issued for Netherlands Application No. 2013420 dated Apr. 20, 2015.
Li et al., "Syntheses of triazole-modified zanamivir analogues via click chemistry and anti-AIV activities," *Bioorganic & Medicinal Chemistry Letters*, 16(19): 5009-5013, 2006.
Lu et al., "Synthesis of C-4 and C-7 triazole analogs of zanamivir as multivalent sialic acid containing scaffolds," *Carbohydrate Research*, 342(12-13): 1636-1650, 2007.
Shidmoossavee et al., "Chemical Insight into the Emergence of Influenza Virus Strains that are Resistant to Relenza," *Journal of the American Chemical Society*, 135(36): 13254-13257, 2013.
Tindal et al., "Synthesis and evaluation of 4-O-alkylated 2-deoxy-2,3-didehydro-N-acetylneuraminic acid derivatives as inhibitors of human parainfluenza virus type-3 sialidase activity," *Bioorganic & Medicinal Chemistry Letters*, vol. 17, pp. 1655-1658, Jan. 8, 2007.
Ye et al., "Synthesis of C-4 modified zanamivir analogs as neuraminidase inhibitors and their anti-AIV activities," *European Journal of Medicinal Chemistry*, vol. 54, pp. 764-770, Jun. 29, 2012.

* cited by examiner

*Primary Examiner* — Taofiq A Solola
(74) *Attorney, Agent, or Firm* — Klarquist Sparkman, LLP

(57) ABSTRACT

The present invention relates to compounds which are found to exhibit an antiviral effect. The compounds are modulators of the activity of the viral haemagglutinin and/or neuraminidase enzymes.

15 Claims, 9 Drawing Sheets

ANTIVIRAL AGENTS AND USES THEREOF

CROSS REFERENCE TO RELATED APPLICATIONS

This is the U.S. National Stage of International Application No. PCT/AU2015/050526, filed Sep. 7, 2015, which was published in English under PCT Article 21(2), which in turn claims the benefit of Netherlands Application No. 2013420, filed Sep. 5, 2014, the contents of both of which are incorporated herein by reference.

FIELD OF THE INVENTION

The invention relates to the field of medical treatment. More particularly, this invention relates to novel antiviral agents and their use in treating a disease or condition caused by a viral infection.

BACKGROUND TO THE INVENTION

Any reference to background art herein is not to be construed as an admission that such art constitutes common general knowledge in Australia or elsewhere.

Viruses are responsible for a wide range of mammalian disease which represents a great cost to society. The effects of viral infection can range from common flu symptoms to serious respiratory problems and can result in death, particularly amongst the young, elderly and immunocompromised members of the community.

Viruses of the family Orthomyxoviridae, including influenza virus types A, B and C, and the family Paramyxoviridae are the pathogenic organisms responsible for a significant number of human infections annually.

Taking the family Paramyxoviridae as one example, human parainfluenza viruses types 1 to 3 (hPIV-1, 2 and 3) are the leading cause of upper and lower respiratory tract disease in infants and young children and also impact the elderly and immunocompromised. Significantly, it is estimated that in the United States alone up to five million lower respiratory tract infections occur each year in children under 5 years old, and hPIV has been isolated in approximately one third of these cases. There are currently neither vaccines nor specific antiviral therapy to prevent or treat hPIV infections respectively, despite continuing efforts. Some of the more recent approaches have focussed on an entry blockade and the triggering of premature virus fusion by a small molecule.

An initial interaction of the parainfluenza virus with the host cell is through its surface glycoprotein, haemagglutinin-neuraminidase (HN) and involves recognition of N-acetyl-neuraminic acid-containing glycoconjugates. The parainfluenza virus HN is a multifunctional protein that encompasses the functions of receptor binding (for cell adhesion) and receptor destruction (facilitating virus release), not only within the one protein, but apparently in a single binding site. In addition, the HN is involved in activation of the viral surface fusion (F) protein necessary to initiate infection of the target host cell. Inhibition of haemagglutinin and/or neuraminidase enzymes may therefore provide a target for antivirals.

SUMMARY OF INVENTION

According to a first aspect of the invention, there is provided a compound of formula (I), or a pharmaceutically acceptable salt thereof:

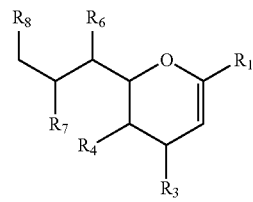

Formula (I)

wherein, $R_1$ is selected from the group consisting of COOH, or a salt thereof, $C(O)NR_9R_{10}$, $C(O)OR_{11}$ wherein $R_9$, $R_{10}$ and $R_{11}$ are independently selected from the group consisting of hydrogen and optionally substituted $C_1$-$C_6$ alkyl;

$R_3$ is selected from the group consisting of N-linked triazole substituted at one or both ring carbon atoms, optionally substituted N-linked tetrazole, optionally substituted N-linked indole, optionally substituted N-linked isoindole, and optionally substituted N-linked benzotriazole;

$R_4$ is $NHC(O)R_{17}$ wherein $R_{17}$ is selected from the group consisting of $C_1$-$C_6$ alkyl, $C_1$-$C_6$ haloalkyl and $C_3$-$C_6$ cycloalkyl;

$R_6$, $R_7$ and $R_8$ are independently selected from the group consisting of OH, $NH_2$, $C_1$-$C_6$ alkyl, $NR_{18}R_{18}'$, $C_1$-$C_6$ alkoxy, $-OC(O)R_{18}$, $-NH(C=O)R_{18}$, and $S(O)_nR_{18}$, wherein n=0-2 and each $R_{18}$ and $R_{18}'$ are independently hydrogen or optionally substituted $C_1$-$C_6$ alkyl.

In one embodiment of the first aspect, the compound of formula (I) is a compound of formula (II):

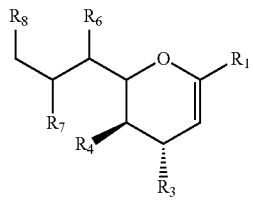

Formula (II)

wherein, $R_1$, $R_3$, $R_4$, $R_6$, $R_7$ and $R_8$ are as described above.

According to a second aspect of the invention there is provided a pharmaceutical composition comprising an effective amount of a compound of the first aspect, or a pharmaceutically acceptable salt thereof, and a pharmaceutically acceptable carrier, diluent and/or excipient.

Suitably, the pharmaceutical composition is for the treatment or prophylaxis of a disease, disorder or condition caused by viral infection.

A third aspect of the invention resides in a method of treating a disease, disorder or condition caused by viral infection in a patient including the step of administering an effective amount of a compound of the first aspect, or a pharmaceutically effective salt thereof, or the pharmaceutical composition of the second aspect to the patient.

A fourth aspect of the invention provides for a compound of the first aspect, or a pharmaceutically effective salt thereof, or the pharmaceutical composition of the second aspect for use in the treatment of a disease, disorder or condition caused by viral infection in a patient.

A fifth aspect of the invention provides for use of a compound of the first aspect, or a pharmaceutically effective salt thereof, in the manufacture of a medicament for the treatment of a disease, disorder or condition caused by viral infection.

In one embodiment of the third, fourth or fifth aspects, the disease, disorder or condition is influenza.

The influenza may be influenza A, B or C or parainfluenza.

In one embodiment, the parainfluenza is an hPIV-1, -2 or -3 virus.

Preferably, the patient is a domestic or livestock animal or a human.

A sixth aspect of the invention provides for a method of modulating the activity of a viral haemagglutinin and/or neuraminidase enzyme including the step of contacting the enzyme with a compound of the first aspect.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

Figure 7:
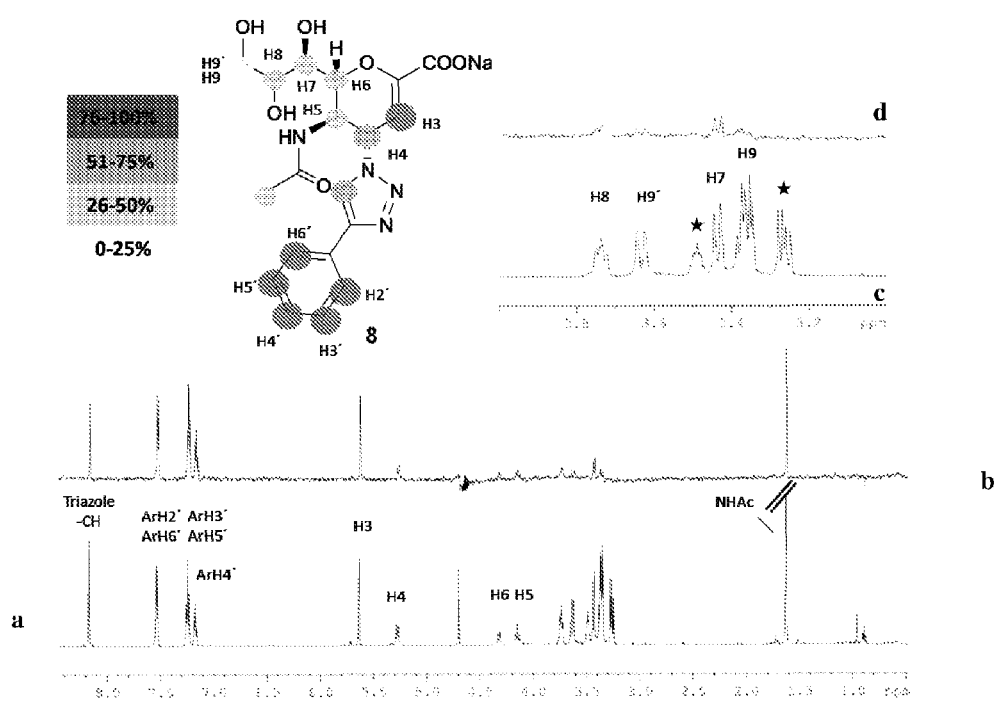
Figure 8:
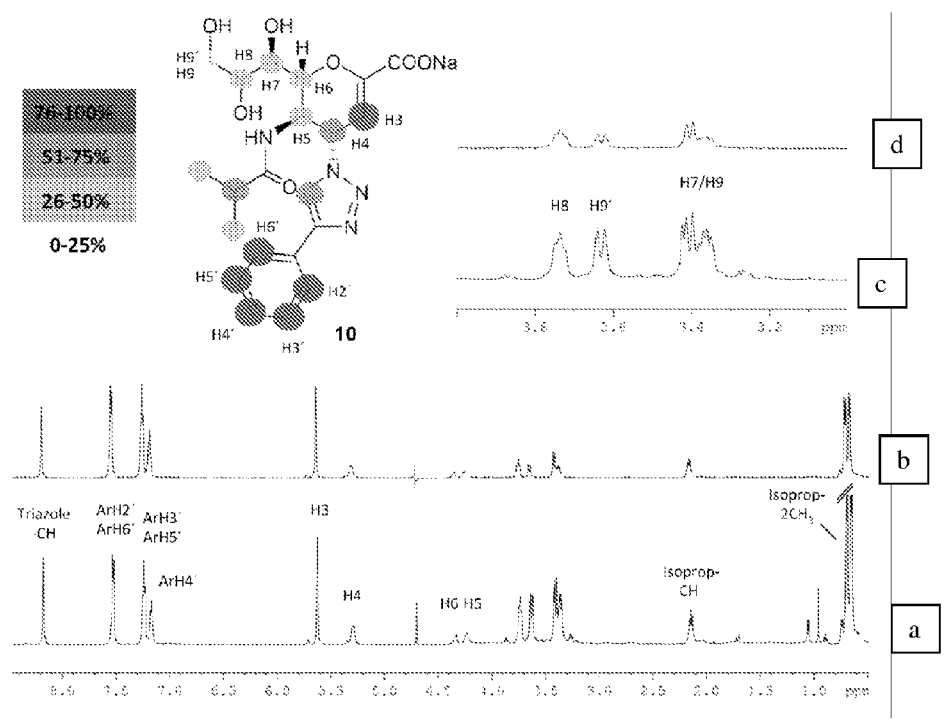
Figure 9:
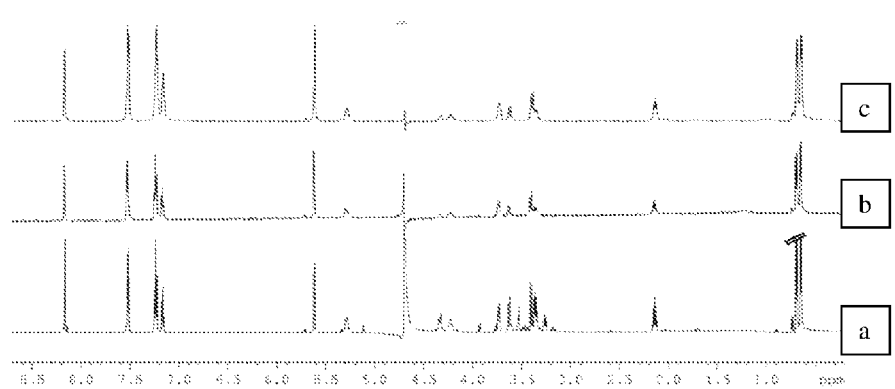
Figure 10:
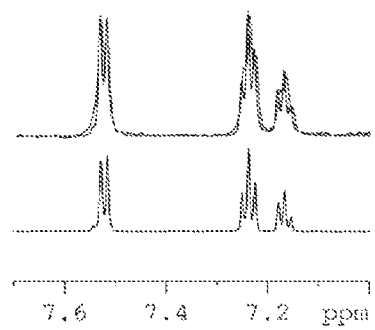
Figure 11:
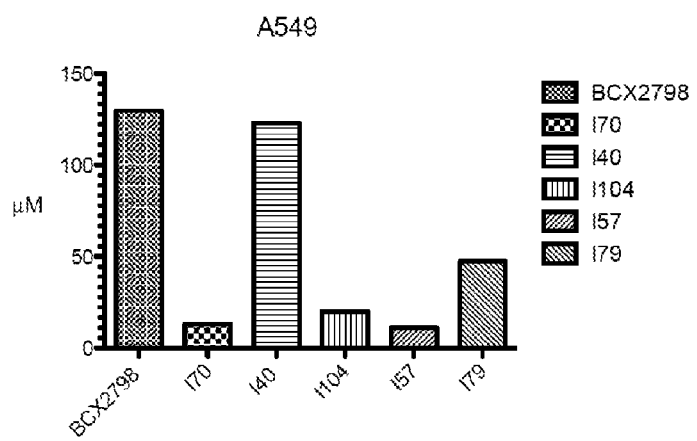
Figure 12:
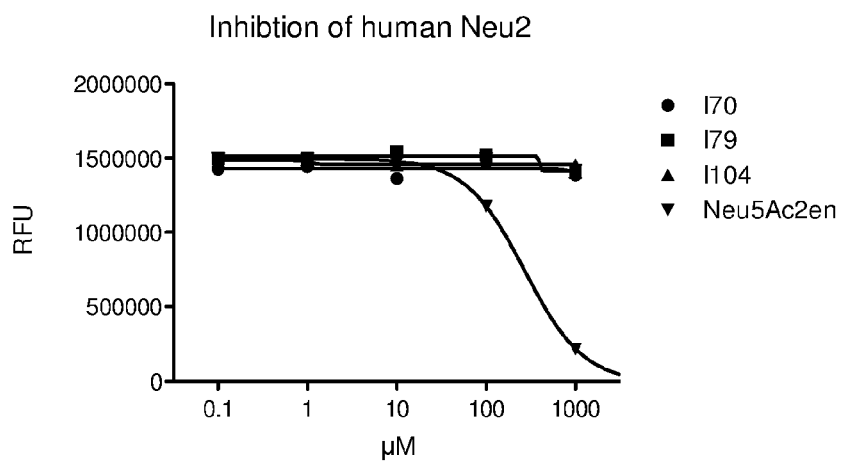

Virus growth $IC_{50}$ values of compounds 6 (□) and 10 (▲) were determined by an in situ ELISA technique against both human cell lines (A549 and NHBE) and a monkey kidney cell line (LLC-MK2). $IC_{50}$ values of 54.6±3.8 μM and 2.1±0.6 μM (LLC-MK2); 130.6±13.0 M and 10.3±0.3 μM (A549); 79.3±1.0 μM and 13.9±0.7 μM (NHBE) were determined for 6 and 10 respectively. These values were determined from at least 2 independent experiments performed in triplicate and error bars correspond to the calculated standard deviation;

FIG. 7 $^1$H and STD NMR spectra of 8 in complex with hPIV-3 HN. (a) $^1$H NMR spectrum of 8 and (b) STD NMR spectrum of 8 in the presence of 20 μM hPIV-3 HN at a protein-ligand ratio of 1:100 (2 mM 8). (c) $^1$H NMR spectrum of the H7, H8, H9 and H9' region. Signals from residual glycerol are marked as ★. (d) STD NMR spectrum of the H7, H8, H9 and H9' region. (e) The proposed binding epitope of 8;

FIG. 8 is a $^1$H and STD NMR spectra and epitope map of 10 in complex with hPIV-3 HN. (a) $^1$H NMR spectrum of 10. (b) STD NMR spectrum of 10 in the presence of 20 μM hPIV-3 HN at a protein-ligand ratio of 1:100 (2 mM of 10). (c) $^1$H NMR spectrum of the H7, H8, H9 and H9' region. (d) STD NMR spectrum of the H7, H8, H9 and H9' region. (e) proposed binding epitope map of inhibitor 10;

FIG. 9 is an STD NMR spectra comparison of 10 in complex with intact hPIV-3 virus or recombinant HN. (a) $^1$H NMR spectrum of 10 in the presence of hPIV-3 HN, (b) STD NMR spectrum of 10 in the presence of intact hPIV-3 virus and (c) STD NMR spectrum of 10 in the presence of hPIV-3 HN;

FIG. 10 is a superimposition of the phenyl protons from 10 in complex with intact virus or recombinant HN. (a) $^1$H NMR spectrum of 10 and (b) Superimpositions of STD NMR spectra from 10 in the presence of hPIV-3 virus (black) or recombinant hPIV-3 HN (red);

FIG. 11 is a graphical representation of the results of cell cytotoxicity tests against A549 cells; and FIG. 12 indicates the results of Neu2 inhibition assays for select fluorinated and non-fluorinated compounds.

DETAILED DESCRIPTION

The present invention is predicated, at least in part, on the finding that certain neuraminic acid derivatives display useful efficacy in the treatment of diseases caused by viral infection. Particularly, the compounds of the invention are useful in the inhibition of parainfluenza haemagglutinin and/or neuraminidase enzymes.

Definitions

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

As used herein, "effective amount" refers to the administration of an amount of the relevant active agent sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

The terms "substituted" and "optionally substituted" in each incidence of its use herein, and in the absence of an explicit listing for any particular moiety, refers to substitution of the relevant moiety, for example an alkyl chain or ring structure, with one or more groups selected from $C_1$-$C_6$ alkyl, $C_1$-$C_6$ haloalkyl, $C_1$-$C_6$ alkoxy, CN, OH, oxo, $NH_2$, Cl, F, Br, I, aryl and heterocyclyl which latter two may themselves be optionally substituted. When the term is used before the recitation of a number of functional groups then it is intended to apply to all of the listed functionalities unless otherwise apparent. For example, "optionally substituted amino, heterocyclic, aryl" means all of the amino, heterocyclic and aryl groups may be optionally substituted.

The term "alkyl" refers to a straight-chain or branched alkyl substituent containing from, for example, 1 to about 12 carbon atoms, preferably 1 to about 8 carbon atoms, more preferably 1 to about 6 carbon atoms, even more preferably from 1 to about 4 carbon atoms, still yet more preferably from 1 to 2 carbon atoms. Examples of such substituents include methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents, for example the carbon atoms of an alkoxy substituent branching off the main carbon chain.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hickel's Rule. C-6 aryl is preferred.

The terms "heterocyclic" and "heterocyclyl" as used herein specifically in relation to certain 'R' groups refers to a non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic may be selected from pyrazole, imidazole, indole, isoindole, triazole, benzotriazole, tetrazole, pyrimidine, pyridine, pyrazine, diazine, triazine, tetrazine, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "protected OH" or "protected hydroxy" refers to a hydroxyl group which is protected with a common protecting group such as an acyl group, ether group or ester group including $C_1$-$C_3$ acyl, $C_1$-$C_4$ alkyl groups to form the ether or aryl, such as benzyl, forming the ether or $C_1$-$C_4$ ester.

The term "N-linked" as used herein with reference to compounds of the first aspect including compounds of formula (I) and (II), for example "N-linked triazole" or "N-linked heterocycle", refers to the moiety attached at the C-4 position of the neuraminic acid core ($R_3$ in formula (I) and (II)) and limits that attachment to involving a direct attachment between ring carbon and nitrogen atom. Preferably, it refers to the $R_3$ moiety being linked to the neuraminic acid core via a nitrogen atom which itself forms part of the appropriate heterocycle, such as one of the nitrogens of a triazole ring, tetrazole, indole etc. For the "dilfuoro" compounds of formula (III) and (IIIa) the term N-linked refers to the $R_3$ moiety either being linked to the core via an intermediate nitrogen atom or, in the case of a heterocyclic moiety, it may be via a nitrogen atom which forms part of the heterocycle itself, such as one of the nitrogens of a triazole ring Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, alkyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for a disease or condition caused by viral infection. However, it will be understood that the aforementioned terms do not imply that symptoms are necessarily present.

According to a first aspect of the invention, there is provided a compound of formula (I), or a pharmaceutically acceptable salt thereof:

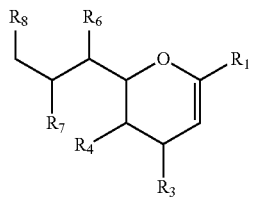

Formula (I)

wherein, $R_1$ is selected from the group consisting of COOH, or a salt thereof, $C(O)NR_9R_{10}$, $C(O)OR_{11}$ wherein $R_9$, $R_{10}$ and $R_{11}$ are independently selected from the group consisting of hydrogen and optionally substituted $C_1$-$C_6$ alkyl;

$R_3$ is selected from the group consisting of N-linked triazole substituted at one or both ring carbon atoms, optionally substituted N-linked tetrazole, optionally substituted N-linked indole, optionally substituted N-linked isoindole, and optionally substituted N-linked benzotriazole;

$R_4$ is $NHC(O)R_{17}$ wherein $R_{17}$ is selected from the group consisting of $C_1$-$C_6$ alkyl, $C_1$-$C_6$ haloalkyl and $C_3$-$C_6$ cycloalkyl; and $R_6$, $R_7$ and $R_8$ are independently selected from the group consisting of OH, $NH_2$, $C_1$-$C_6$ alkyl, $NR_{18}R_{18}'$, $C_1$-$C_6$ alkoxy, $-OC(O)R_{18}$, $-NH(C=O)R_{18}$, and $S(O)_nR_{18}$, wherein n=0-2 and each $R_{18}$ and $R_{18}'$ are independently hydrogen or optionally substituted $C_1$-$C_6$ alkyl.

In one embodiment of the first aspect, the compound of formula (I) is a compound of formula (II):

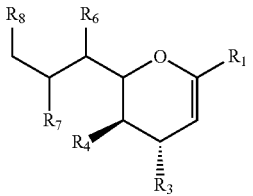

Formula (II)

wherein, $R_1$, $R_3$, $R_4$, $R_6$, $R_7$ and $R_8$ are as previously described.

Preferably, the triazole is a 1,2,3-triazole ring connected directly to the neuraminic acid ring carbon at the N-1 position.

In one embodiment wherein the tetrazole is substituted, it is substituted at the ring carbon only.

In one embodiment of the compound of formula (I) or (II) $R_1$ is COOH, or a salt thereof, or $C(O)OR_{11}$ wherein $R_{11}$ is selected from methyl, ethyl and propyl.

In certain specific embodiments $R_1$ is selected from the group consisting of COOH, COONa and C(O)OMe.

In one embodiment of the compound of formula (I) or (II) $R_3$ is selected from the group consisting of:

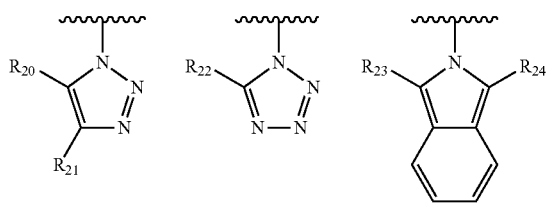

wherein, $R_{20}$ and $R_{21}$ are independently selected from the group consisting of hydrogen, hydroxyl, cyano, halo, $C_1$-$C_6$ alkyl, $C_1$-$C_6$ haloalkyl, $C_1$-$C_6$ alkylether, optionally substituted pyridyl and optionally substituted phenyl, and wherein at least one of $R_{20}$ and $R_{21}$ is not hydrogen;

$R_{22}$ is selected from the group consisting of hydrogen, $C_1$-$C_6$ alkyl and optionally substituted phenyl; and $R_{23}$ and $R_{24}$ are independently selected from the group consisting of hydrogen, hydroxyl, cyano, halo, $C_1$-$C_6$ alkyl and $C_1$-$C_6$ haloalkyl.

In certain preferred embodiments, $R_{20}$ and $R_{21}$ are selected from $C_1$-$C_6$ alkyl, $C_1$-$C_6$ hydroxyalkyl, $C_1$-$C_6$ alkoxy, optionally substituted pyridyl and optionally substituted phenyl.

In one embodiment, wherein when $R_{20}$, $R_{21}$ or $R_{22}$ are optionally substituted pyridyl or optionally substituted phenyl, as appropriate, then the substitution may be with a moiety selected from the group consisting of $C_1$-$C_6$ alkyl, $C_1$-$C_6$ haloalkyl, $C_1$-$C_6$ alkylhydroxy, $C_1$-$C_6$ alkoxy, halo, $-C(O)OMe$ and $-CH_2OCH_3$.

In certain embodiments, $R_3$ may be selected from the group consisting of:

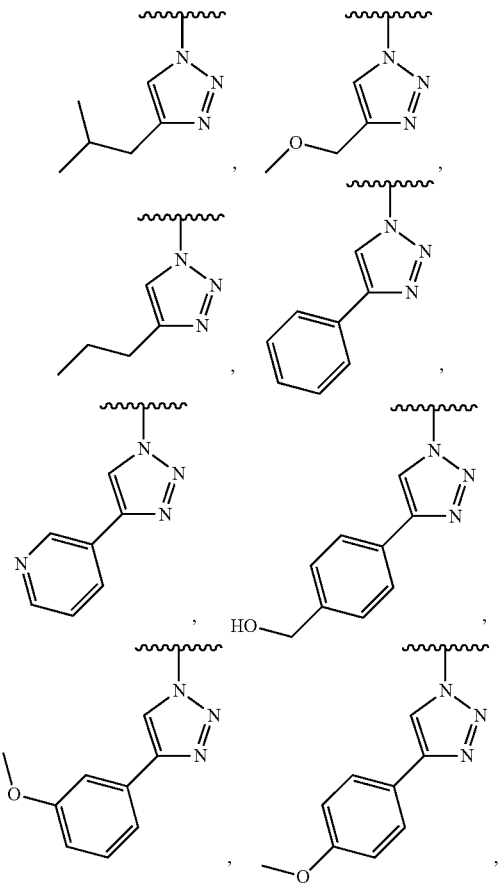

-continued

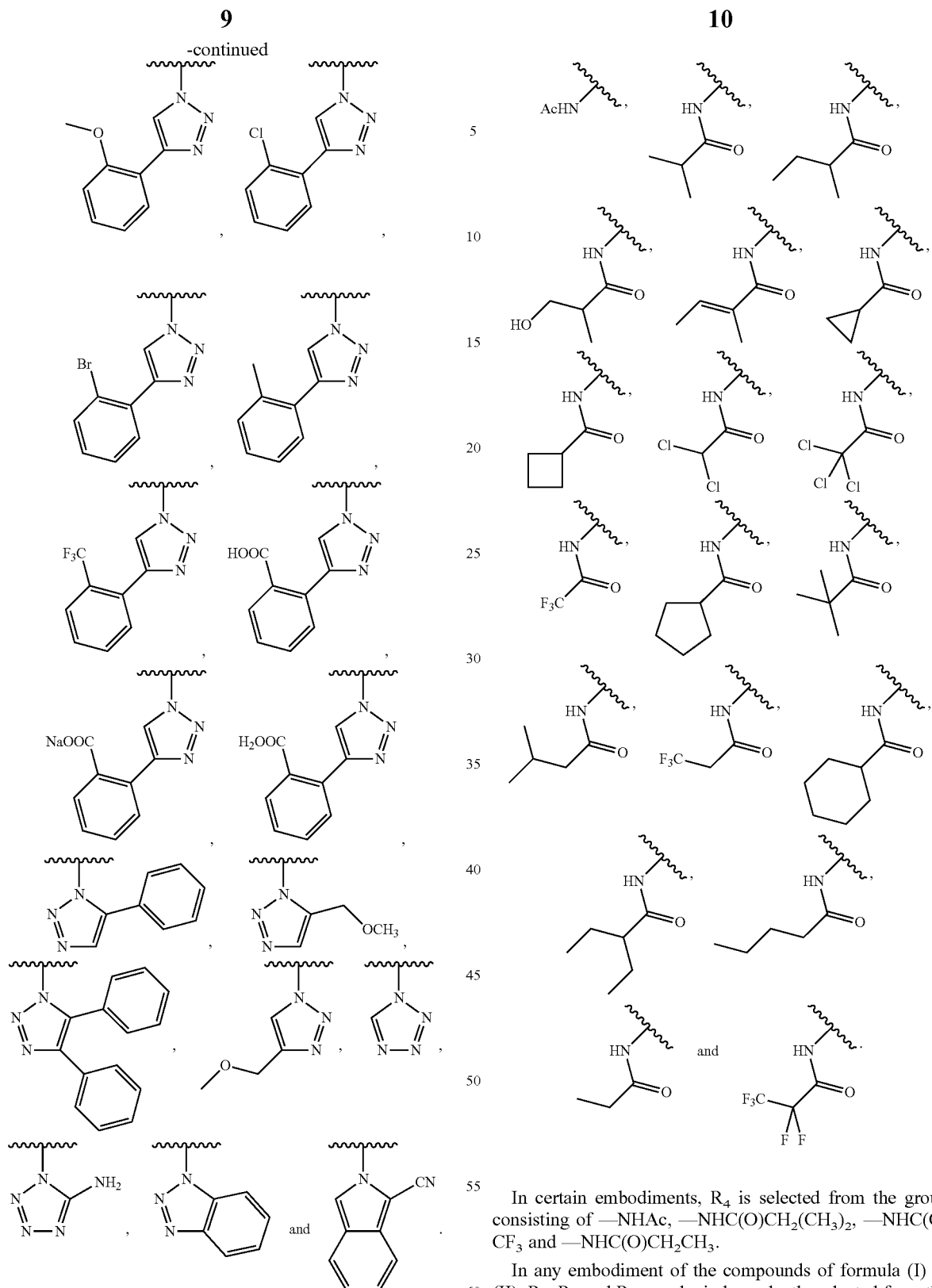

The specific moieties listed above may be combined with any disclosure of an $R_1$, $R_4$, $R_6$, $R_7$ or $R_8$ group as described herein.

In any of the aforedescribed embodiments, $R_4$ may be selected from the group consisting of:

In certain embodiments, $R_4$ is selected from the group consisting of —NHAc, —NHC(O)CH$_2$(CH$_3$)$_2$, —NHC(O)CF$_3$ and —NHC(O)CH$_2$CH$_3$.

In any embodiment of the compounds of formula (I) or (II), $R_6$, $R_7$ and $R_8$ may be independently selected from the group consisting of OH, $C_1$-$C_3$ alkoxy and —OC(O)$R_{18}$ wherein $R_{18}$ is optionally substituted $C_1$-$C_3$ alkyl.

In any one or more of the preceding embodiments, $R_6$, $R_7$ and $R_8$ may be independently selected from OH and OAc.

In embodiments of formula (I) and formula (II) the compound may be selected from the group consisting of:

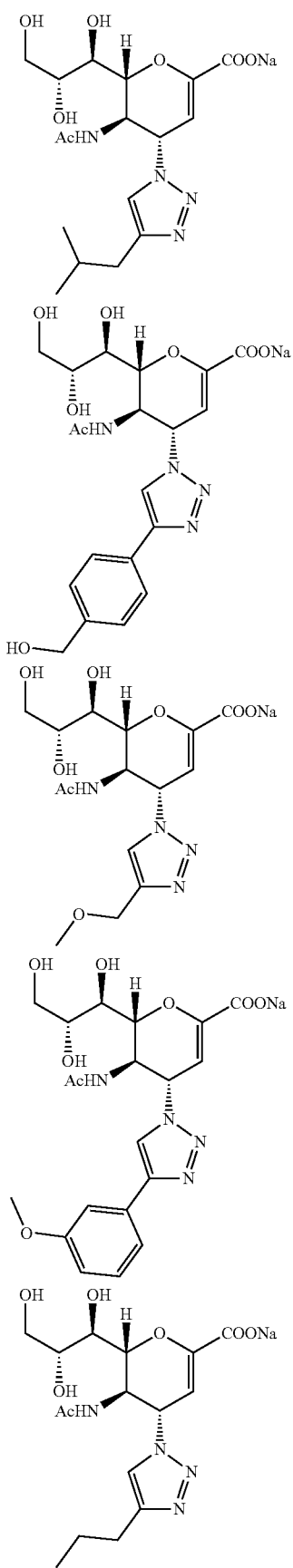
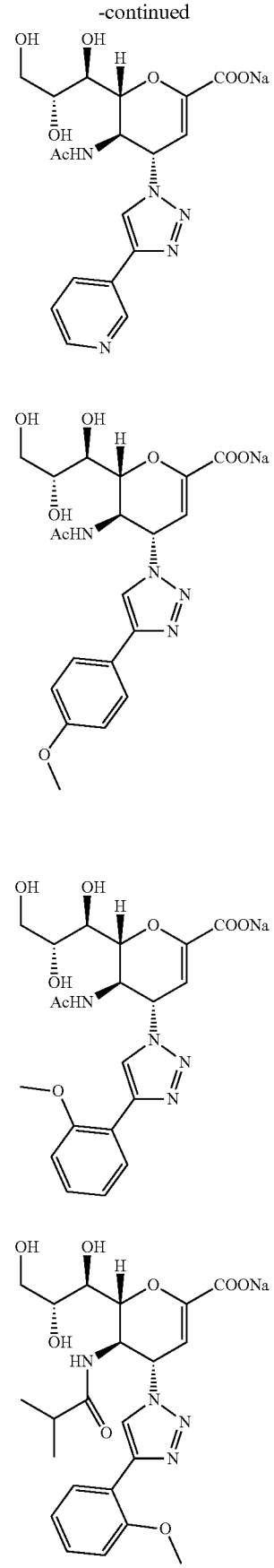

-continued
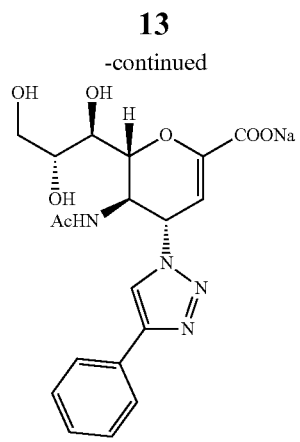
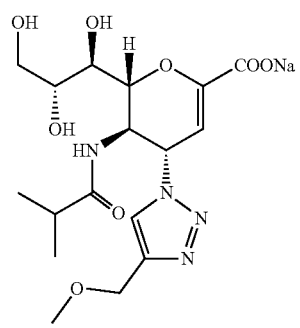
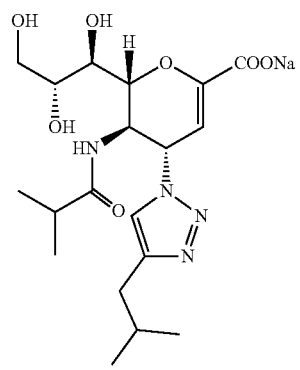
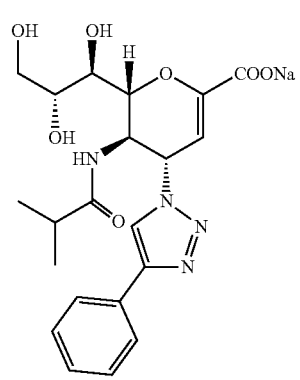
-continued
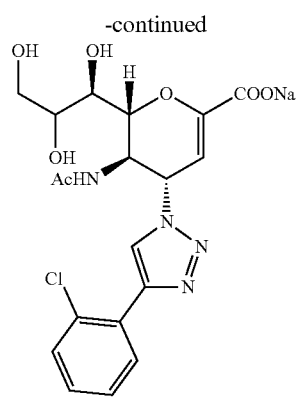
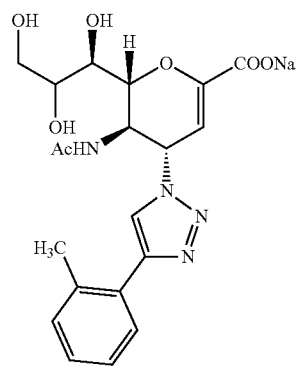
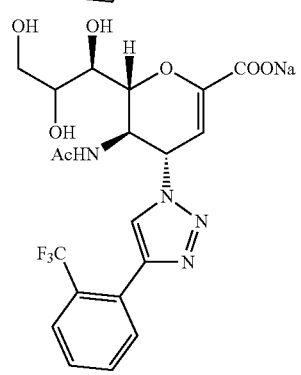
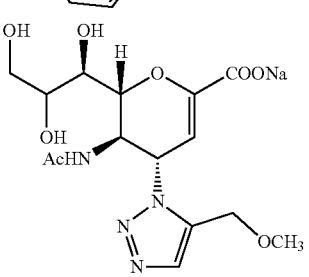
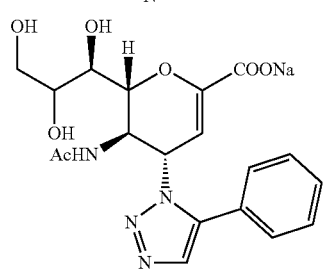

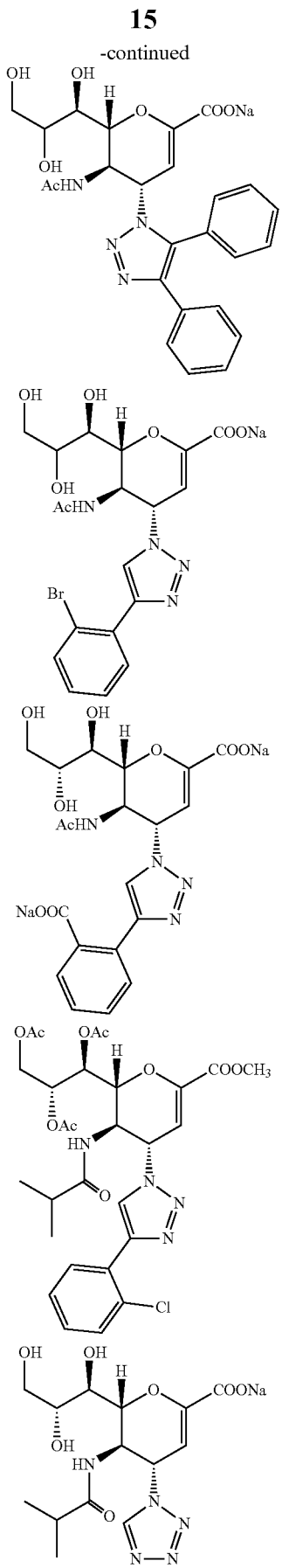

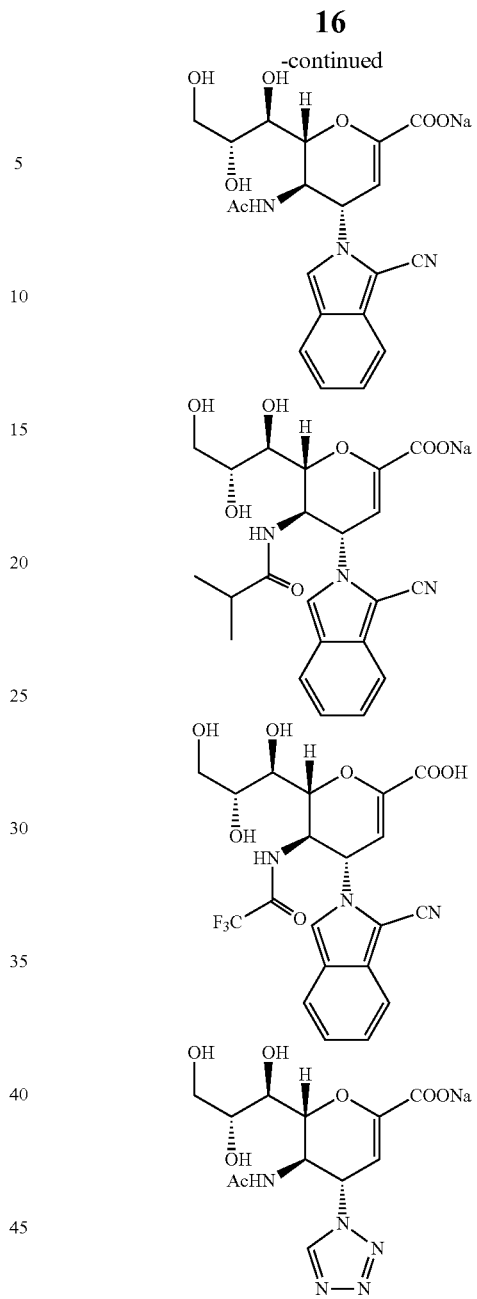

and all C-2 analogues thereof wherein the C-2 carboxy group is in the protonated form, sodium salt form or $C_1$-$C_3$ ester prodrug form and wherein each compound may be considered to have close analogues disclosed wherein the $R_4$ position is explicitly replaced with any —NHC(O)R group wherein R is $C_1$-$C_4$ alkyl or haloalkyl.

It will be appreciated by a person of skill in the art of synthetic chemistry that the COOH group is easily interchanged with a salt form or an ester protecting group, for example a methyl ester group, and so all such forms are considered to be disclosed herein with reference to the compounds listed above.

In one specific embodiment of formula (I) or formula (II), wherein $R_4$ is NHAc and $R_3$ is a substituted triazole then the triazole is not substituted with a carboxyl group.

In a further specific embodiment of formula (I) or formula (II), wherein $R_4$ is NHAc and $R_3$ is a triazole substituted only at the 4-position of the triazole ring (the 1-position being the ring nitrogen attached to the neuraminic acid core) then the triazole is not substituted with propyl, substituted propyl, substituted tert-butyl or diethoxyalkyl.

In one embodiment, the compound of the first aspect is a haemagglutinin and/or neuraminidase modulator. Preferably, a haemagluttinin and/or neuraminidase inhibitor.

In one embodiment, it may be preferred that the haemagluttinin and/or neuraminidase inhibitor is an influenza or parainfluenza haemagluttinin and/or neuraminidase inhibitor.

In one alternative aspect, referred to herein as the "difluoro" aspect, the invention resides in a compound of formula (III) or (IIIa), or a pharmaceutically acceptable salt thereof:

Formula (III)

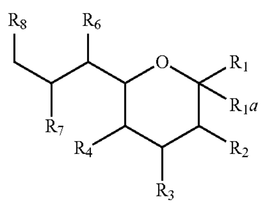

Formula (IIIa)

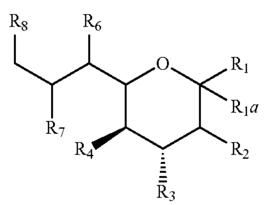

wherein, $R_1$ is selected from the group consisting of COOH, or a salt thereof, $C(O)NR_9R_{10}$, $C(O)OR_{11}$, $P(O)(OH)_2$ and $P(O)(OR)_2$;

$R_{1a}$ and $R_2$ are fluorine;

$R_3$ is selected from the group consisting of optionally substituted N-linked heterocyclic, —$NHC(O)NHR_{12}$, —$NHC(O)R_{13}$ and —$NHS(O)_2R_{14}$;

$R_4$ is selected from the group consisting of $NR_{15}R_{16}$ and $NHC(O)R_{17}$; and $R_6$, $R_7$ and $R_8$ are independently selected from the group consisting of OH, $NH_2$, $C_1$-$C_6$ alkyl, $NR_{18}R_{18}'$, $C_1$-$C_6$ alkoxy, —$OC(O)R_{18}$, —$NH(C{=}O)R_{18}$, and $S(O)_nR_{18}$, wherein n=0-2 and each $R_{18}$ and $R_{18}'$ are independently hydrogen or optionally substituted $C_1$-$C_6$ alkyl.

In one embodiment of formula (III) or formula (IIIa) $R_1$ is selected from the group consisting of COOH, or a salt thereof, and $COOR_{11}$ wherein $R_{11}$ is optionally substituted $C_1$-$C_6$ alkyl.

In one embodiment of formula (III) or formula (IIIa) $R_{11}$ is selected from methyl, ethyl, propyl, isopropyl, n-butyl, sec-butyl, isobutyl, tert-butyl and pentyl.

In one embodiment of formula (III) or formula (IIIa) $R_{12}$, $R_{13}$ and $R_{14}$ are independently selected from the group consisting of optionally substituted benzyl and phenyl.

In one embodiment of formula (III) or formula (IIIa) $R_3$ is selected from the group consisting of pyrazole, imidazole, indole, isoindole, triazole, benzotriazole, tetrazole, pyrimidine, pyridine, pyrazine, diazine, triazine and tetrazine, all of which may be optionally substituted, and which are linked to the core via a ring nitrogen.

In one embodiment of formula (III) or formula (IIIa) $R_3$ is selected from the group consisting of:

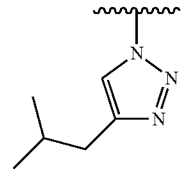

, 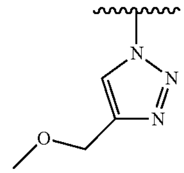  ,

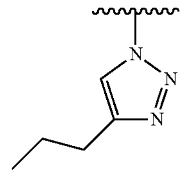

, 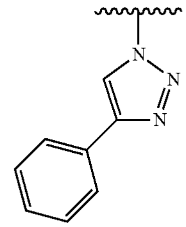  ,

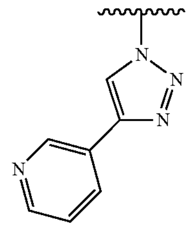

, 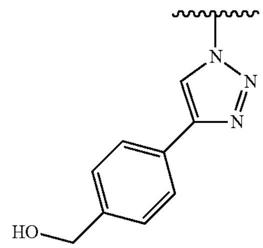  ,

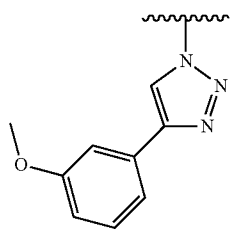

, 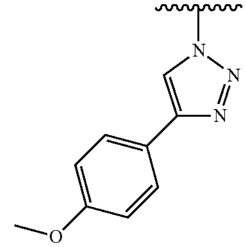  ,

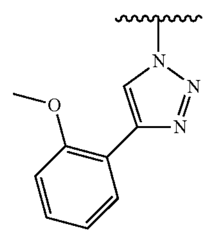

, 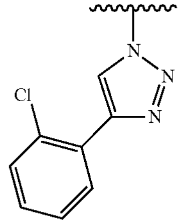  ,

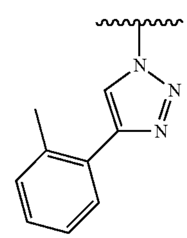

, 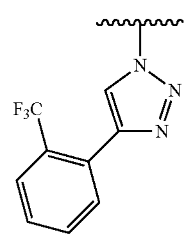  ,

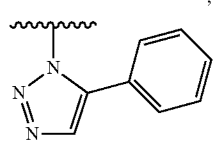

,  ,

, 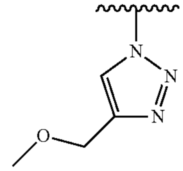  ,

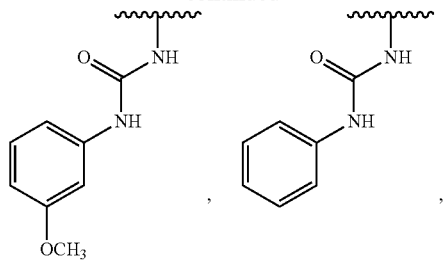
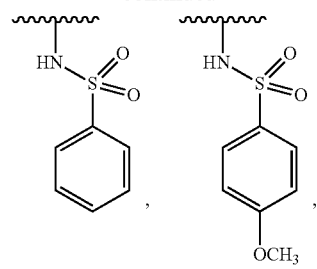
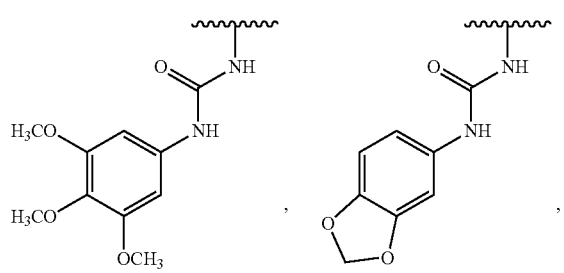
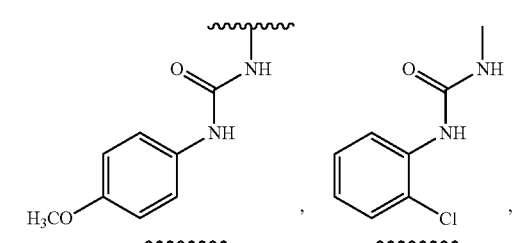
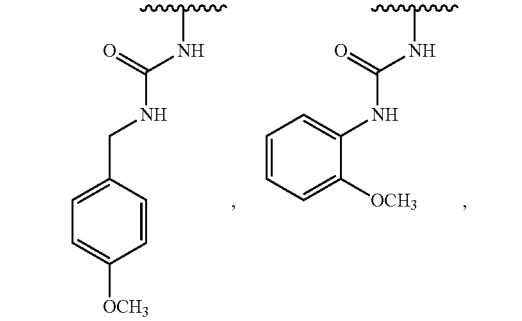
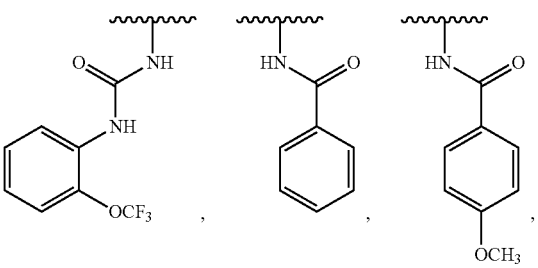
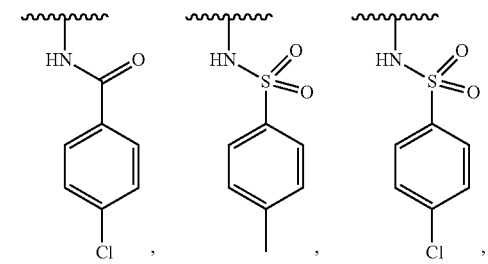

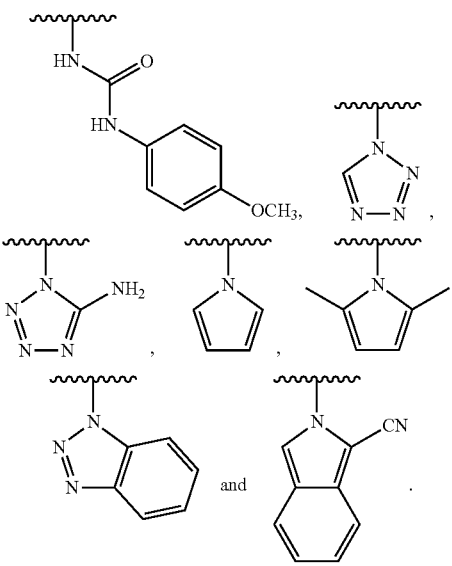

In one embodiment of formula (III) or formula (IIIa) $R_4$ is selected from the group consisting of $NR_{15}R_{16}$ and $NHC(O)R_{17}$ and wherein $R_{15}$, $R_{16}$ and $R_{17}$ are independently selected from the group consisting of optionally substituted $C_1$-$C_6$ alkyl, $C_1$-$C_6$ haloalkyl, $C_1$-$C_6$ alkenyl and $C_3$-$C_6$ cycloalkyl.

In one embodiment of formula (III) or formula (IIIa) $R_4$ is $NHC(O)R_{17}$ and wherein $R_{17}$ is selected from the group consisting of optionally substituted $C_1$-$C_6$ alkyl, $C_1$-$C_6$ haloalkyl and $C_3$-$C_6$ cycloalkyl.

In one embodiment of formula (III) or formula (IIIa) $R_4$ is selected from the group consisting of:

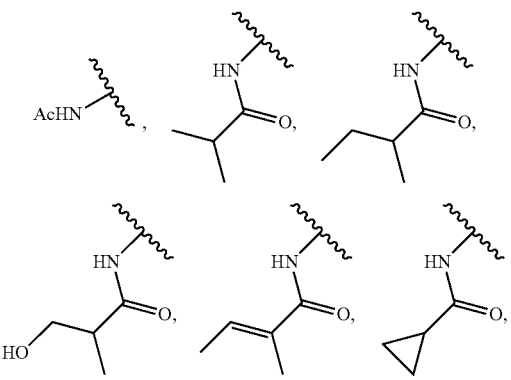

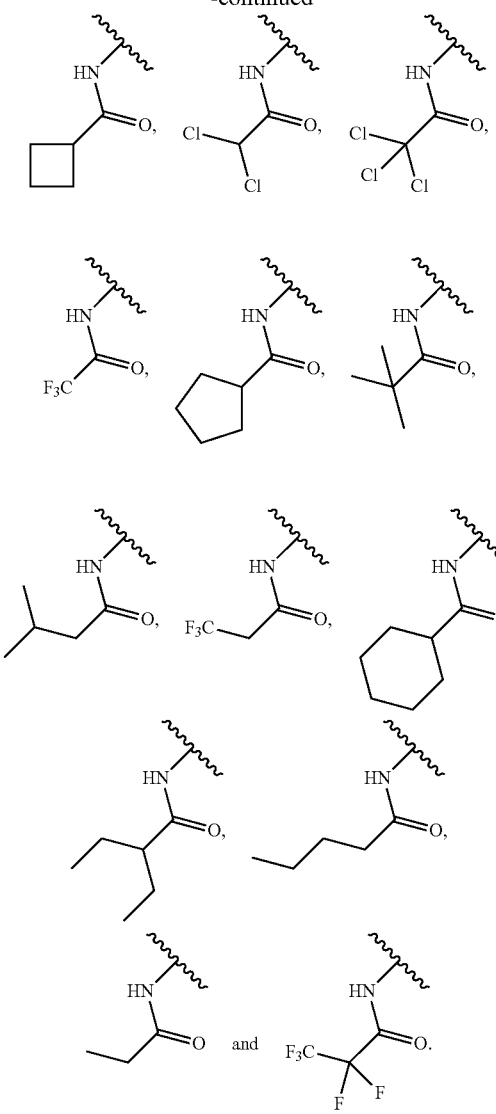

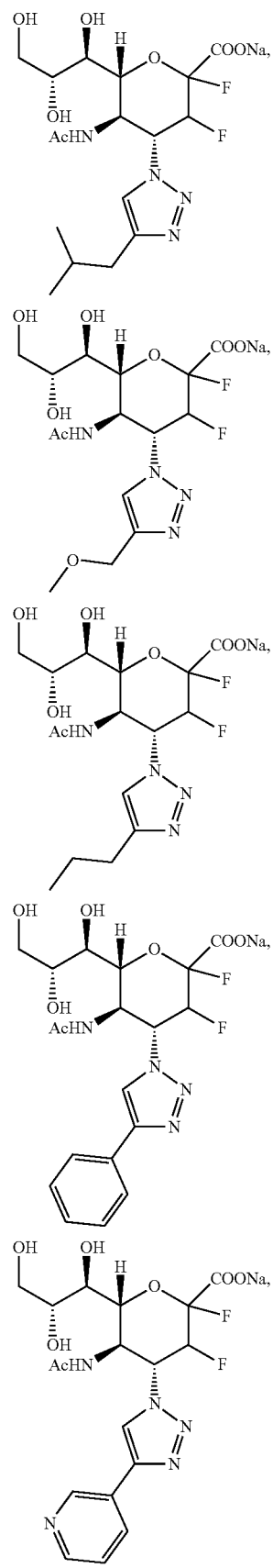

In one embodiment of formula (III) or formula (IIIa) $R_4$ is selected from —NHC(O)-methyl, —NHC(O)-ethyl, —NHC(O)-propyl, —NHC(O)-isopropyl, —NHC(O)-n-butyl, —NHC(O)-sec-butyl, —NHC(O)-isobutyl, —NHC(O)-tert-butyl and —NHC(O)-pentyl.

In one embodiment of formula (III) or formula (IIIa) $R_5$ is $C_1$-$C_6$ alkyl or $C_1$-$C_6$ alkenyl each of which may be optionally substituted.

In one embodiment of formula (III) or formula (IIIa) $R_5$ is $C_1$-$C_6$ alkyl substituted with hydroxy or protected hydroxy.

In one embodiment of formula (III) or formula (IIIa) $R_6$, $R_7$ and $R_8$ are independently selected from OH, $C_1$-$C_{10}$ alkoxy and —OC(O)$R_{18}$ wherein $R_{18}$ is $C_1$-$C_{10}$ alkyl.

In one embodiment of formula (III) or formula (IIIa) $R_6$, $R_7$ and $R_8$ are independently selected from OH and OAc.

In one embodiment of the difluoro aspect, the compound of formula (III) or formula (IIIa), or a pharmaceutically acceptable salt thereof, is selected from the group consisting of:

-continued

-continued
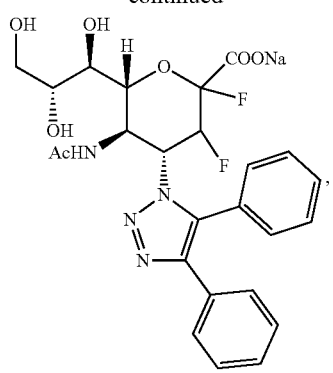
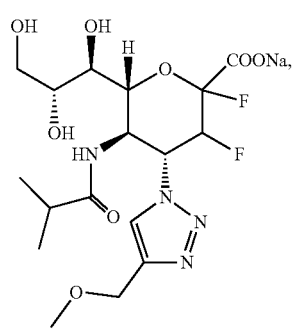
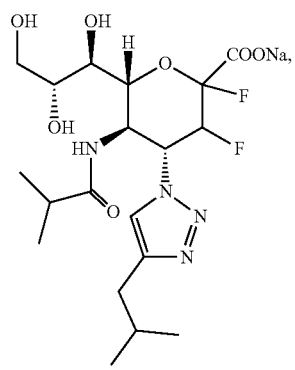
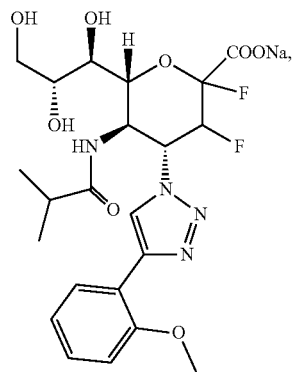
-continued
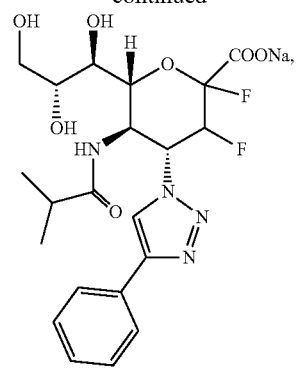
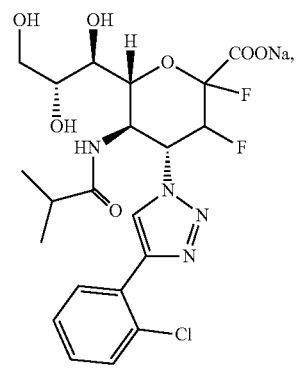
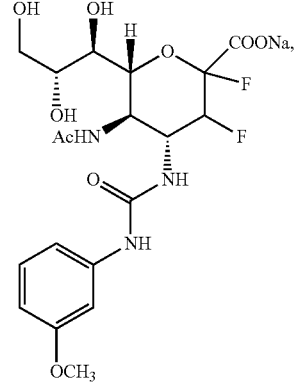
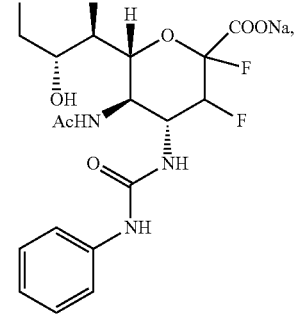

-continued
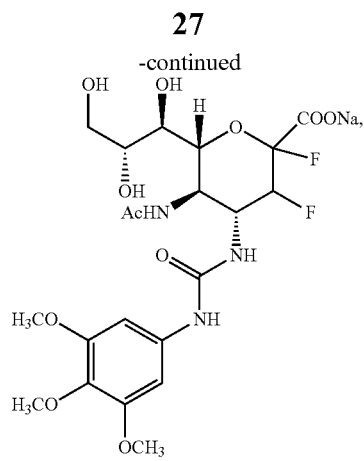
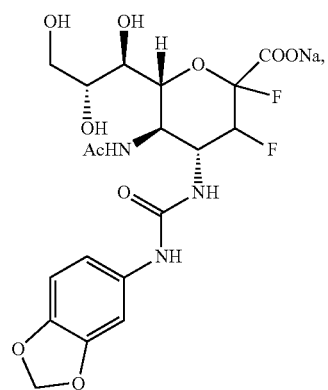
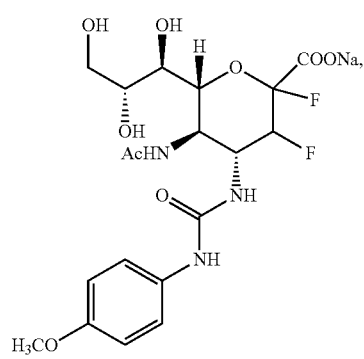
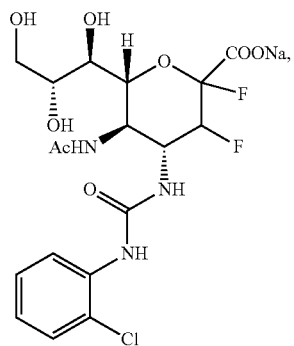
-continued
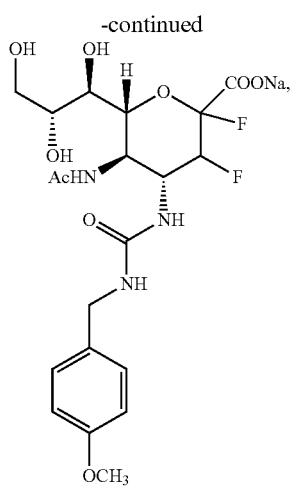
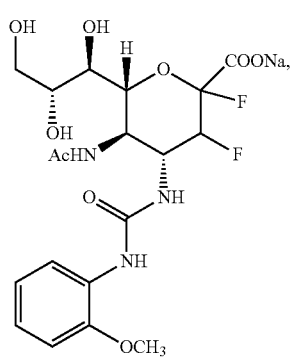
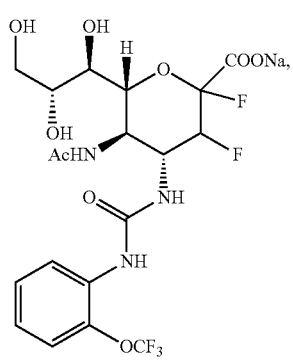
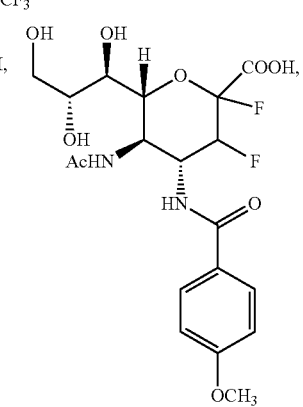

29
-continued
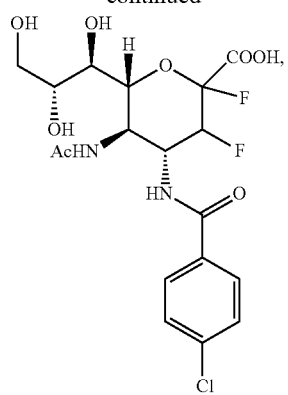
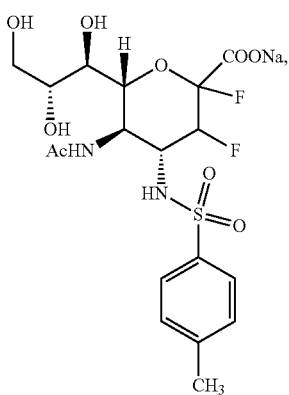
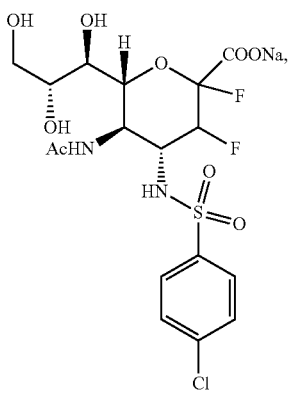
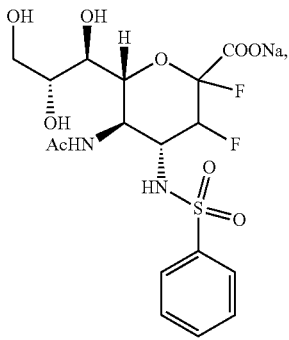
30
-continued
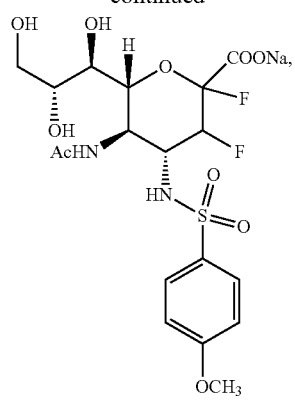
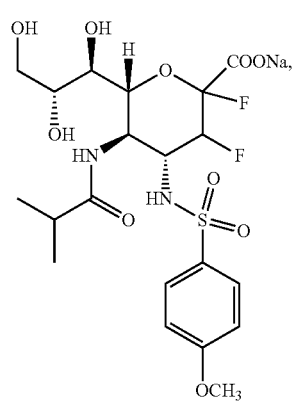
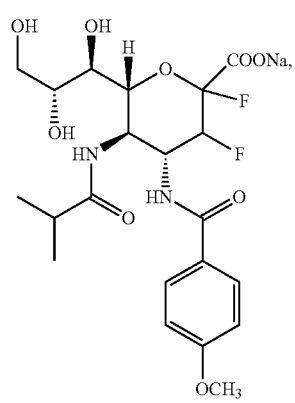
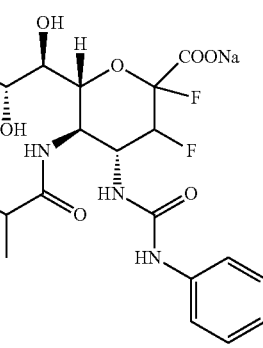

-continued
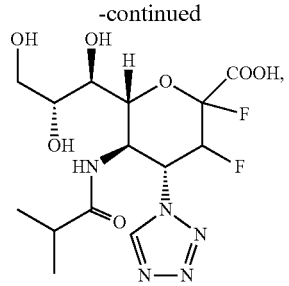
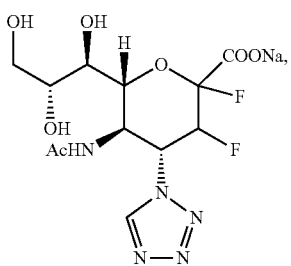
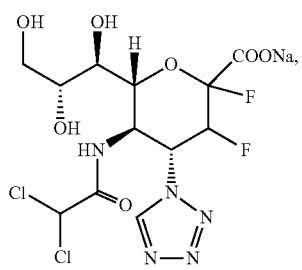
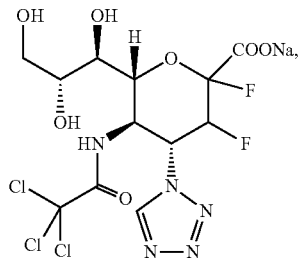
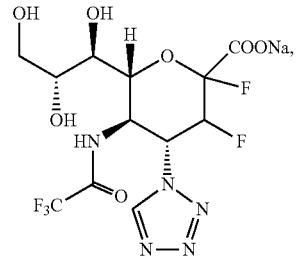
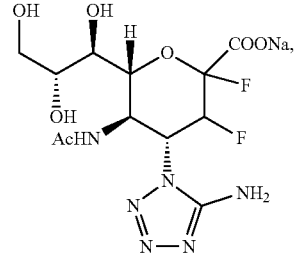
-continued
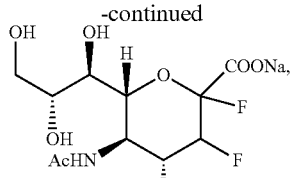
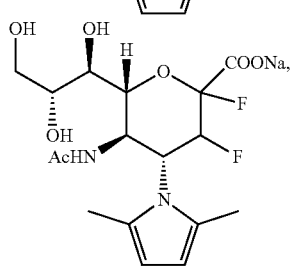
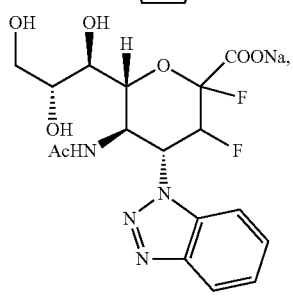
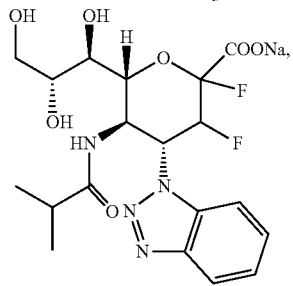
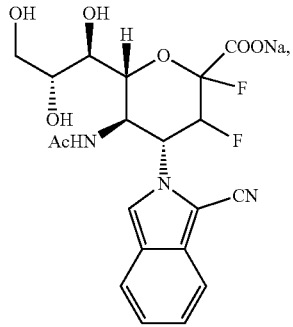
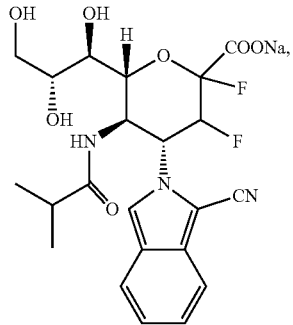

33
-continued
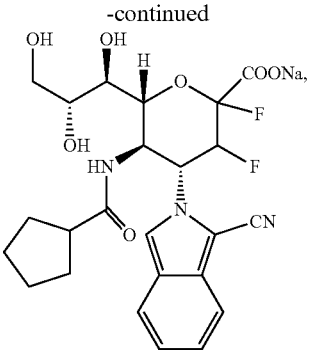
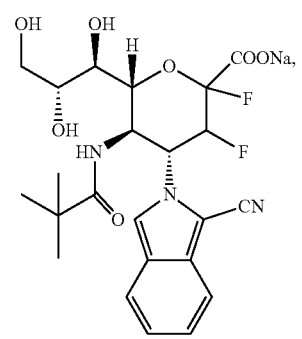
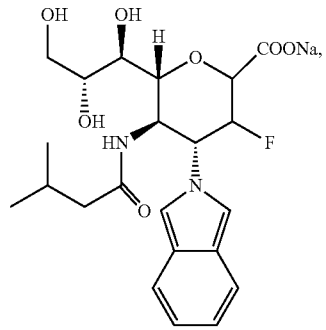
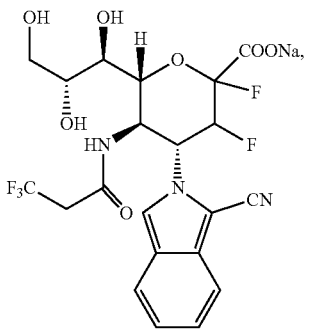
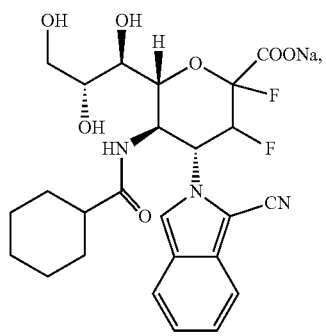
34
-continued
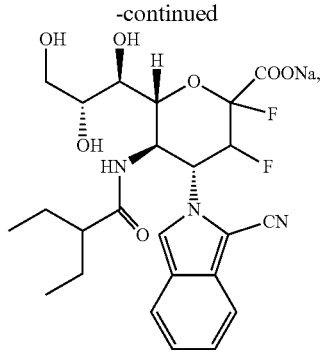
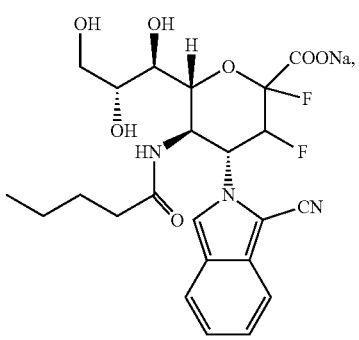
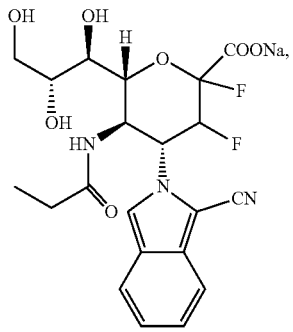
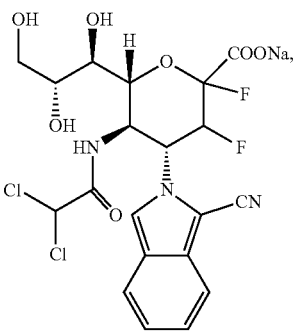
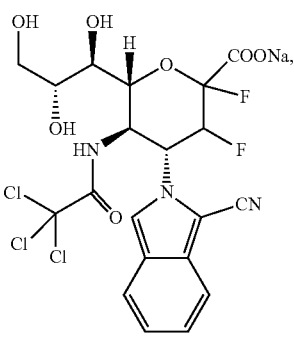

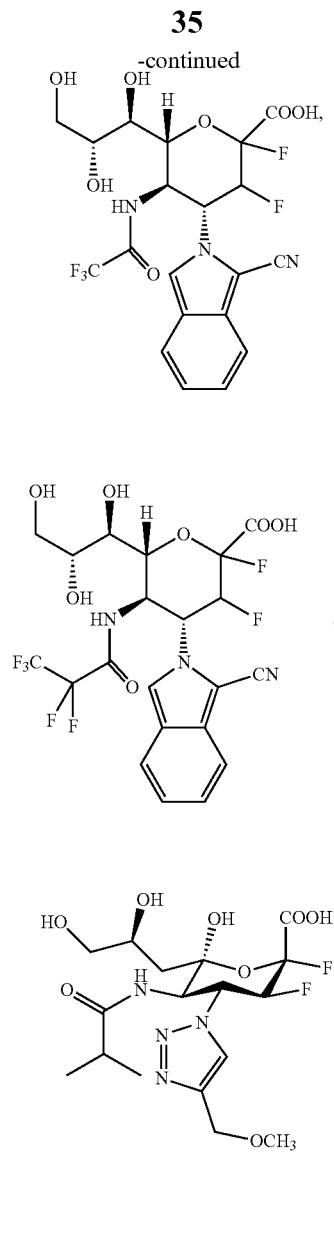

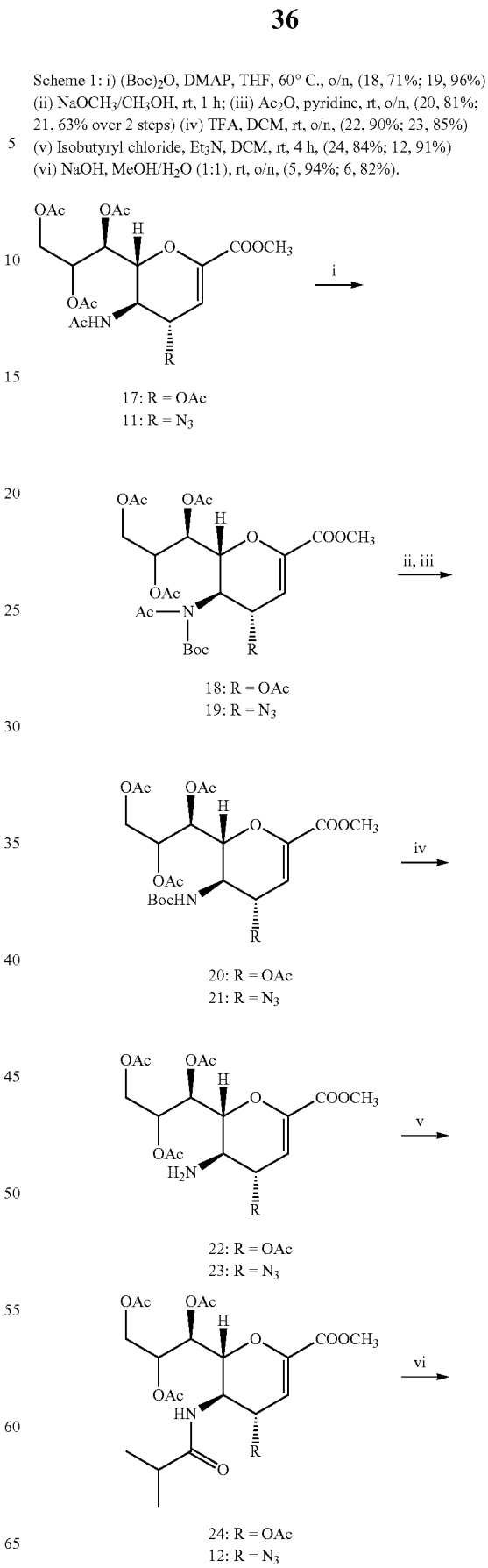

Scheme 1: i) (Boc)₂O, DMAP, THF, 60° C., o/n, (18, 71%; 19, 96%)
(ii) NaOCH₃/CH₃OH, rt, 1 h; (iii) Ac₂O, pyridine, rt, o/n, (20, 81%; 21, 63% over 2 steps) (iv) TFA, DCM, rt, o/n, (22, 90%; 23, 85%)
(v) Isobutyryl chloride, Et₃N, DCM, rt, 4 h, (24, 84%; 12, 91%)
(vi) NaOH, MeOH/H₂O (1:1), rt, o/n, (5, 94%; 6, 82%).

wherein each incidence of COOH may be read interchangeably with COONa, and vice versa.

In any of the above embodiments of formula (III) or formula (IIIa) it may be that $R_3$ is not N-linked aryl, that is, an aryl ring linked to the core via an intermediate nitrogen atom.

It is postulated that compounds such as those represented by formula (III) and (IIIa), wherein there is a C-2 and 3 fluoro substitution pattern, may be particularly efficacious against influenza strains. While not wishing to be bound by any particular theory it is believed such compounds are active by virtue of being effective inhibitors of the viral neuraminidase.

A number of synthetic pathways can be employed to access the compounds of the invention. Scheme 1, below, shows one pathway by which certain known neuraminidase inhibitors were synthesised to use as reference compounds. Relevant synthetic techniques, which may also be applied to synthesis of compounds of the first aspect, are disclosed in *Carbohydr. Res.* 244, 181-185 (1993); *Carbohydr. Res.* 342, 1636-1650 (2007); *Bioorg. Med. Chem. Lett.* 16, 5009-5013 (2006); and PCT application WO2002076971.

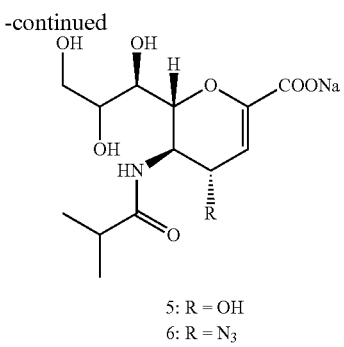

5: R = OH
6: R = N₃

Scheme 2, below, shows a synthetic route used to access compounds 7-10 which are preferred compounds of the first aspect.

Scheme 2: (i) CuSO₄, Na-ascorbate, tert-butanol/H₂O (1:1), 45° C., 6 h (13, 78%; 14, 82%; 15, 71%; 16, 84%); (ii) NaOH, MeOH/H₂O (1:1), rt, o/n (7, 85%; 8, 96%; 9, 92%; 10, 89%).

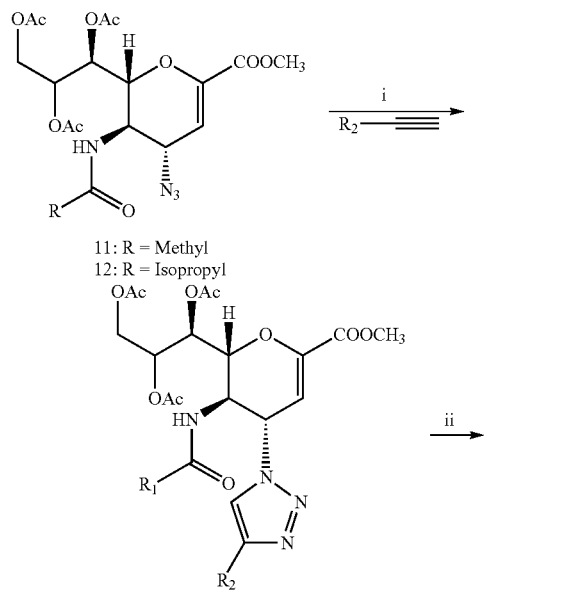

11: R = Methyl
12: R = Isopropyl

13: $R_1$ = Methyl, $R_2$ = $CH_2OCH_3$
14: $R_1$ = Methyl, $R_2$ = Ph
15: $R_1$ = Isopropyl, $R_2$ = $CH_2OCH_3$
16: $R_1$ = Isopropyl, $R_2$ = Ph

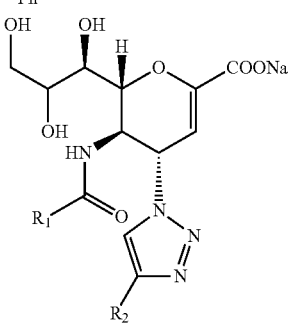

Figure 1:
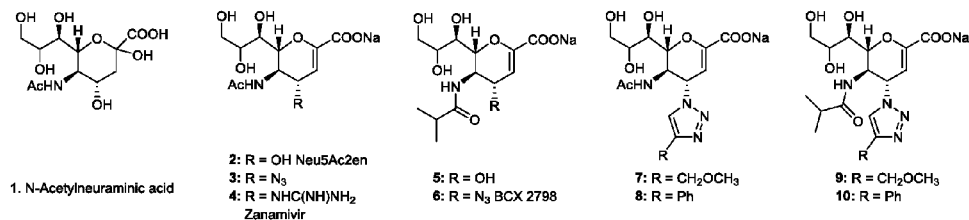
FIG. 1 shows the structures of N-acetylneuraminic acid (1), the sialidase inhibitor Neu5Ac2en (2), 4-azido-4-deoxy-Neu5Ac2en (3) zanamivir (4), the C-5 isobutyramido analogue of Neu5Ac2en (5), the reference hPIV inhibitor BCX 2798 (6), and the novel inhibitors 7-10.

7: $R_1$ = Methyl, $R_2$ = $CH_2OCH_3$
8: $R_1$ = Methyl, $R_2$ = Ph
9: $R_1$ = Isopropyl, $R_2$ = $CH_2OCH_3$
10: $R_1$ = Isopropyl, $R_2$ = Ph In brief, the synthesis of the triazoles 7-10 was achieved using the known 4-azido-4-deoxy-Neu5Ac2en based intermediates 11 and 12. Each of the two intermediates was exposed to either methylpropargyl ether or ethynylbenzene under typical click azide-alkyne coupling conditions (heating a mixture of the 4-azido-4-deoxy-Neu5Ac2en derivative, alkyne, CuSO₄ and sodium ascorbate in a (1:1) mixture of water and tert-butanol for 6 h) to afford the triazole derivative (FIG. 1). Triazoles 13 and 14 (starting from 11) and the triazole derivatives 15 and 16 (starting from 12) were isolated in yields of 78%, 82%, 71% and 84%, respectively. The resulting per-O-acetylated triazole derivatives 13-16 were then deprotected by treatment with aqueous methanol (50%) adjusted to pH 13-14 at RT for 24 h to yield the final products 7-10 as sodium salts in 85%, 96%, 92% and 89% yields, respectively.

The synthetic targets were, in part, driven by information gleaned from molecular modelling of the hPIV-3 HN crystal structure. Particularly, the 216 loop of the hPIV-3 HN indicates significant flexibility and so it was postulated that Neu5Ac2en derivatives with somewhat bulky C4 substituents could be accommodated in and lock open the 216 cavity within the active site. Molecular Dynamics (MD) simulations were employed to design and assess Neu5Ac2en derivatives that incorporate C4 functionalised triazoles, as a base from which to test the theory. From the initial study of 216 loop flexibility and the resultant 216 cavity dimensions, it was felt that relatively bulky C4 substituents on the unsaturated neuraminic acid-based template (compounds 7-10 shown in FIG. 1) could be well tolerated within the open 216 cavity. Furthermore, modelling of these C4 triazole substituted inhibitors in complex with hPIV-3 HN indicated that both an acetamido (7, 8) and an isobutyramido (9, 10) moiety at C5 on the template could also be well accommodated simultaneously within the C5 binding domain. It was assessed, using MD simulations, the capacity of the bulkier triazole compounds (8 and 10) to efficiently lock open the 216 loop in hPIV-3 HN. The relative interaction energies of 8 and 10 in complex with hPIV-3 HN were determined to predict if the bulkier C5 acylamino moiety, in combination with the bulky C4 substituent, would be expected to improve inhibitor affinity.

The methodology of the modelling and biological evaluation are discussed in detail in the experimental section but, briefly, led to a number of conclusions concerning the influence of C4/C5 substituents on inhibitor potency. Within each of the two screened groups, that is Group 1 (C5 acetamido) and Group 2 (C5 isobutyramido), the order of potency based on the substituent at C4 was found to be as follows: hydroxyl<azido≤4-methoxymethyltriazole<4-phenyltriazole. The weakest inhibition in both groups was observed for the 4-hydroxy derivatives 2 and 5. This outcome supports the notion that the C4 binding domain, which accommodates the C4 hydroxyl group on Neu5Ac2en (2), has significant hydrophobic character and consequently does not favour the interaction with a polar, hydrophilic group including a hydroxyl group. The hydrophobic nature of the pocket, combined with the large 216 cavity size created by the opening of the 216 loop, does favour inhibitors, including inhibitors 8 and 10, that have the C4 hydroxyl group replaced with bulky hydrophobic substituents.

Comparison of both group's $IC_{50}$ values revealed that replacement of the C5 acetamido group with an isobutyramido group in all of the prepared inhibitors led to overall enhanced potency. Typically, close to an order of magnitude improvement was observed, except for the most potent inhibitor 10. Furthermore, analysis of the $IC_{50}$ values supports the notion that the potency enhancement in the best inhibitors, 8 and 10, results predominantly from the introduction of the C4 substituent, with the C5 substituent contributing to a much lesser extent. This notion is also substantiated by STD NMR data analysis that led to an epitope map of inhibitor 10 in which the protons of the 4-phenyltriazole moiety showed the strongest contribution to the binding event of 10 in complex with hPIV-3 HN, while the relative interactions observed for the isobutyramido group were less (50%).

The potent inhibition of both HN functions (NI and HI) by inhibitor 10 demonstrates that the compound exerts its antiviral effect against hPIV-3 by action on the virus' key HN protein. These findings are further supported by STD NMR experiments of 10 in complex with either intact virus or recombinant HN protein, that clearly show identical STD NMR signal intensities for the inhibitor's C4 triazole aromatic moiety. Moreover, the calculated binding epitope for 10 in complex with hPIV-3 HN is in excellent agreement with the MD simulations that clearly predict the close contact of the Neu5Ac2en derivative's H3 and the C4 triazolo moiety's phenyl protons to the protein surface.

Furthermore, the in situ ELISA results are in good agreement with the NI and HI assay data. The LLC-MK2 cell-based assays demonstrate that 10 is even more potent at the cellular level compared to NI and HI protein-based assays. In this cell-based assay 10 was found to be ~26 times more potent than 6, whereas protein inhibition assays showed only ~8 and 11 fold improvement in NI and HI assays, respectively. This strongly suggests 10 is a potent dual acting inhibitor that derives efficient synergism from the inhibition of both the protein's neuraminidase and haemagglutinin activities. This is in contrast to the known inhibitor 6, which derives less synergistic effect as a result of it's significantly poorer inhibition of the haemagglutinin activity. Finally, the extent of virus growth inhibition in both human cell lines for inhibitor 10 compared with 6 clearly demonstrates the superiority of the designer ligand 10.

It will be appreciated that the compounds of the first aspect have efficacy at more than just the hPIV-3 HN. It has been found, as indicated in the experimental section, that variations in the structure of the compound can tailor the activity to different hPIV or influenza neuraminidases generally. For example, the difluoro derivatives disclosed herein may be preferentially active against certain influenza neuraminidases.

Particularly, the results indicate that not only is compound 10 a much better inhibitor than prior art compound BCX-2798 (reference compound 6) in an inhibition assay to compare their capacity to inhibit hPIV-3 virus infection and propagation in LLC-MK2 cells by a reduction of 94% versus 14%, respectively, but other compounds of the first aspect have been shown to have even greater potency than 10 or 6. For example, the inventors have designed, synthesised and biologically evaluated compounds IE1398-33 and IE927-99. These compounds have IC50 values for hPIV-3 HN of 1.97 micromolar and 0.27 micromolar, respectively. This represents a 1 to 2 order of magnitude improvement over the prior art reference compound BCX-2798. These results demonstrate the surprising level of efficacy of the present compounds and hence the value of the present structure-guided inhibitor design.

According to a second aspect of the invention there is provided a pharmaceutical composition comprising an effective amount of a compound of formula (I), (II), (III) or (IIIa), or a pharmaceutically acceptable salt thereof, and a pharmaceutically acceptable carrier, diluent and/or excipient.

Suitably, the pharmaceutical composition is for the treatment or prophylaxis of a disease, disorder or condition caused by viral infection.

The pharmaceutical composition may include more than one compound of formula (I), (II), (III) or (IIIa). When the composition includes more than one compound then the compounds may be in any ratio. The composition may further comprise known co-actives, delivery vehicles or adjuvants.

The compound of formula (I), (II), (III) or (IIIa) is present in the pharmaceutical composition in an amount sufficient to inhibit or ameliorate the disease, disorder or condition which is the subject of treatment. Suitable dosage forms and rates of the compounds and the pharmaceutical compositions containing such may be readily determined by those skilled in the art.

Dosage forms may include tablets, dispersions, suspensions, injections, solutions, syrups, troches, capsules and the like. These dosage forms may also include injecting or implanting devices designed specifically for, or modified to, ensure placement at the site of connective tissue degradation. A hydrogel is a preferred delivery form.

A third aspect of the invention resides in a method of treating a disease, disorder or condition caused by viral infection in a patient including the step of administering an effective amount of a compound of formula (I), (II), (III) or (IIIa), or a pharmaceutically effective salt thereof, or the pharmaceutical composition of the second aspect to the patient.

A fourth aspect of the invention provides for a compound of formula (I), (II), (III) or (IIIa), or a pharmaceutically effective salt thereof, or the pharmaceutical composition of the second aspect for use in the treatment of a disease, disorder or condition caused by viral infection in a patient.

A fifth aspect of the invention provides for use of a compound of formula (I), (II), (III) or (IIIa), or a pharmaceutically effective salt thereof, in the manufacture of a medicament for the treatment of a disease, disorder or condition caused by viral infection.

In one embodiment of the third, fourth or fifth aspects, the disease, disorder or condition is an infection caused by influenza or parainfluenza virus.

The infection may be caused by the influenza A, B or C or parainfluenza virus.

In one embodiment, the parainfluenza is an hPIV-1, 2, 3 or 4 virus.

Preferably, the patient is a domestic or livestock animal or a human.

A sixth aspect of the invention provides for a method of modulating the activity of a viral haemagglutinin and/or neuraminidase enzyme including the step of contacting the enzyme with a compound of formula (I), (II), (III) or (IIIa).

Preferably, the modulating involves inhibiting the viral haemagglutinin and/or neuraminidase enzyme.

The following experimental section describes in more detail the characterisation of certain of the compounds of the invention and their antiviral activity. The intention is to illustrate certain specific embodiments of the compounds of the invention and their efficacy without limiting the invention in any way.

EXPERIMENTAL

Computational Chemistry

Molecular Dynamics simulations were performed with GROMOS software using the force-field parameter set 54A4 (ref 39). Initial coordinates were taken from the X-ray structure (PDB accession code 1V3E) of hPIV-3 HN in complex with 4 (FIG. 1). Compound 8 was superimposed on zanamivir (4) ring atoms from the crystal structure. Parameters for 8 were generated in an analogous manner to existing parameters in the GROMOS force-field. The number of atoms in the final composite system for 1V3E-4 and IV3E-8 was 78253 and 78084, respectively. Ionization states of amino acid residues were assigned at pH 7.0. The histidine side chains were protonated at the NE-atom. Water molecules associated with the X-ray structure were removed, and replaced by explicit solvation using the simple-point-charge (SPC) water model and periodic boundary conditions, consistent with previously published methodology. In the simulations, water molecules were added around the protein within a truncated octahedron with a minimum distance of 1.4 nm between the protein atoms and the square walls of the periodic box. All bonds were constrained with a geometric tolerance of $10^{-4}$ using the SHAKE algorithm.

A steepest-descent energy minimization of the system was performed to relax the solute-solvent contacts, while positionally restraining the solute atoms using a harmonic interaction with a force constant of $2.5 \times 10^4$ kJ mol$^{-1}$ nm$^{-2}$. Next, steepest-descent energy minimization of the system without any restraints was performed to eliminate any residual strain. The energy minimizations were terminated when the energy change per step became smaller than 0.1 kJ mol$^{-1}$. For non-bonded interactions, a triple-range method with cut-off radii of 0.8/1.4 nm was used. Short-range van der Waals and electrostatic interactions were evaluated at each time step, based on a charge-group pair-list. Medium-range van der Waals and electrostatic interactions, between (charge group) pairs at a distance longer than 0.8 nm and shorter than 1.4 nm, were evaluated every fifth time step, at which point the pair list was updated. Outside the longer cut-off radius a reaction-field approximation was used with a relative dielectric permittivity of 78.5. The centre of mass motion of the whole system was removed every 1000 time steps. Solvent and solute were independently, weakly coupled to a temperature bath of 295 K with a relaxation time of 0.1 ps.

The systems were also weakly coupled to a pressure bath of 1 atm with a relaxation time of 0.5 ps and an isothermal compressibility of $0.7513 \times 10^{-3}$ (kJ mol$^{-1}$ nm$^{-3}$)$^{-1}$. MD simulations of 20 ps periods with harmonic position restraining of the solute atoms and force constants of $2.5 \times 10^4$ kJ mol$^{-1}$ nm$^{-2}$, $2.5 \times 10^3$ kJ mol$^{-1}$ nm$^{-2}$, $2.5 \times 10^2$ kJ mol$^{-1}$ nm$^{-2}$, $2.5 \times 10^1$ kJ mol$^{-1}$ nm$^{-2}$ were performed to further equilibrate the systems at 50 K, 120 K, 1800 K, 240 K and 300 K, respectively. The simulations were each carried out for 30 ns. The trajectory coordinates and energies were saved every 0.5 ps for analysis. Simulation trajectories for hPIV-3 HN in complex with 4 were produced in an analogous manner to that described above and were used for analysis and comparison to results obtained for hPIV-3 HN in complex with 8.

Analyses were done with the analysis software GROMOS++. Atom-positional root-mean-square differences (RMSDs) between structures were calculated for the residues comprising the 216-loop (residues 210-221) by performing a rotational and translational atom-positional least-squares fit of one structure on the second (reference) structure using a given set of atoms (N, $C_\alpha$, C). Atom-positional root-mean-square fluctuations (RMSFs) were calculated as an average from a 30 ns period of simulation by performing a rotational and translational atom-positional least-squares fit of the $C_\alpha$-atoms of the trajectory structures on the reference. RMSFs were calculated for all residues including the 216-loop (residues 210-221). To obtain reduced, representative structural ensembles for the simulations, RMSD-based conformational clustering was performed.

Structures extracted every 10 ps from simulations were superimposed on backbone-$C_\alpha$ atoms to remove overall rotation and translation. Clustering of all atoms of residues that line the binding site (residues 190-198, 210-221, 251-259, 274-280, 320-326, 334-339, 369-377, 407-413, 474-480, 529-533) was performed to compare relative structural populations of hPIV-3 HN protein from the different simulation trajectories. The similarity criterion applied was the RMSD of all atoms of these residues with a cut-off of 0.13 nm. Final structures resulting from the 30 ns of MD simulations were extracted. Interaction energies between hPIV-3 HN and inhibitors 8 and 10 were calculated using GROMOS generated energies, free-energy A-derivatives and block averages as separate trajectory files, referred to as the energy trajectory. The program ene_ana was used to extract individual interaction energy values such as non-bonded contributions, i.e. van der Waals and Coulomb interactions from these files. Thus, these contributions between the ligand and the protein were extracted from the energy trajectory resulting from the simulation and interaction energies calculated. The error estimate was calculated from block averages of growing sizes extrapolating to infinite block size. Hydrophobic interactions were analysed and a map of interactions between inhibitor 10 and hPIV-3 HN was created using LIGPLOT. To measure the extent of cavity opening for selected structures, the pocket volume was analysed using POVME. Importantly, extended simulation times, up to 80 ns provided outcomes entirely consistent with the data presented.

Compound 8 as a Model of a Neu5Ac2En-Based hPIV-3 HN Inhibitor with a Bulky C4 Substituent The simulation of the available hPIV-3 HN crystal structure (PDB accession code 1V3E) in complex with 8 allowed an analysis of the dynamic behaviour of the protein relative to the zanamivir (4) bound structure. Atom-positional root-mean-square deviations (RMSDs) of the hPIV-3 HN backbone atoms ($C_a$, N, C) for the 216-loop from the simulations of the hPIV-3 HN-4 and -8 complexes showed that the 216-loop undergoes more significant deviations from the crystal structure in the case of the hPIV-3 HN-8 complex. RMSD-values of larger than 0.5 nm are observed for the simulation of the hPIV-3 HN-8 complex, whereas the structure deviates less (0.4 nm) for the hPIV-3 HN-4 complex. This notion is further supported by the root-mean-square fluctuations (RMSFs) observed for the $C_a$-atoms of the backbone for residues associated with the 216-loop (residues 205-225). Increased RMS fluctuations are observed for the residues of the second half of the 216-loop (215-220), where values of ~0.3 nm are reached, indicating a substantial conformational rearrangement within that domain compared with the starting hPIV-3 HN reference X-ray structure (PDB accession code IV3E). Table 1 shows a selection of RMSF values of residues comprised in the 216-loop.

TABLE 1

Root-Mean-Square Fluctuations (RMSF) of selected residues comprised in the 216-loop for the 1V3E-4 and 1V3E-8 simulated systems, in nanometers, compared with the reference X-ray structure IV3E

| Residue | Reference X-ray structure (IV3E) | 1V3E-4 | 1V3E-8 |
|---|---|---|---|
| 210 | 0.036 | 0.059 | 0.056 |
| 212 | 0.046 | 0.104 | 0.141 |
| 214 | 0.048 | 0.093 | 0.109 |
| 216 | 0.057 | 0.111 | 0.162 |
| 218 | 0.060 | 0.134 | 0.289 |
| 220 | 0.041 | 0.070 | 0.079 |

The data suggests that loop flexibility, present under physiological simulation conditions, has been significantly underestimated in crystal structures and provides an opportunity for anti-parainfluenza virus drug discovery. Comparison of the hPIV-3 HN-4 complex and the hPIV-3 HN-8 complex simulations demonstrates that the C4 substituent on 8 induces significant movement in the hPIV-3 HN 216-loop. The induced loop opening could be seen from the solvent-accessible surface plots of the final structures obtained from 10 ns simulations of hPIV-3 HN-4 complex and 8.

The most populated conformational clusters from the MD simulations of hPIV-3 HN in complex with 4 and 8 were identified and the superposition of the final conformations from the simulations of hPIV-3 HN in complex with 4 and 8 were generated. The difference in 216-loop conformation could clearly be seen. The 216-loop cavity adopts a more open conformation when in complex with the more sterically-encumbered inhibitor 8. Generally, a wider cavity is observed for the simulation of hPIV-3 HN-8 complex. The most populated cluster from the simulation of the hPIV-3 HN-4 complex has a slightly smaller cavity volume (654 $Å^3$) compared to the simulated hPIV-3-8 complex (717 $Å^3$).

To evaluate if a bulkier C5 acylamino moiety would be accommodated in the presence of the C4 functionalised triazole an identical analysis of 10 in complex with hPIV-3 HN was undertaken. This analysis indicated that a C5 isobutyramido moiety is well accommodated within the C5 binding domain in the presence of the C4 functionalised triazole.

Relative Interaction Energies of 8 and 10 in Complex with hPIV-3 HN

To quantify the extent of inhibitor engagement with hPIV-3 HN an MD simulations approach was used to determine theoretical averaged interaction energies for the known inhibitor 2, as well as the novel C5 acetamido and C5 isobutyramido inhibitors, 8 and 10 respectively. Average interaction energy ($E_{avl}$) values of −609.38±10.92 kJ $mol^{-1}$, −733.96±15.49 kJ $mol^{-1}$ and −821.88±10.93 kJ $mol^{-1}$ for 2, 8 and 10 respectively in complex with hPIV-3 HN (1V3E)[25] were determined. These calculations support the notion that the replacement of the acetamido moiety in 8 with an isobutyramido moiety in 10 significantly improves the absolute $E_{avl}$ value of the inhibitor in complex with the protein. Consequently, 10 is predicted to be a more potent hPIV-3 HN inhibitor than 8. Further analysis of the MD simulation and extraction of the lowest (−1,078.13 kJ $mol^{-1}$) interaction energy structure of 10 in complex with hPIV-3 HN (1V3E) revealed that 10 makes several key interactions within the binding pocket (FIG. 3*d*). Noteworthy is the electrostatic interaction between the ligand's carboxylate and the triarginyl cluster (Arg192, Arg424, Arg502), hydrogen bond interactions between the C7 hydroxyl group and Glu276 and the C5 isobutyramido NH and Tyr337 and Glu409. Furthermore, additional hydrophobic interactions are observed for both the C4 aromatic and C5 isobutyl functionalities, particularly with the peptide backbone, within the C4 and C5 binding domains respectively.

Chemistry

General Methods

Reagents and dry solvents were purchased from commercial sources and used without further purification. Anhydrous reactions were carried out under an atmosphere of argon in oven-dried glassware. Reactions were monitored using thin layer chromatography (TLC) on aluminium plates pre-coated with Silica Gel 60 F254 (E. Merck). Developed plates were observed under UV light at 254 nm and then visualized after application of a solution of $H_2SO_4$ in EtOH (5% v/v) followed by charring. Flash chromatography was performed on Silica Gel 60 (0.040-0.063 mm) using distilled solvents. $^1H$ and $^{13}C$ NMR spectra were recorded at 300 and 75.5 MHz respectively on a BrukerAvance 300 MHz spectrometer. Chemical shifts (δ) are reported in parts per million, relative to the residual solvent peak as internal reference [$CDCl_3$: 7.26 (s) for $^1H$, 77.0 (t) for $^{13}C$; DMSO: 2.50 (pent) for $^1H$, 39.51 (hept) for $^{13}C$; $D_2O$: 4.79 (s) for $^1H$]. 2D COSY and HSQC experiments were run to support assignments. Low-resolution mass spectra (LRMS) were recorded, in electrospray ionization mode, on a BrukerDaltonics Esquire 3000 ESI spectrometer, using positive mode. High-resolution mass spectrometry (HRMS) were recorded for either the protected or deprotected final derivatives, and were carried out by the University of Queensland FTMS Facility on a BrukerDaltonics Apex III 4.7e Fourier Transform micrOTOF-Q70 MS or by the Griffith University FTMS Facility on a BrukerDaltonics Apex III 4.7e Fourier Transform MS, fitted with an Apollo ESI source.

Final deprotected sialic acid derivatives were purified on a GracePure™ SPE C18-Aq (5000 mg/20 mL) column using 2% acetonitrile/$H_2O$ as a solvent. The purity of all synthetic intermediates after chromatographic purification was determined to be >90% by $^1H$ and $^{13}C$ NMR spectroscopy and the purity of reference compounds synthesised for screening purposes (2, 3, 5, 6), as well as the novel final products 7-10, was determined to be 295%.

Synthesis

The synthesis of intermediates 11, 12 and 17-24 and reference inhibitors 2, 3, 5, and 6 was achieved by the literature procedures. General methods are set out in Schemes 1 and 2 which allow access to all of the compounds described and synthesised herein.

General Procedure for the Synthesis of 18& 19:

A mixture of 17 or 11 (0.42 mmol), $Boc_2O$ (275 mg, 1.27 mmol) and DMAP (50 mg, 0.42 mmol) in anhydrous THF (5 mL) was stirred under argon atmosphere at 60° C. o/n. After cooling to rt, the solvent was evaporated under vacuum, and the residue was taken up in dichloromethane (DCM) for chromatographic separation on a silica gel column using ethyl acetate:hexane (1:2) as solvent to yield pure 18 (170 mg, 71%) or 19 (225 mg, 96%).

General Procedure for the Synthesis of 20 & 2:

To a methanolic solution of NaOMe, freshly prepared by dissolving sodium metal (0.39 mmol, 9 mg) in anhydrous MeOH (5 mL), was added compound 18 or 19 (0.26 mmol). The mixture was stirred at rt for 1 h and then quenched with Amberlite® IR-120 (H+) resin (to pH=5). The resin was filtered off, washed with MeOH (5 mL×3) and the combined filtrate and washings were evaporated under vacuum. The residue was re-dissolved in pyridine (2 mL), and acetic anhydride (0.5 mL) added. The reaction mixture was stirred at rt under argon atmosphere o/n and the solvent and excess $Ac_2O$ were then removed under vacuum. Finally, the residue was taken up in DCM for chromatographic separation on a silica gel column using ethyl acetate:hexane (1:2) as solvent to yield pure 20 (112 mg, 81%) or 21 (84 mg, 63%).

General Procedure for the Synthesis of 22 & 23:

To a solution of 20 or 21 (0.15 mmol) in anhydrous DCM (2 mL) was added TFA (230 μL, 3.0 mmol) and the mixture was stirred at rt under argon o/n. The reaction was diluted with DCM (20 mL) and quenched with sat. aq. $NaHCO_3$ solution (20 mL). The DCM layer was washed with water, brine then dried over anhydrous $Na_2SO_4$. The dried organic solvent was concentrated under vacuum, and purified by silica gel chromatography using the suitable solvent system to yield pure 22 (58 mg, 90%) or 23 (53 mg, 85%).

General Procedure for the Synthesis of 24 & 12:

To a solution of 22 or 23 (0.116 mmol) in DCM (2 mL) under argon was added $Et_3N$ (82 μL, 0.58 mmol) and isobutyryl chloride (18 μL, 0.17 mmol). The mixture was stirred at rt for 4 h and then loaded on a silica gel column for chromatographic separation using ethyl acetate:hexane (1:1) as solvent to yield pure 24 (50 mg, 84%) or 12 (51 mg, 91%).

General Procedure for the Synthesis of 5 & 6:

To a suspension of compound 24 or 12 (0.08 mmol) in a 1:1 mixture of $MeOH:H_2O$ (2 mL) at 0° C. was added dropwise a NaOH solution (1.0 M) until pH 14. The temperature was raised gradually to rt and the mixture was stirred at rt overnight. The solution was then acidified with Amberlite® IR-120 (H+) resin (to pH=5), filtered and washed with MeOH (10 mL) and $H_2O$ (10 mL). The combined filtrate and washings were then concentrated under vacuum and the residue was diluted with distilled water (5 mL) and adjusted to pH=8.0 using 0.05 M NaOH to convert the compound to its sodium salt. The compounds were then purified on a C18-GracePure™ cartridge using 2% acetonitrile/water as solvent to yield pure 5 (26 mg, 94%) or 6 (24 mg, 82%) as fluffy white powders.

General Procedure for the Synthesis of 13-16:

The appropriate 4-azido-4-deoxy-Neu5Ac2en derivative (11 or 12, 0.22 mmol) and the corresponding ethynyl derivative (0.33 mmol) were dissolved in a 1:1 mixture of tert-butanol:$H_2O$ (4 mL). Copper(II) sulfate pentahydrate (4 mg, 0.015 mmol) was added to the mixture followed by sodium ascorbate (0.1 mL of freshly prepared 1 M solution in $H_2O$). The mixture was stirred at 45° C. for 6 h and then left to cool to rt. The mixture was then diluted with DCM (100 mL), washed with 10% $NH_4OH$ (50 mL), followed by brine (50 mL). The organic layer was dried over anhydrous $Na_2SO_4$ and concentrated under vacuum to give the crude products 13-16, which were purified by silica gel chromatography using an appropriate solvent system.

General Procedure for the Synthesis of 7-10:

To a suspension of the protected triazole derivative 13-16 in a 1:1 mixture of $MeOH:H_2O$ (2 mL) at 0° C. was added dropwise a NaOH solution (1.0 M) until pH ~14. The temperature was gradually raised to rt and the mixture was stirred at rt overnight. The solution was then acidified with Amberlite® IR-120 (H+) resin (to pH=5), filtered and washed with MeOH (10 mL) and $H_2O$ (10 mL). The combined filtrate and washings were then concentrated under vacuum, then diluted with distilled water (5 mL) and adjusted to pH=8.0 using 0.05 M NaOH to convert the compound to its sodium salt. Finally, the compound was purified on a C18-GracePure™ cartridge using 2% acetonitrile/water as solvent to yield the pure products 7-10.

Characterisation of Synthesised Compounds

Methyl 5-acetamido-7,8,9-tri-O-acetyl-2,6-anhydro-3,4,5-trideoxy-4-(4-methoxymethyl-[1,2,3]triazol-1-yl)-D-glycero-D-galacto-non-2-enonate (13)

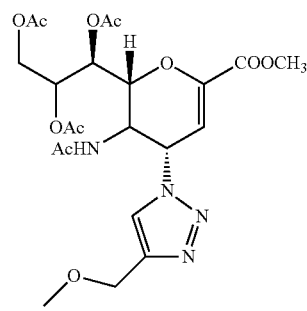

13

Purification by silica gel chromatography using ethyl acetate:acetone (6:1) yielded (90 mg, 78%) of pure 13. $^1$H NMR (300 MHz, $CDCl_3$): δ 1.81 (s, 3H, NAc), 2.05 (s, 6H, 2 OAc), 2.06 (s, 3H, OAc), 3.36 (s, 3H, $OCH_3$), 3.80 (s, 3H, $COOCH_3$), 4.17 (dd, J=12.5, 7.2 Hz, 1H, H-9), 4.29 (m, 1H, H-5), 4.50 (s, 2H, $OCH_2$), 4.68-4.79 (m, 2H, H-9', H-6), 5.40 (ddd, J=7.4, 4.9, 2.5 Hz, 1H, H-8), 5.53 (dd, J=5.1, 1.8 Hz, 1H, H-7), 5.78 (dd, J=10.0, 2.5 Hz, 1H, H-4), 6.00 (d, J=2.3 Hz, 1H, H-3), 7.05 (d, J=9.1 Hz, 1H, NH), 7.64 (s, 1H, triazole-CH); $^{13}$C NMR (75 MHz, $CDCl_3$) δ 20.71, 20.79, 20.91 (3 $OCOCH_3$), 22.80 ($NHCOCH_3$), 48.39 (C-5), 52.71 ($COOCH_3$), 58.16 ($OCH_3$), 58.38 (C-4), 62.21 (C-9), 65.68 ($OCH_2$), 67.73 (C-7), 70.90 (C-8), 76.71 (C-6), 107.18 (C-3), 121.50 (triazole-C-5), 145.24 (triazole-C-4), 145.92 (C-2), 161.27 ($COOCH_3$), 170.06, 170.27, 170.81, 170.88 ($NHCOCH_3$, 3 $OCOCH_3$). LRMS [$C_{22}H_{30}N_4O_{11}$] (m/z): (+ve ion mode) 549.1 [M+Na]+; HRMS (API) (m/z): [M+Na]+ calcd for $C_{22}H_{30}N_4NaO_{11}$ [M+Na]+549.1803. found, 549.1805.

Methyl 7,8,9-tri-O-acetyl-2,6-anhydro-3,4,5-trideoxy-5-isobutyramido-4-(4-methoxymethyl-[1,2,3,]triazol-1-yl)-D-glycero-D-galacto-non-2-enonate (15)

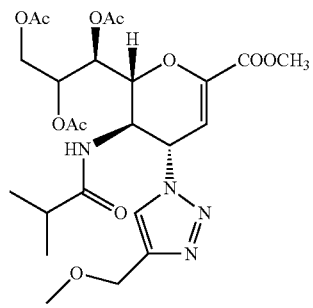

15

Purification by silica gel chromatography using ethyl acetate:acetone (9:1) yielded (65 mg, 71%) of pure 15. $^1$H NMR (300 MHz, CDCl$_3$): δ0.97 (d, J=6.9 Hz, 3H, isobut-CH$_3$), 1.01 (d, J=6.8 Hz, 3H, isobut-CH$_3$), 2.05 (s, 3H, OAc), 2.08 (s, 6H, 2 OAc), 2.24 (m, 1H, isobut-CH), 3.37 (s, 3H, OCH$_3$), 3.81 (s, 3H, COOCH$_3$), 4.14-4.29 (m, 2H, H-9, H-5), 4.51 (s, 2H, OCH$_2$), 4.68 (dd, J=12.5, 2.6 Hz, 1H, H-9'), 4.84 (dd, J=10.5, 1.7 Hz, 1H, H-6), 5.38 (ddd, J=6.6, 5.5, 2.5 Hz, 1H, H-8), 5.48 (dd, J=5.5, 1.7 Hz, 1H, H-7), 5.91 (dd, J=10.0, 2.4 Hz, 1H, H-4), 6.02 (d, J=2.4 Hz, 1H, H-3), 6.44 (d, J=8.7 Hz, 1H, NH), 7.59 (s, 1H, triazole-CH); $^{13}$C NMR (75 MHz, CDCl$_3$): δ 18.81, 19.30 (isobut-2CH$_3$), 20.74, 20.90 (3 OCOCH$_3$), 35.51 (isobut-CH), 48.79 (C-5), 52.69 (COOCH$_3$), 57.59 (C-4), 58.38 (OCH$_3$), 62.08 (C-9), 65.73 (OCH$_2$), 67.66 (C-7), 70.79 (C-8), 76.24 (C-6), 107.07 (C-3), 121.54 (triazole-C-5), 145.39 (triazole-C-4), 145.82 (C-2), 161.30 (COOCH$_3$), 170.15, 170.23, 170.69 (3 OCOCH$_3$), 177.87 (isobut-CO). LRMS [C$_{24}$H$_{34}$N$_4$O$_{11}$] (m/z): (+ve ion mode) 577.2 [M+Na]$^+$.

Methyl 7,8,9-tri-O-acetyl-2,6-anhydro-3,4,5-trideoxy-5-isobutyramido-4-(4-phenyl-[1,2,3,]triazol-1-yl)-D-glycero-D-galacto-non-2-enonate (16)

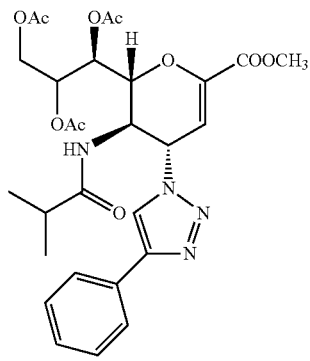

Purification by silica gel chromatography using ethyl acetate:hexane (4:1) yielded (82 mg, 84%) of pure 16. $^1$H NMR (300 MHz, CDCl$_3$): δ 0.95 (d, J=6.8 Hz, 3H, isobut-CH$_3$), 0.99 (d, J=6.9 Hz, 3H, isobut-CH$_3$), 2.06 (s, 3H, OAc), 2.09 (s, 6H, 2 OAc), 2.20-2.27 (m, 1H, isobut-CH), 3.83 (s, 3H, COOCH$_3$), 4.16-4.39 (m, 2H, H-9, H-5), 4.70 (dd, J=12.5, 2.6 Hz, 1H, H-9'), 4.88 (dd, J=10.5, 1.7 Hz, 1H, H-6), 5.40 (m, 1H, H-8), 5.52 (dd, J=5.4, 1.7 Hz, 1H, H-7), 5.99 (dd, J=10.0, 2.4 Hz, 1H, H-4), 6.08 (d, J=2.4 Hz, 1H, H-3), 6.51 (d, J=8.7 Hz, 1H, NH), 7.26-7.43 (m, 3H, Ph-H-3', Ph-H-4', Ph-H-5'), 7.74 (d, J=7.2 Hz, 2H, Ph-H-2', Ph-H-6'), 7.81 (s, 1H, triazole-CH); $^{13}$C NMR (75 MHz, CDCl$_3$): δ 18.83, 19.31 (isobut-2CH$_3$), 20.76, 20.92 (3 OCOCH$_3$), 35.55 (isobut-CH), 48.74 (C-5), 52.72 (COOCH$_3$), 57.67 (C-4), 62.12 (C-9), 67.72 (C-7), 70.84 (C-8), 76.39 (C-6), 107.25 (C-3), 118.84 (triazole-C-5), 125.83 (Ph), 128.47 (Ph), 128.89 (Ph), 129.97 (Ph q carbon), 145.81 (C-2), 148.19 (triazole-C-4), 161.35 (COOCH$_3$), 170.18, 170.26, 170.71 (3 OCOCH$_3$), 178.00 (isobut-CO). LRMS [C$_{28}$H$_{34}$N$_4$O$_{10}$] (m/z): (+ve ion mode) 608.9 [M+Na]$^+$.

Sodium 5-acetamido-2,6-anhydro-3,4,5-trideoxy-4-(4-methoxymethyl-[1,2,3,]triazol-1-yl)-D-glycero-D-galacto-non-2-enonate (7)

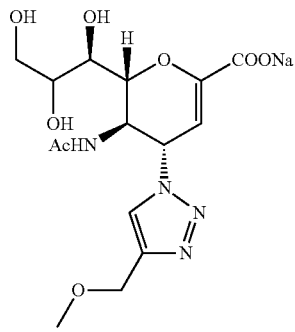

Yield=85%. $^1$H NMR (300 MHz, D$_2$O): δ 1.84 (s, 3H, NAc), 3.31 (s, 3H, OCH$_3$), 3.52-3.71 (m, 2H, H-9 & H-7), 3.85 (dd, J=11.9, 2.6 Hz, 1H, H-9'), 3.95 (ddd, J=9.3, 6.2, 2.5 Hz, 1H, H-8), 4.33 (m, 1H, H-5), 4.51 (dd, J=10.9, 1.2 Hz, 1H, H-6), 4.56 (s, 2H, OCH$_2$), 5.48 (dd, J=9.6, 2.3 Hz, 1H, H-4), 5.80 (d, J=2.2 Hz, 1H, H-3), 8.08 (s, 1H, triazole-CH); $^{13}$C NMR (75 MHz, D$_2$O): δ 21.65 (NHCOCH$_3$), 48.68 (C-5), 57.15 (OCH$_3$), 59.94 (C-4), 63.06 (C-9), 64.22 (OCH$_2$), 68.05 (C-7), 69.71 (C-8), 75.34 (C-6), 101.80 (C-3), 123.54 (triazole-C-5), 144.08 (triazole-C-4), 150.43 (C-2), 168.75 (COONa), 173.57 (NHCOCH$_3$); LRMS [C$_{15}$H$_{21}$N$_4$NaO$_8$] (m/z): (+ve ion mode) 432.1 [M+Na]$^+$.

Sodium 5-acetamido-2,6-anhydro-3,4,5-trideoxy-4-(4-phenyl-[1,2,3,]triazol-1-yl)-D-glycero-D-galacto-non-2-enonate (8)

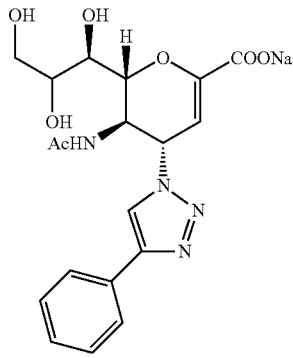

Yield=96%. $^1$H NMR (300 MHz, D$_2$O): δ 1.87 (s, 3H, NAc), 3.64 (dd, J=12.1, 6.4 Hz, 1H, H-9), 3.69 (dd, J=9.6, 1.4 Hz, 1H, H-7), 3.89 (dd, J=11.9, 2.7 Hz, 1H, H-9'), 4.00 (ddd, J=9.3, 6.3, 2.7 Hz, 1H, H-8), 4.39 (m, 1H, H-5), 4.56 (dd, J=10.8, 1.4 Hz, 1H, H-6), 5.49 (dd, J=9.7, 2.3 Hz, 1H, H-4), 5.83 (d, J=2.2 Hz, 1H, H-3), 7.40 (m, 1H, Ph-H4'), 7.46 (dd, J=8.4, 6.9 Hz, 2H, Ph-H-3', Ph-H-5'), 7.71 (d, J=7.1 Hz, 2H, Ph-H-2', Ph-H-6'), 8.28 (s, 1H, triazole-CH); $^{13}$C NMR (75 MHz, D$_2$O): δ 21.63 (NHCOCH$_3$), 48.70 (C-5), 59.96 (C-4), 63.05 (C-9), 68.03 (C-7), 69.69 (C-8), 75.31 (C-6), 101.75 (C-3), 120.41 (Ph), 125.61 (Ph), 128.77 (triazole-C-5), 129.10 (Ph), 129.28 (Ph q carbon), 147.74 (triazole-C-4), 150.48 (C-2), 168.75 (COONa), 173.58 (NHCOCH$_3$). LRMS [C$_{19}$H$_{21}$N$_4$NaO$_7$] (m/z): (+ve ion mode) 463.1 [M+Na]$^+$; HRMS (API) (m/z): [M+1]$^+$ calcd for C$_{19}$H$_{22}$N$_4$NaO$_7$ [M+H]$^+$ 441.138070. found, 441.140189.

Sodium 2,6-anhydro-3,4,5-trideoxy-5-isobutyramido-4-(4-methoxymethyl-[1,2,3,]triazol-1-yl)-D-glycero-D-galacto-non-2-enonate (9)

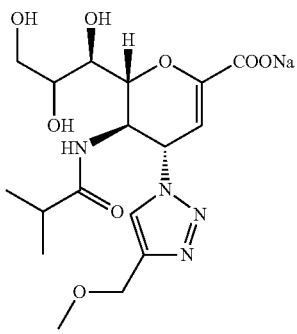

Yield=92%. $^1$H NMR (300 MHz, D$_2$O): δ 0.98 (d, J=7.0 Hz, 3H, isobut-CH$_3$), 1.03 (d, J=6.9 Hz, 3H, isobut-CH$_3$), 2.46 (m, 1H, isobut-CH), 3.39 (s, 3H, OCH$_3$), 3.65-3.76 (m, 2H, H-9, H-7), 3.94 (dd, J=11.9, 2.7 Hz, 1H, H-9'), 4.04 (ddd, J=9.3, 6.3, 2.6 Hz, 1H, H-8), 4.49 (m, 1H, H-5), 4.60-4.65 (m, 3H, H-6, OCH$_2$), 5.61 (dd, J=9.7, 2.3 Hz, 1H, H-4), 5.87 (d, J=2.2 Hz, 1H, H-3), 8.18 (s, 1H, triazole-CH); $^{13}$C NMR (75 MHz, D$_2$O): δ 18.43 (isobut-CH$_3$), 18.64 (isobut-CH$_3$), 35.10 (isobut-CH), 48.19 (C-5), 57.24 (OCH$_3$), 59.86 (C-4), 63.07 (C-9), 64.24 (OCH$_2$), 68.13 (C-7), 69.82 (C-8), 75.43 (C-6), 102.02 (C-3), 123.65 (triazole-C-5), 144.07 (triazole-C-4), 150.30 (C-2), 168.81 (COONa), 180.66 (isobut-CO). LRMS [C$_{17}$H$_{25}$N$_4$NaO$_8$] (m/z): (+ve ion mode) 459.0 [M+Na]$^+$; HRMS (API) (m/z): [M+Na]$^+$ calcd for C$_{17}$H$_{25}$N$_4$Na$_2$O$_8$[M+Na]$^+$459.1462. found, 459.1458.

Sodium 2,6-anhydro-3,4,5-trideoxy-5-isobutyramido-4-(4-phenyl-[1,2,3,]triazol-1-yl)-D-glycero-D-galacto-non-2-enonate (10)

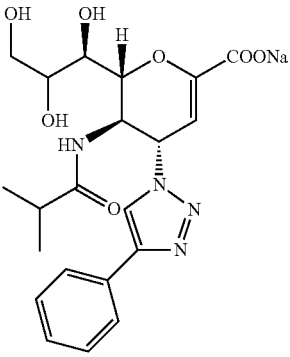

Yield=89%. $^1$H NMR (300 MHz, D$_2$O): δ 0.94 (d, J=6.9 Hz, 3H, isobut-CH$_3$), 0.99 (d, J=6.9 Hz, 3H, isobut-CH$_3$), 2.43 (m, 1H, isobut-CH), 3.60-3.76 (m, 2H, H-9, H-7), 3.93 (dd, J=12.0, 2.7 Hz, 1H, H-9'), 4.04 (ddd, J=9.2, 6.3, 2.6 Hz, 1H, H-8), 4.51 (m, 1H, H-5), 4.62 (d, J=11.0 Hz, 1H, H6), 5.58 (dd, J=9.7, 2.3 Hz, 1H, H-4), 5.88 (d, J=2.2 Hz, 1H, H-3), 7.42-7.54 (m, 3H, Ph-H-3', Ph-H-4', Ph-H-5'), 7.78 (d, J=7.1 Hz, 2H, Ph-H-2', Ph-H-6'), 8.36 (s, 1H, triazole-CH); $^{13}$C NMR (75 MHz, D$_2$O): δ 18.38 (isobut-CH$_3$), 18.65 (isobut-CH$_3$), 35.10 (isobut-CH), 48.23 (C-5), 59.91 (C-4), 63.07 (C-9), 68.15 (C-7), 69.76 (C-8), 75.41 (C-6), 101.96 (C-3), 120.66 (Ph), 125.67 (Ph), 128.81 (triazole-C-5), 129.16 (Ph), 129.36 (Ph q carbon), 147.71 (triazole-C-4), 150.32 (C-2), 168.80 (COONa), 180.67 (isobut-CO). LRMS [C$_{21}$H$_{25}$N$_4$NaO$_7$] (m/z): (+ve ion mode) 491.2 [M+Na]$^+$; HRMS (API) (m/z): [M+Na]$^+$ calcd for C$_{21}$H$_{25}$N$_4$Na$_2$O$_7$ [M+Na]$^+$491.1513. found, 491.1515.

Methyl 5-acetamido-7,8,9-tri-O-acetyl-2,6-anhydro-3,4,5-trideoxy-4-(4-isobutyl-[1,2,3,]triazol-1-yl)-D-glycero-D-galacto-non-2-enonate (IE832-6)

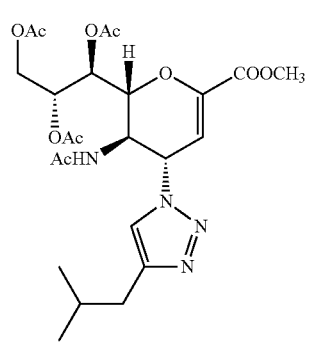

Purification by silica gel chromatography using ethylacetate yielded (93 mg, 66%) of pure IE832-6. $^1$H NMR (300 MHz, CDCl$_3$): δ 0.89 (d, J=6.6 Hz, 6H, isobutyl-2CH$_3$), 1.81 (s, 3H, NAc), 1.93 (m, 1H, isobutyl-CH), 2.06 (s, 6H, 2 OAc), 2.09 (s, 3H, OAc), 2.58 (d, J=6.9 Hz, 2H, isobutyl-CH$_2$), 3.82 (s, 3H, COOCH$_3$), 4.17 (dd, J=12.5, 6.7 Hz, 1H, H-9), 4.38 (m, 1H, H-5), 4.67 (dd, J=12.4, 2.3 Hz, 1H, H-9'), 4.77 (d, J=10.5 Hz, 1H, H-6), 5.40 (m, 1H, H-8), 5.55 (d, J=5.4 Hz, 1H, H-7), 5.88 (d, J=9.9 Hz, 1H, H-4), 6.03 (s, 1H, H-3), 7.07 (brs, 1H, NH), 7.49 (s, 1H, triazole-CH); $^{13}$H NMR (75 MHz, CDCl$_3$): δ 20.74, 20.81, 20.93 (3 OCOCH$_3$), 22.12, 22.84 (2 isobutyl-CH$_3$+NHCOCH$_3$), 28.60 (isobutyl-CH), 34.17 (isobutyl-CH$_2$), 48.04 (C-5), 52.76 (COOCH$_3$), 58.62 (C-4), 62.06 (C-9), 67.56 (C-7), 70.55 (C-8), 76.57 (C-6), 106.82 (C-3), 120.94 (triazole-C-5), 146.03 (C-2), 146.83 (triazole-C-4), 161.30 (COOCH$_3$), 169.99, 170.00 170.13, 170.78 (NHCOCH$_3$, 3 OCOCH$_3$). LRMS [C$_{24}$H$_{34}$N$_4$O$_{10}$] (m/z): (+ve ion mode) 561.2 [M+Na]$^+$.

Sodium 5-acetamido-2,6-anhydro-3,4,5-trideoxy-4-(4-isobutyl-[1,2,3,]triazol-1-yl)-D-glycero-D-galacto-non-2-enonate (IE832-8)

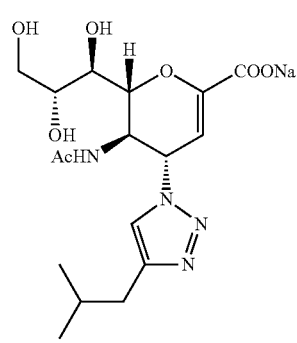

Yield=79%. ¹H NMR (300 MHz, D₂O): δ 0.82 (d, J=6.6 Hz, 6H, isobutyl-2CH₃), 1.81-1.86 (m, 4H, NAc & isobutyl-CH), 2.53 (d, J=6.9 Hz, 2H, isobutyl-CH₂), 3.54-3.68 (m, 2H, H-9 & H-7), 3.85 (dd, J=11.9, 2.6 Hz, 1H, H9'), 3.94 (ddd, J=9.3, 6.3, 2.5 Hz, 1H, H-8), 4.33 (m, 1H, H-5), 4.49 (dd, J=10.9, 1.2 Hz, 1H, H-6), 5.40 (dd, J=9.7, 2.2 Hz, 1H, H-4), 5.78 (d, J=2.2 Hz, 1H, H-3), 7.80 (s, 1H, triazole-CH); ¹³C NMR (75 MHz, D₂O): δ 21.15 (isobutyl-2CH₃), 21.54 (NHCOCH₃), 28.09 (isobutyl-CH), 33.42 (isobutyl-CH₂), 48.53 (C-5), 59.65 (C-4), 62.99 (C-9), 67.98 (C-7), 69.63 (C-8), 75.29 (C-6), 102.06 (C-3), 122.01 (triazole-C-5), 147.74 (triazole-C-4), 150.12 (C-2), 168.81 (COONa), 173.28 (NHCOCH₃). LRMS [C₁₇H₂₅N₄NaO₇] (m/z): (+ve ion mode) 443.1 [M+Na]⁺; HRMS (API) (m/z): [M+1]⁺ calcd for C₁₇H₂₆N₄NaO₇ [M+1]⁺421.169370. found, 421.170091.

Methyl 5-acetamido-7,8,9-tri-O-acetyl-2,6-anhydro-3,4,5-trideoxy-4-(4-(4-hydroxymethyl phenyl)-[1,2,3,]triazol-1-yl)-D-glycero-D-galacto-non-2-enonate (IE932-10)

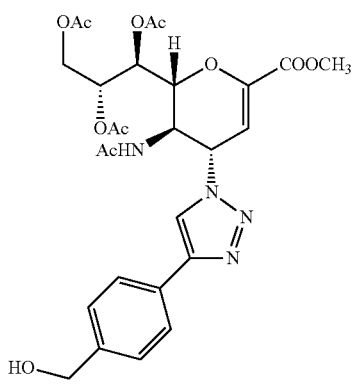

IE932-10

¹H NMR (300 MHz, CDCl₃): ¹H NMR (300 MHz, Chloroform-d) δ 1.86 (s, 3H, NAc), 2.07 (s, 3H, OAc), 2.09 (s, 3H, OAc), 2.10 (s, 3H, OAc), 3.84 (s, 3H, COOCH₃), 4.19 (dd, J=12.5, 6.6 Hz, 1H, H-9), 4.31 (m, 1H, H-5), 4.60-4.74 (m, 3H, H-9', CH₂), 4.80 (d, J=10.4 Hz, 1H, H-6), 5.40 (m, 1H, H-8), 5.54 (dd, J=5.8, 1.7 Hz, 1H, H-7), 5.93 (d, J=10.1 Hz, 1H, H-4), 6.07 (d, J=2.2 Hz, 1H, H-3), 6.74 (brs, 1H, NH), 7.38 (d, J=7.9 Hz, 2H, Ph-H-3', Ph-H-5'), 7.74 (d, J=7.7 Hz, 2H, Ph-H-2', Ph-H-6'), 7.96 (s, 1H, triazole-CH); ¹³H NMR (75 MHz, CDCl₃): δ 20.74, 20.85, 20.98 (3 OCOCH₃), 22.90 (NHCOCH₃), 48.31 (C-5), 52.83 (COOCH₃), 58.49 (C-4), 62.19 (C-9), 64.66 (CH₂), 67.72 (C-7), 70.93 (C-8), 76.78 (C-6), 107.12 (C-3), 119.00 (triazole-C-5), 125.91 (Ph), 127.47 (Ph), 128.61 (Ph q carbon), 141.59 (Ph q carbon), 146.01 (C-2), 147.65 (triazole-C-4), 161.37 (COOCH₃), 170.13, 170.41, 170.92, 171.26 (NHCOCH₃, 3 OCOCH₃). LRMS [C₂₇H₃₂N₄O₁₁] (m/z): (+ve ion mode) 611.2 [M+Na]⁺.

Sodium 5-acetamido-2,6-anhydro-3,4,5-trideoxy-4-(4-(4-hydroxymethyl phenyl)-[1,2,3,]triazol-1-yl)-D-glycero-D-galacto-non-2-enonate (IE832-12)

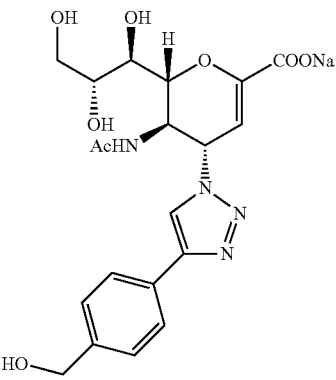

IE832-12

¹H NMR (300 MHz, D₂O): δ 1.85 (s, 3H, NAc), 3.54-3.71 (m, 2H, H-9, H-7), 3.86 (dd, J=11.9, 2.5 Hz, 1H, H-9'), 3.96 (ddd, J=9.3, 6.3, 2.4 Hz, 1H, H-8), 4.37 (m, 1H, H-5), 4.54 (d, J=10.9 Hz, 1H, H-6), 4.62 (s, 2H, CH₂), 5.50 (dd, J=9.6, 2.1 Hz, 1H, H-4), 5.83 (d, J=2.1 Hz, 1H, H-3), 7.44 (d, J=8.2 Hz, 2H, Ph-H-3', Ph-H-5'), 7.75 (d, J=8.2 Hz, 2H, Ph-H-2', Ph-H-6'), 8.38 (s, 1H, triazole-CH); ¹³C NMR (75 MHz, D₂O): δ 21.70 (NHCOCH₃), 48.78 (C-5), 60.04 (C-4), 63.12 (C-9), 63.55 (CH₂), 68.11 (C-7), 69.77 (C-8), 75.39 (C-6), 101.78 (C-3), 120.53 (triazole-C-5), 125.90 (Ph), 128.06 (Ph), 128.77 (Ph q carbon), 140.80 (Ph q carbon), 147.60 (C-2), 150.57 (triazole-C-4), 168.77 (COONa), 173.66 (NHCOCH₃). LRMS [C₂₀H₂₃N₄NaO₈] (m/z): (+ve ion mode) 493.1 [M+Na]⁺; HRMS (API) (m/z): [M+1]⁺ calcd for C₂₀H₂₄N₄NaO₈ [M+1]⁺471.148635. found, 471.147973.

Methyl 5-acetamido-7,8,9-tri-O-acetyl-2,6-anhydro-3,4,5-trideoxy-4-(4-methoxymethyl-[1,2,3,]triazol-1-yl)-D-glycero-D-galacto-non-2-enonate (IE832-13)

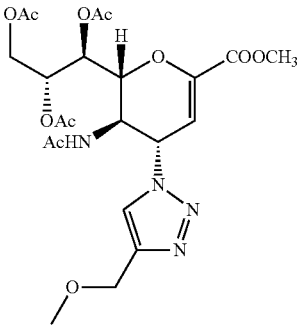

IE832-13

Purification by silica gel chromatography using ethylacetate: acetone (6:1) yielded (67 mg, 58%) of pure IE832-13. ¹H NMR (300 MHz, CDCl₃): δ 1.81 (S, 3H, NAc), 2.05 (s, 6H, 2 OAc), 2.06 (s, 3H, OAc), 3.36 (s, 3H, OCH₃), 3.80 (s, 3H, COOCH₃), 4.17 (dd, J=12.5, 7.2 Hz, 1H, H-9), 4.29 (m, 1H, H-5), 4.50 (s, 2H, OCH₂), 4.68-4.79 (m, 2H, H-9', H-6), 5.40 (ddd, J=7.4, 4.9, 2.5 Hz, 1H, H-8), 5.53 (dd, J=5.1, 1.8 Hz, 1H, H-7), 5.78 (dd, J=10.0, 2.5 Hz, 1H, H-4), 6.00 (d, J=2.3 Hz, 1H, H-3), 7.05 (d, J=9.1 Hz, 1H, NH), 7.64 (s, 1H, triazole-CH); ¹³C NMR (75 MHz, CDCl₃) δ 20.71, 20.79, 20.91 (3 OCOCH₃), 22.80 (NHCOCH₃), 48.39 (C-5), 52.71 (COOCH₃), 58.16 (OCH₃), 58.38 (C-4), 62.21 (C-9), 65.68 (OCH₂), 67.73 (C-7), 70.90 (C-8), 76.71 (C-6), 107.18 (C-3), 121.50 (triazole-C-5), 145.24 (triazole-C-4), 145.92 (C-2), 161.27 (COOCH₃), 170.06, 170.27, 170.81, 170.88 (NHCOCH₃, 3 OCOCH₃). LRMS [C₂₂H₃₀N₄O₁₁](m/z):

Sodium 5-acetamido-2,6-anhydro-3,4,5-trideoxy-4-(4-methoxymethyl-[1,2,3,]triazol-1-yl)-D-glycero-D-galacto-non-2-enonate (IE832-17)

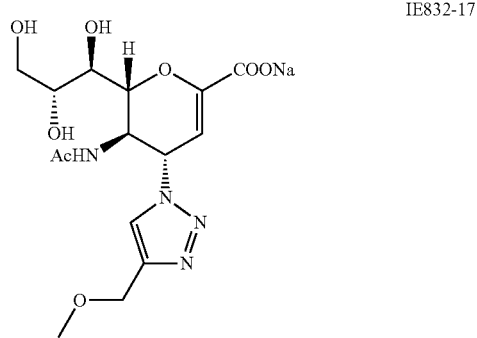

Yield=85%. ¹H NMR (300 MHz, D₂O): δ 1.84 (s, 3H, NAc), 3.31 (s, 3H, OCH₃), 3.52-3.71 (m, 2H, H-9 & H-7), 3.85 (dd, J=11.9, 2.6 Hz, 1H, H-9'), 3.95 (ddd, J=9.3, 6.2, 2.5 Hz, 1H, H-8), 4.33 (m, 1H, H-5), 4.51 (dd, J=10.9, 1.2 Hz, 1H, H-6), 4.56 (s, 2H, OCH₂), 5.48 (dd, J=9.6, 2.3 Hz, 1H, H-4), 5.80 (d, J=2.2 Hz, 1H, H-3), 8.08 (s, 1H, triazole-CH); ¹³C NMR (75 MHz, D₂O): δ 21.65 (NHCOCH₃), 48.68 (C-5), 57.15 (OCH₃), 59.94 (C-4), 63.06 (C-9), 64.22 (OCH₂), 68.05 (C-7), 69.71 (C-8), 75.34 (C-6), 101.80 (C-3), 123.54 (triazole-C-5), 144.08 (C-2), 150.43 (triazole-C-4), 168.75 (COONa), 173.57 (NHCOCH₃); LRMS [C₁₅H₂₁N₄NaO₈] (m/z): (+ve ion mode) 432.1 [M+Na]⁺.

Methyl 5-acetamido-7,8,9-tri-O-acetyl-2,6-anhydro-3,4,5-trideoxy-4-(4-(3-methoxyphenyl)-[1,2,3,]triazol-1-yl)-D-glycero-D-galacto-non-2-enonate (IE832-18)

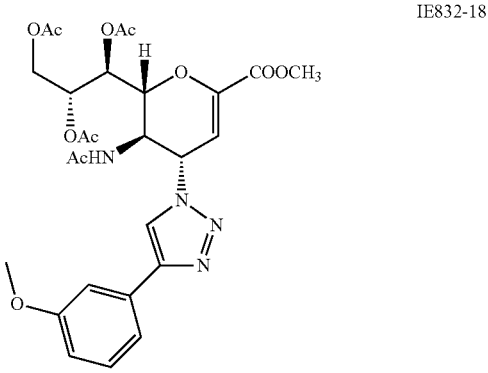 [SMILES: COC(=O)C1=C[C@H](n2cc(-c3cccc(OC)c3)nn2)[C@@H](NC(C)=O)[C@H]([C@H](OC(C)=O)[C@@H](COC(C)=O)OC(C)=O)O1]

¹H NMR (300 MHz, CDCl₃): δ 1.84 (s, 3H, NAc), 2.05 (s, 3H, OAc), 2.06 (s, 3H, OAc), 2.08 (s, 3H, OAc), 3.83 (s, 3H, COOCH₃), 3.84 (s, 3H, OCH₃), 4.20 (dd, J=12.5, 7.0 Hz, 1H, H-9), 4.32 (m, 1H, H-5), 4.71 (dd, J=12.5, 2.7 Hz, 1H, H9'), 4.83 (dd, J=10.5, 1.9 Hz, 1H, H-6), 5.43 (ddd, J=6.9, 5.4, 2.6 Hz, 1H, H-8), 5.57 (dd, J=5.4, 1.9 Hz, 1H, H-7), 5.87 (dd, J=10.0, 2.5 Hz, 1H, H-4), 6.05 (d, J=2.4 Hz, 1H, H-3), 6.79-6.92 (m, 2H, NH, Ph-H-4'), 7.23-7.38 (m, 3H, Ph-H-2', Ph-H-5', Ph-H-6'), 7.84 (s, 1H, triazole-CH); ¹³C NMR (75 MHz, CDCl₃) δ 20.73, 20.79, 20.92 (3 OCOCH₃), 22.98 (NHCOCH₃), 48.79 (C-5), 52.74 (COOCH₃), 55.35 (Ar—OCH₃), 58.04 (C-4), 62.18 (C-9), 67.74 (C-7), 70.78 (C-8), 76.63 (C-6), 107.19 (C-3), 110.94 (Ph), 114.43 (Ph), 118.20 (Ph), 118.93 (triazole-C-5), 129.97 (Ph), 131.17 (Ph q carbon), 146.02 (C2), 148.03 (triazole-C-4), 160.02 (Ph q carbon), 161.31 (COOCH₃), 170.12, 170.24, 170.81, 170.99 (NHCOCH₃, 3 OCOCH₃). LRMS [C₂₇H₃₂N₄O₁₁] (m/z): (+ve ion mode) 611.2 [M+Na]⁺.

Sodium 5-acetamido-2,6-anhydro-3,4,5-trideoxy-4-(4-(3-methoxyphenyl)-[1,2,3,]triazol-1-yl)-D-glycero-D-galacto-non-2-enonate (IE832-20)

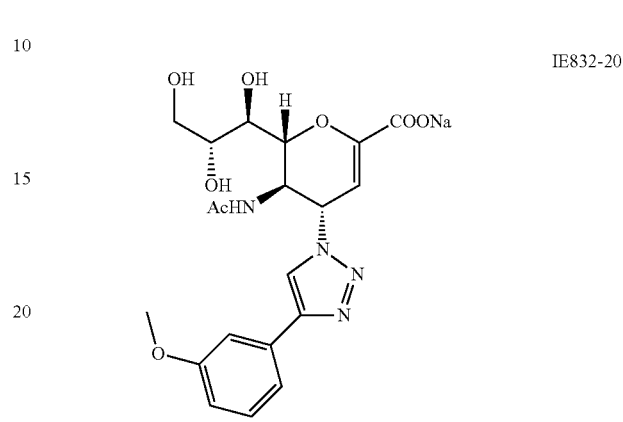

¹H NMR (300 MHz, D₂O): δ 1.86 (s, 3H, NAc), 3.52-3.74 (m, 2H, H-9, H-7), 3.77-3.92 (m, 4H, OCH₃, H-9'), 3.97 (m, 1H, H-8), 4.37 (m, 1H, H-5), 4.54 (d, J=10.9 Hz, 1H, H-6), 5.49 (dd, J=9.6, 2.4 Hz, 1H, H-4), 5.84 (s, 1H, H-3), 6.96 (m, 1H, Ph-H-4'), 7.23-7.48 (m, 3H, Ph-H-2', Ph-H-5', Ph-H-6'), 8.35 (s, 1H, triazole-CH); ¹³C NMR (75 MHz, D₂O): δ 21.71 (NHCOCH₃), 48.80 (C-5), 55.39 (OCH₃), 60.03 (C-4), 63.12 (C-9), 68.11 (C-7), 69.77 (C-8), 75.39 (C-6), 101.73 (C-3), 110.89 (Ph), 114.54 (Ph), 118.49 (Ph), 120.66 (triazole-C-5), 130.49 (Ph), 130.85 (Ph q carbon), 147.51 (C2), 150.62 (triazole-C-4), 159.29 (Ph q carbon), 168.77 (COONa), 173.65 (NHCOCH₃). LRMS [C₂₀H₂₃N₄NaO₈] (m/z): (+ve ion mode) 493.0 [M+1]⁺; HRMS (API) (m/z): [M+1] calcd for C₂₀H₂₄N₄NaO₈ [M+1]⁺471.148635. found, 471.148177.

Methyl 5-acetamido-7,8,9-tri-O-acetyl-2,6-anhydro-3,4,5-trideoxy-4-(4-propyl-[1,2,3,]triazol-1-yl)-D-glycero-D-galacto-non-2-enonate (IE832-24)

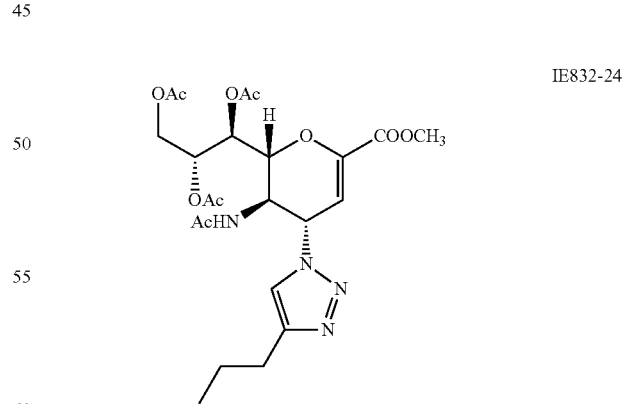

¹H NMR (300 MHz, CDCl₃): δ 0.97 (t, J=7.3 Hz, 3H, propyl-CH₃), 1.73 (m, 2H, propyl-2'-CH₂), 1.83 (s, 3H, NAc), 2.07 (s, 6H, 2 OAc), 2.10 (s, 3H, OAc), 2.77 (t, J=7.6 Hz, 2H, propyl-1'-CH₂), 3.83 (s, 3H, COOCH₃), 4.16 (dd, J=12.5, 6.0 Hz, 1H, H-9), 4.38 (m, 1H, H-5), 4.58 (dd, J=12.6, 2.6 Hz, 1H, H-9'), 4.85 (d, J=10.6 Hz, 1H, H-6), 5.42

(m, 1H, H-8), 5.56 (d, J=6.5 Hz, 1H, H-7), 6.01 (s, 1H, H-3), 6.11 (d, J=10.1 Hz, 1H, H-4), 7.37 (brs, 1H, NH), 7.68 (s, 1H, triazole-CH); LRMS [C₂₃H₃₂N₄O₁₀] (m/z): (+ve ion mode) 547.2 [M+Na]⁺

Sodium 5-acetamido-2,6-anhydro-3,4,5-trideoxy-4-(4-propyl-[1,2,3,]triazol-1-yl)-D-glycero-D-galacto-non-2-enonate (IE832-26)

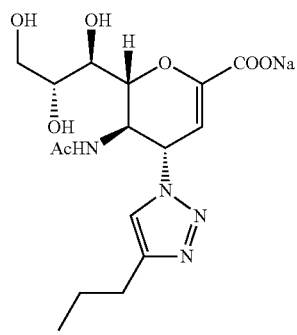

IE832-26

¹H NMR (300 MHz, D₂O): δ 0.92 (t, J=7.4 Hz, 3H, propyl-CH₃), 1.57-1.76 (m, 2H, propyl-2'-CH₂), 1.93 (s, 3H, NAc), 2.71 (t, J=7.3 Hz, 2H, propyl-1'-CH₂), 3.62-3.77 (m, 2H, H-9, H-7), 3.94 (dd, J=11.9, 2.7 Hz, 1H, H-9'), 4.04 (ddd, J=9.2, 6.3, 2.7 Hz, 1H, H-8), 4.41 (m, 1H, H-5), 4.58 (dd, J=10.9, 1.3 Hz, 1H, H-6), 5.50 (dd, J=9.7, 2.3 Hz, 1H, H-4), 5.87 (d, J=2.3 Hz, 1H, H-3), 7.89 (s, 1H, triazole-CH). LRMS [C₁₆H₂₃N₄NaO₇] (m/z): (+ve ion mode) 429.0 [M+Na]⁺; HRMS (API) (m/z): [M+Na]⁺ calcd for C₁₆H₂₃N₄Na₂O₇[M+1]⁺429.1357. found, 429.1361.

Methyl 5-acetamido-7,8,9-tri-O-acetyl-2,6-anhydro-3,4,5-trideoxy-4-(4-(pyridin-3-yl)-[1,2,3,]triazol-1-yl)-D-glycero-D-galacto-non-2-enonate (IE832-25)

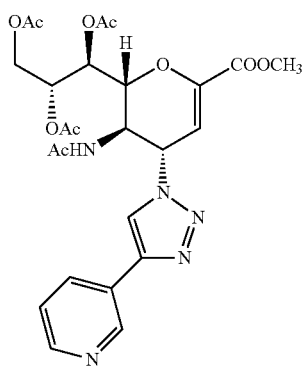

IE832-25

¹H NMR (300 MHz, CDCl₃): δ 1.82 (s, 3H, NAc), 2.06 (s, 6H, 2 OAc), 2.08 (s, 3H, OAc), 3.82 (s, 3H, COOCH₃), 4.19 (dd, J=12.5, 7.2 Hz, 1H, H-9), 4.40 (q, J=9.9 Hz, 1H, H-5), 4.64-4.88 (m, 2H, H-7, H-9'), 5.38 (m, 1H, H-8), 5.57 (dd, J=4.8, 1.9 Hz, 1H, H-7), 5.86 (dd, J=9.9, 2.4 Hz, 1H, H-4), 6.08 (d, J=2.4 Hz, 1H, H-3), 7.08 (d, J=9.1 Hz, 1H, NH), 7.36 (dd, J=7.9, 4.8 Hz, 1H, Pyr-H5'), 8.04 (s, 1H, triazole-CH), 8.14 (d, J=7.8 Hz, 1H, Pyr-H4'), 8.54 (d, J=4.8 Hz, 1H, Pyr-H-6'), 8.96 (s, 1H, Pyr-H-2'); ¹³C NMR (75 MHz, CDCl₃) δ 20.69, 20.79, 20.94 (3 OCOCH₃), 22.89 (NHCOCH₃), 48.35 (C-5), 52.81 (COOCH₃), 58.57 (C-4), 62.14 (C-9), 67.77 (C-7), 71.17 (C-8), 76.85 (C-6), 106.88 (C-3), 119.07 (triazole-C-5), 123.89 (Pyr), 126.33 (Pyr q carbon), 133.20 (Pyr), 145.13 (triazole-C-4), 146.17 (C2), 146.88 (Pyr), 149.31 (Pyr), 161.25 (COOCH₃), 170.16, 170.49, 170.80, 170.95 (NHCOCH₃, 3 OCOCH₃); LRMS [C₂₅H₂₉N₅O₁₀] (m/z): (+ve ion mode) 582.2 [M+Na]⁺.

Sodium 5-acetamido-2,6-anhydro-3,4,5-trideoxy-4-(4-(pyridin-3-yl)-[1,2,3,]triazol-1-yl)-D-glycero-D-galacto-non-2-enonate (IE832-27)

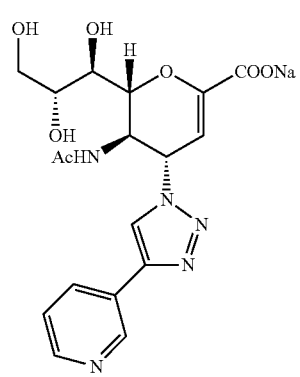

IE832-27

¹H NMR (300 MHz, D₂O): δ 1.92 (s, 3H, NAc), 3.62-3.78 (m, 2H, H-9, H-7), 3.93 (dd, J=11.9, 2.7 Hz, 1H, H-9'), 4.04 (ddd, J=9.3, 6.3, 2.6 Hz, 1H, H-8), 4.44 (m, 1H, H-5), 4.61 (dd, J=10.9, 1.3 Hz, 1H, H-6), 5.59 (dd, J=9.6, 2.3 Hz, 1H, H-4), 5.90 (d, J=2.3 Hz, 1H, H-3), 7.53 (m, 1H, Pyr-H-5'), 8.17 (d, J=8.0 Hz, 1H, Pyr-H-4'), 8.49-8.60 (m, 2H, triazole-CH, Phyr-H-6'), 8.87 (brs, 1H, Pyr-H-2'); ¹³C NMR (75 MHz, D₂O): δ 21.67 (NHCOCH₃), 48.77 (C-5), 60.17 (C-4), 63.08 (C-9), 68.06 (C-7), 69.73 (C-8), 75.36 (C-6), 101.61 (C-3), 121.13 (triazole-C-5), 134.31 (Pyr), 144.68 (C-2), 145.64 (Pyr), 148.42 (Pyr), 150.65 (triazole-C-4), 168.72 (COONa), 173.65 (NHCOCH₃). LRMS [C₁₈H₂₀N₅NaO₇] (m/z): (+ve ion mode) 463.7 [M+1]⁺; HRMS (API) (m/z): [M+1]⁺ calcd for C₁₈H₂₁N₅NaO₇ [M+1]⁺442.133319. found, 442.133358.

Methyl 5-acetamido-7,8,9-tri-O-acetyl-2,6-anhydro-3,4,5-trideoxy-4-(4-(4-methoxyphenyl)-[1,2,3,]triazol-1-yl)-D-glycero-D-galacto-non-2-enonate (IE832-29)

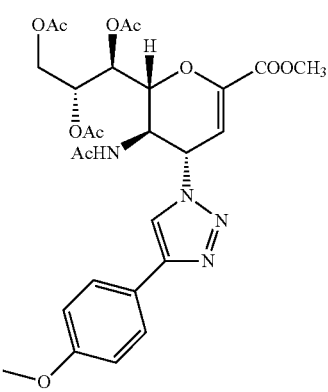

IE832-29

¹H NMR (300 MHz, CDCl₃): δ 1.88 (s, 3H, NAc), 2.06 (s, 3H, OAc), 2.10 (s, 6H, 2 OAc), 3.83 (s, 3H, COOCH₃), 3.84 (s, 3H, OCH₃), 4.13-4.30 (m, 2H, H-9, H-5), 4.66 (dd, J=12.5, 2.6 Hz, 1H, H-9'), 4.83 (dd, J=10.6, 1.9 Hz, 1H, H-6), 5.41 (m, 1H, H-8), 5.52 (dd, J=5.8, 1.8 Hz, 1H, H-7), 5.93 (dd, J=10.0, 2.5 Hz, 1H, H-4), 6.01-6.16 (m, 2H, H-3, NH), 6.94 (d, J=8.6 Hz, 2H, Ph-H-3', Ph-H-5'), 7.61-7.83 (m, 3H, triazole-CH, Ph-H-2', Ph-H-6'); ¹³C NMR (75 MHz, CDCl₃) δ 20.71, 20.78, 20.90 (3 OCOCH₃), 22.90 (NHCOCH₃), 48.45 (C-5), 52.70 (COOCH₃), 55.31 (Ph-OCH₃), 58.17 (C-4), 62.23 (C-9), 67.80 (C-7), 70.92 (C-8), 76.83 (C-6), 107.40 (C-3), 114.32 (Ph), 117.88 (triazole-C-5), 122.57 (Ph q carbon), 127.13 (Ph), 145.93 (C-2), 148.07 (triazole-C-4), 159.87 (Ph q carbon), 161.33 (COOCH₃), 170.10, 170.27, 170.81, 170.99 (NHCOCH₃, 3 OCOCH₃). LRMS [C₂₇H₃₂N₄O₁₁] (m/z): (+ve ion mode) 611.3 [M+Na]⁺.

Sodium 5-acetamido-2,6-anhydro-3,4,5-trideoxy-4-(4-(4-methoxyphenyl)-[1,2,3,]triazol-1-yl)-D-glycero-D-galacto-non-2-enonate (IE832-31)

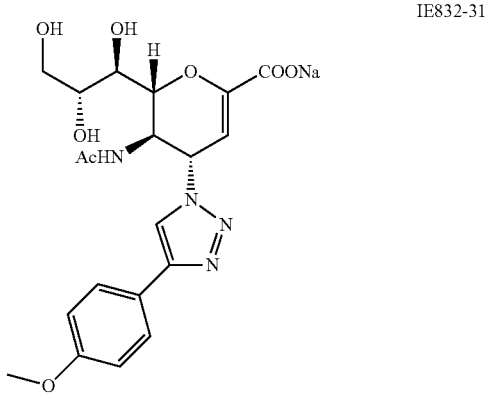

¹H NMR (300 MHz, D₂O): δ 1.92 (s, 3H, NAc), 3.63-3.77 (m, 2H, H-9, H-7), 3.85 (s, 3H, OCH₃), 3.93 (dd, J=11.9, 2.7 Hz, 1H, H-9'), 4.03 (ddd, J=9.6, 6.3, 2.6 Hz, 1H, H-8), 4.42 (m, 1H, H-5), 4.59 (dd, J=10.9, 1.3 Hz, 1H, H-6), 5.52 (dd, J=9.6, 2.3 Hz, 1H, H-4), 5.87 (d, J=2.2 Hz, 1H, H-3), 7.05 (d, J=9.0 Hz, 2H, Ph-H-3', Ph-H-5'), 7.68 (d, J=9.0 Hz, 1H, Ph-H-2', Ph-H-6'), 8.26 (s, 1H, triazole-CH); ¹³C NMR (75 MHz, D₂O): δ 21.65 (NHCOCH₃), 48.75 (C-5), 55.39 (OCH₃), 60.01 (C-4), 63.08 (C-9), 68.07 (C-7), 69.72 (C-8), 75.35 (C-6), 101.82 (C-3), 114.60 (Ph), 119.78 (triazole-C-5), 122.49 (Ph q carbon), 127.21 (Ph), 147.65 (C-2), 150.49 (triazole-C-4), 159.23 (Ph q carbon), 168.78 (COONa), 173.62 (NHCOCH₃). LRMS [C₂₀H₂₃N₄NaO₈] (m/z): (+ve ion mode) 492.6 [M+1]⁺; HRMS (API) (m/z): [M+1]⁺ calcd for C₂₀H₂₄N₄NaO₈ [M+1]⁺471.148635. found, 471.147452.

Methyl 5-acetamido-7,8,9-tri-O-acetyl-2,6-anhydro-3,4,5-trideoxy-4-(4-(2-methoxyphenyl)-[1,2,3,]triazol-1-yl)-D-glycero-D-galacto-non-2-enonate (IE832-30)

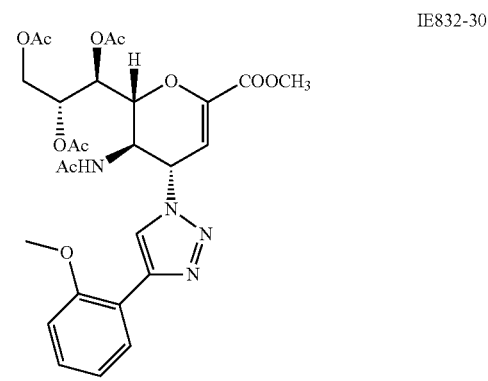 [SMILES: COC(=O)C1=C[C@H](n2cc(-c3ccccc3OC)nn2)[C@@H](NC(C)=O)[C@H]([C@H](OC(C)=O)[C@@H](COC(C)=O)OC(C)=O)O1]

Purification by silica gel chromatography using ethylacetate: hexane (7:1) yielded (81 mg, 62%) of pure IE832-30. ¹H NMR (300 MHz, CDCl₃): δ 1.84 (s, 3H, NAc), 2.05 (s, 3H, OAc), 2.06 (s, 3H, OAc), 2.08 (s, 3H, OAc), 3.83 (s, 3H, COOCH₃), 3.88 (s, 3H, OCH₃), 4.20 (dd, J=12.4, 7.0 Hz, 1H, H-9), 4.37 (m, 1H, H-5), 4.71 (dd, J=12.4, 2.7 Hz, 1H, H-9'), 4.89 (dd, J=10.5, 1.9 Hz, 1H, H-6), 5.45 (m, 1H, H-8), 5.59 (dd, J=5.4, 1.9 Hz, 1H, H-7), 5.87 (dd, J=9.9, 2.5 Hz, 1H, H-4), 6.07 (d, J=2.4 Hz, 1H, H-3), 6.91 (d, J=8.3 Hz, 1H, Ph-H-3'), 7.03 (m, 1H, Ph-H-5'), 7.22-7.30 (m, 2H, Ph-H-4', NH), 8.07 (s, 1H, triazole-CH), 8.17 (dd, J=7.8, 1.8 Hz, 1H, Ph-H-6'); ¹³C NMR (75 MHz, CDCl₃) b 20.71, 20.76, 20.88 (3 OCOCH₃), 22.90 (NHCOCH₃), 48.84 (C-5), 52.64 (COOCH₃), 55.36 (Ph-OCH₃), 57.83 (C-4), 62.24 (C-9), 67.85 (C-7), 70.79 (C-8), 76.75 (C-6), 107.72 (C-3), 110.87 (Ph), 118.66 (Ph q carbon), 120.88 (Ph), 122.32 (triazole-C-5), 127.37 (Ph), 129.24 (Ph), 143.40 (triazole-C4), 145.82 (C-2), 155.68 (Ph q carbon), 161.44 (COOCH₃), 170.06, 170.19, 170.75, 171.04 (NHCOCH₃, 3 OCOCH₃). LRMS [C₂₇H₃₂N₄O₁₁] (m/z): (+ve ion mode) 611.2 [M+Na]⁺; HRMS (API) (m/z): [M+Na]⁺ calcd for C₂₇H₃₂N₄NaO₁₁ [M+Na]⁺611.195979. found, 611.196049.

Sodium 5-acetamido-2,6-anhydro-3,4,5-trideoxy-4-(4-(2-methoxyphenyl)-[1,2,3,]triazol-1-yl)-D-glycero-D-galacto-non-2-enonate (IE832-37)

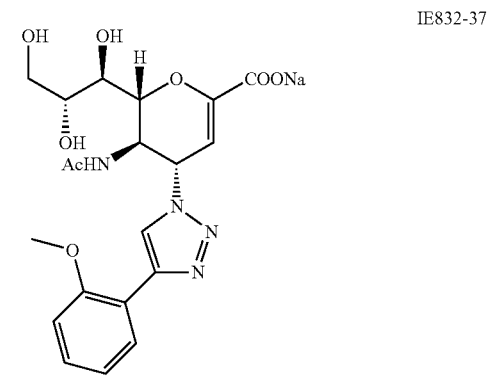

Yield=91%. $^1$H NMR (300 MHz, D$_2$O): δ 1.91 (s, 3H, NAc), 3.63-3.77 (m, 2H, H-9, H-7), 3.86-3.97 (m, 4H, H-9', OCH$_3$), 4.04 (ddd, J=9.3, 6.3, 2.6 Hz, 1H, H-8), 4.45 (m, 1H, H-5), 4.60 (dd, J=10.9, 1.2 Hz, 1H, H-6), 5.53 (dd, J=9.6, 2.3 Hz, 1H, H-4), 5.90 (d, J=2.2 Hz, 1H, H-3), 7.08-7.14 (m, 2H, Ph-H-3', Ph-H-5'), 7.34-7.49 (m, 1H, Ph-H-4'), 7.92 (dd, J=8.0, 1.7 Hz, H-6'), 8.32 (s, 1H, triazole-CH); $^{13}$C NMR (75 MHz, D$_2$O): δ 21.67 (NHCO<u>C</u>H$_3$), 48.59 (C-5), 55.38 (OCH$_3$), 59.81 (C-4), 63.09 (C-9), 68.11 (C-7), 69.74 (C-8), 75.40 (C-6), 101.95 (C-3), 111.84 (Ph), 117.87 (Ph q carbon), 121.00 (Ph), 123.12 (triazole-C-5), 127.27 (Ph), 130.05 (Ph), 143.23 (triazole-C-4), 150.33 (C-2), 155.70 (Ph q carbon), 168.81 (COONa), 173.59 (NH<u>C</u>OCH$_3$). LRMS [C$_{20}$H$_{23}$N$_4$NaO$_8$] (m/z): (+ve ion mode) 493.2 [M+1]$^+$.

Methyl 7,8,9-tri-O-acetyl-2,6-anhydro-3,4,5-trideoxy-5-isobutyramido-4-(4-(2-methoxyphenyl)-[1,2,3,]triazol-1-yl)-D-glycero-D-galacto-non-2-enonate (IE889-23)

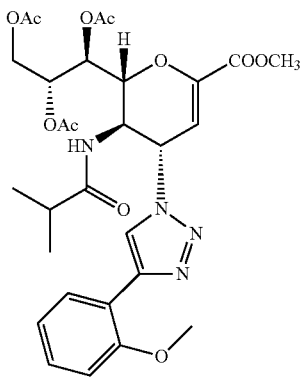

IE889-23

$^1$H NMR (300 MHz, CDCl$_3$): δ 1.00-1.04 (m, 6H, isobutyryl-2CH$_3$), 2.08 (s, 6H, 2 OAc), 2.10 (s, 3H, OAc), 2.25-2.34 (m, 1H, isobutyryl-CH), 3.84 (s, 3H, COOCH$_3$), 3.88 (s, 3H, Ph-OCH$_3$), 4.20-4.28 (m, 2H, H-9, H-5), 4.71 (dd, J=12.5, 2.6 Hz, 1H, H-9), 4.99 (d, J=10.5 Hz, 1H, H-6), 5.43 (m, 1H, H-8), 5.55 (dd, J=5.4, 1.6 Hz, 1H, H-7), 6.03 (dd, J=10.1, 2.4 Hz, 1H, H-4), 6.11 (d, J=2.3 Hz, 1H, H-3), 6.79 (d, J=8.3 Hz, 1H, NH), 6.93 (d, J=8.3 Hz, 1H, Ph-H-3'), 7.05 (m, 1H, Ph-H-5'), 7.29 (m, 1H, Ph-H-4'), 8.04 (s, 1H, triazole-CH), 8.2 (d, J=7.9 Hz, 1H, Ph-H-6'); $^{13}$C NMR (75 MHz, CDCl$_3$): δ 18.86, 19.34, 20.80, 20.95 (3 OCO<u>C</u>H$_3$, isobutyryl-2CH$_3$), 35.42 (isobutyryl-CH), 49.31 (C-5), 52.68 (COO<u>C</u>H$_3$), 55.29 (Ph-O<u>C</u>H$_3$), 57.12 (C-4), 62.19 (C-9), 67.74 (C-7), 70.75 (C-8), 76.30 (C-6), 107.73 (C-3), 110.71 (Ph), 118.68 (Ph q carbon), 120.89 (Ph), 122.62 (triazole-C-5), 127.51 (Ph), 129.21 (Ph), 143.30 (triazole-C-5), 145.68 (C-2), 155.68 (Ph q carbon), 161.56 (<u>C</u>OOCH$_3$), 170.10, 170.20, 170.68 (3 O<u>C</u>OCH$_3$), 178.05 (isobutyryl-CO). LRMS [C$_{29}$H$_{36}$N$_4$O$_{11}$] (m/z): (+ve ion mode) 639.1 [M+Na]$^+$; HRMS (API) (m/z): [M+Na]$^+$ calcd for C$_{29}$H$_{36}$N$_4$NaO$_{11}$ [M+Na]$^+$639.227279. found, 639.225897.

Sodium 2,6-anhydro-3,4,5-trideoxy-5-isobutyramido-4-(4-(2-methoxyphenyl)-[1,2,3,]triazol-1-yl)-D-glycero-D-galacto-non-2-enonate (IE889-34)

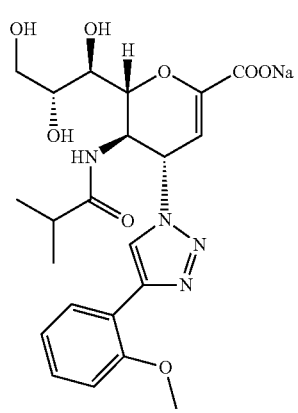

IE889-34

$^1$H NMR (300 MHz, D$_2$O): δ 0.90 (d, J=6.9 Hz, 3H, isobutyryl-CH$_3$), 0.97 (d, J=6.9 Hz, 3H, isobutyryl-CH$_3$), 2.31 (m, 1H, isobutyryl-CH), 3.53 (d, J=9.4 Hz, 1H, H-7), 3.60 (dd, J=11.5, 5.4 Hz, 1H, H-9), 3.79 (dd, J=11.4, 3.0 Hz, 1H, H-9'), 3.85-3.91 (m, 4H, H-8, Ph-OCH$_3$), 4.39-4.55 (m, 2H, H-5, H-6), 5.61 (dd, J=9.7, 2.2 Hz, 1H, H-4), 5.72 (d, J=2.2 Hz, 1H, H-3), 6.89-7.10 (m, 2H, Ph-H-3', Ph-H-5'), 7.27 (ddd, J=8.7, 7.4, 1.7 Hz, 1H, Ph-H-4'), 8.02 (dd, J=7.7, 1.7 Hz, 1H, Ph-H-6'), 8.23 (s, 1H, triazole-CH); $^{13}$C NMR (75 MHz, D$_2$O): δ 18.38, 18.53 (isobutyryl-2CH$_3$), 35.09 (isobutyryl-CH), 48.18 (C-5), 55.34 (OCH$_3$), 59.66 (C-4), 63.08 (C-9), 68.18 (C-7), 69.76 (C-8), 75.44 (C-6), 102.15 (C-3), 111.80 (Ph), 117.86 (Ph q carbon), 121.00 (Ph), 123.47 (triazole-C-5), 127.21 (Ph), 130.05 (Ph), 143.12 (triazole-C-4), 150.16 (C-2), 155.70 (Ph q carbon), 168.84 (COONa), 180.64 (NH<u>C</u>OCH$_3$); LRMS [C$_{22}$H$_{28}$N$_4$O$_8$] (m/z): (+ve ion mode) 499.1 [M+Na]$^+$; HRMS (API) (m/z): [M+Na]$^+$ calcd for C$_{22}$H$_{28}$N$_4$NaO$_8$ [M+Na]$^+$499.179935. found, 499.179943.

Methyl 5-acetamido-7,8,9-tri-O-acetyl-2,6-anhydro-3,4,5-trideoxy-4-(4-phenyl-[1,2,3,]triazol-1-yl)-D-glycero-D-galacto-non-2-enonate (IE889-45)

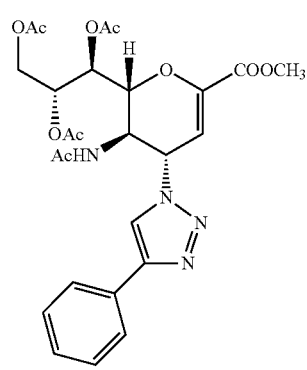

IE889-45

Purification by silica gel chromatography using ethylacetate: hexane (5:1) yielded (88 mg, 70%) of pure IE889-45. $^1$H NMR (300 MHz, CDCl$_3$): δ 1.79 (s, 3H, NAc), 2.04 (s, 3H, OAc), 2.05 (s, 3H, OAc), 2.06 (s, 3H, OAc), 3.81 (s, 3H, COOCH$_3$), 4.18 (dd, J=12.4, 7.2 Hz, 1H, H-9), 4.42 (m, 1H, H-5), 4.72 (dd, J=12.6, 2.7 Hz, 1H, H-9'), 4.79 (dd, J=10.5, 1.6 Hz, 1H, H-6), 5.42 (m, 1H, H-8), 5.58 (dd, J=5.1, 1.8 Hz, 1H, H-7), 5.83 (dd, J=10.0, 2.4 Hz, 1H, H-4), 6.04 (d, J=2.3 Hz, 1H, H-3), 7.20-7.42 (m, 4H, NH, Ph-H-3', Ph-H-4', Ph-H-5'), 7.72 (dd, J=8.2, 1.3 Hz, 2H, Ph-H-2', Ph-H-6'), 7.88 (s, 1H, triazole-CH); $^{13}$C NMR (75 MHz, CDCl$_3$) δ 20.70, 20.80, 20.90 (3 OCO$\underline{C}$H$_3$), 22.85 (NHCO$\underline{C}$H$_3$), 48.26 (C-5), 52.71 (COO$\underline{C}$H$_3$), 58.41 (C-4), 62.26 (C-9), 67.80 (C-7), 70.97 (C-8), 76.95 (C-6), 107.37 (C-3), 118.76 (triazole-C-5), 125.77 (Ph), 128.51 (Ph), 128.91 (Ph), 129.85 (Ph, q carbon), 145.95 (C-2), 148.13 (triazole-C-4), 161.32 ($\underline{C}$OOCH$_3$), 170.04, 170.30, 170.84, 170.99 (NH$\underline{C}$OCH$_3$, 3 O$\underline{C}$OCH$_3$). LRMS [C$_{26}$H$_{30}$N$_4$O$_{10}$] (m/z): (+ve ion mode) 581.0 [M+Na]$^+$; HRMS (API) (m/z): [M+Na]$^+$ calcd for C$_{26}$H$_{30}$N$_4$NaO$_{10}$ [M+Na]$^+$ 581.185414. found, 581.184724.

Sodium 5-acetamido-2,6-anhydro-3,4,5-trideoxy-4-(4-phenyl-[1,2,3,]triazol-1-yl)-D-glycero-D-galacto-non-2-enonate (IE889-52)

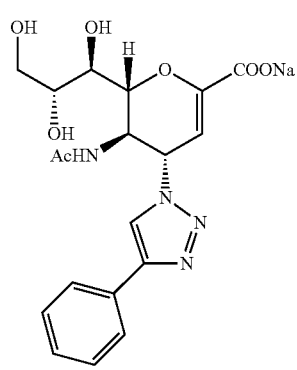

Yield=96%. $^1$H NMR (300 MHz, D$_2$O): δ 1.87 (s, 3H, NAc), 3.64 (dd, J=12.1, 6.4 Hz, 1H, H-9), 3.69 (dd, J=9.6, 1.4 Hz, 1H, H-7), 3.89 (dd, J=11.9, 2.7 Hz, 1H, H-9'), 4.00 (ddd, J=9.3, 6.3, 2.7 Hz, 1H, H-8), 4.39 (m, 1H, H-5), 4.56 (dd, J=10.8, 1.4 Hz, 1H, H-6), 5.49 (dd, J=9.7, 2.3 Hz, 1H, H-4), 5.83 (d, J=2.2 Hz, 1H, H-3), 7.40 (m, 1H, Ph-H4'), 7.46 (dd, J=8.4, 6.9 Hz, 2H, Ph-H-3', Ph-H-5'), 7.71 (d, J=7.1 Hz, 2H, Ph-H-2', Ph-H-6'), 8.28 (s, 1H, triazole-CH); $^{13}$C NMR (75 MHz, D$_2$O): δ 21.63 (NHCO$\underline{C}$H$_3$), 48.70 (C-5), 59.96 (C-4), 63.05 (C-9), 68.03 (C-7), 69.69 (C-8), 75.31 (C-6), 101.75 (C-3), 120.41 (Ph), 125.61 (Ph), 128.77 (triazole-C-5), 129.10 (Ph), 129.28 (Ph q carbon), 147.74 (triazole-C-4), 150.48 (C-2), 168.75 (COONa), 173.58 (NH$\underline{C}$OCH$_3$). LRMS [C$_{19}$H$_{21}$N$_4$NaO$_7$] (m/z): (+ve ion mode) 463.1 [M+Na]$^+$; HRMS (API) (m/z): [M+1]$^+$ calcd for C$_{19}$H$_{22}$N$_4$NaO$_7$ [M+H]$^+$ 441.138070. found, 441.140189.

Methyl 7,8,9-tri-O-acetyl-2,6-anhydro-3,4,5-trideoxy-5-isobutyramido-4-(4-methoxymethyl-[1,2,3,]triazol-1-yl)-D-glycero-D-galacto-non-2-enonate (IE927-57)

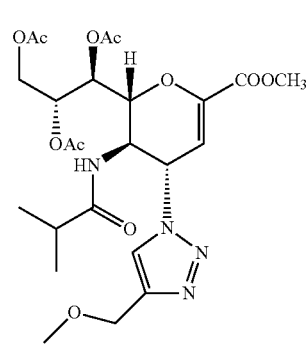

Purification by silica gel chromatography using ethylacetate: acetone (9:1) yielded (60 mg, 66%) of pure IE927-57. $^1$H NMR (300 MHz, CDCl$_3$): δ 0.97 (d, J=6.9 Hz, 3H, isobut-CH$_3$), 1.01 (d, J=6.8 Hz, 3H, isobut-CH$_3$), 2.05 (s, 3H, OAc), 2.08 (s, 6H, 2 OAc), 2.24 (m, 1H, isobut-CH), 3.37 (s, 3H, OCH$_3$), 3.81 (s, 3H, COOCH$_3$), 4.14-4.29 (m, 2H, H-9, H-5), 4.51 (s, 2H, OCH$_2$), 4.68 (dd, J=12.5, 2.6 Hz, 1H, H-9'), 4.84 (dd, J=10.5, 1.7 Hz, 1H, H-6), 5.38 (ddd, J=6.6, 5.5, 2.5 Hz, 1H, H-8), 5.48 (dd, J=5.5, 1.7 Hz, 1H, H-7), 5.91 (dd, J=10.0, 2.4 Hz, 1H, H-4), 6.02 (d, J=2.4 Hz, 1H, H-3), 6.44 (d, J=8.7 Hz, 1H, NH), 7.59 (s, 1H, triazole-CH); $^{13}$C NMR (75 MHz, CDCl$_3$): δ 18.81, 19.30, 20.74, 20.90 (3 OCO$\underline{C}$H$_3$, isobut-2CH$_3$), 35.51 (isobut-CH), 48.79 (C-5), 52.69 (COO$\underline{C}$H$_3$), 57.59 (C-4), 58.38 (OCH$_3$), 62.08 (C-9), 65.73 (OCH$_2$), 67.66 (C-7), 70.79 (C-8), 76.24 (C-6), 107.07 (C-3), 121.54 (triazole-C-5), 145.39 (triazole-C-4), 145.82 (C-2), 161.30 ($\underline{C}$OOCH$_3$), 170.15, 170.23, 170.69 (3 O$\underline{C}$OCH$_3$), 177.87 (isobut-CO). LRMS [C$_{24}$H$_{34}$N$_4$O$_{11}$] (m/z): (+ve ion mode) 577.2 [M+Na]$^+$.

Sodium 2,6-anhydro-3,4,5-trideoxy-5-isobutyramido-4-(4-methoxymethyl-[1,2,3,]triazol-1-yl)-D-glycero-D-galacto-non-2-enonate (IE927-60)

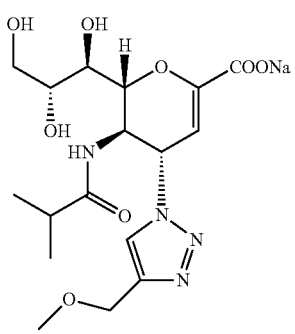

Yield=92%. $^1$H NMR (300 MHz, D$_2$O): δ 0.98 (d, J=7.0 Hz, 3H, isobut-CH$_3$), 1.03 (d, J=6.9 Hz, 3H, isobut-CH$_3$), 2.46 (m, 1H, isobut-CH), 3.39 (s, 3H, OCH$_3$), 3.65-3.76 (m, 2H, H-9, H-7), 3.94 (dd, J=11.9, 2.7 Hz, 1H, H-9'), 4.04 (ddd, J=9.3, 6.3, 2.6 Hz, 1H, H-8), 4.49 (m, 1H, H-5), 4.60-4.65 (m, 3H, H-6, OCH$_2$), 5.61 (dd, J=9.7, 2.3 Hz, 1H, H-4), 5.87 (d, J=2.2 Hz, 1H, H-3), 8.18 (s, 1H, triazole-CH); $^{13}$C NMR (75 MHz, D$_2$O): δ 18.43 (isobut-CH$_3$), 18.64 (isobut-CH$_3$), 35.10 (isobut-CH), 48.19 (C-5), 57.24 (OCH$_3$), 59.86 (C-4), 63.07 (C-9), 64.24 (OCH$_2$), 68.13 (C-7), 69.82 (C-8), 75.43 (C-6), 102.02 (C-3), 123.65 (triazole-C-5), 144.07 (triazole-C-4), 150.30 (C-2), 168.81 (COONa), 180.66 (isobut-CO). LRMS [C$_{17}$H$_{25}$N$_4$NaO$_8$] (m/z): (+ve ion mode) 459.0 [M+Na]$^+$; HRMS (API) (m/z): [M+Na]$^+$ calcd for C$_{17}$H$_{25}$N$_4$Na$_2$O$_8$[M+Na]$^+$459.1462. found, 459.1458.

Methyl 7,8,9-tri-O-acetyl-2,6-anhydro-3,4,5-trideoxy-4-(4-isobutyl-[1,2,3,]triazol-1-yl)-5-isobutyramido-D-glycero-D-galacto-non-2-enonate (IE927-58)

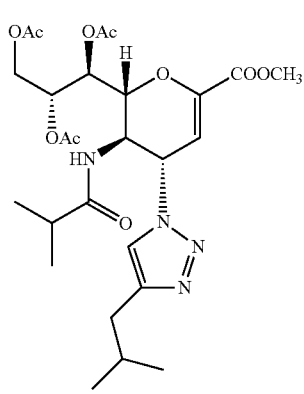

IE927-58

$^1$H NMR (300 MHz, CDCl$_3$): δ 0.90 (d, J=6.6 Hz, 6H, isobutyl-2CH$_3$), 0.96 (d, J=6.9 Hz, 3H, isobutyryl-CH$_3$), 1.00 (d, J=6.8 Hz, 3H, isobutyryl-CH$_3$), 1.90 (m, 1H, isobutyl-CH), 2.05 (s, 3H, OAc), 2.08 (s, 6H, 2 OAc), 2.22 (m, 1H, isobutyryl-CH), 2.53 (d, J=7.0 Hz, 2H, isobutyl-CH$_2$), 3.82 (s, 3H, COOCH$_3$), 4.13-4.36 (m, 2H, H-9, H-5), 4.70 (dd, J=12.5, 2.6 Hz, 1H, H-9'), 4.81 (dd, J=10.5, 1.7 Hz, 1H, H-6), 5.38 (ddd, J=6.6, 5.4, 2.5 Hz, 1H, H-8), 5.49 (dd, J=5.5, 1.7 Hz, 1H, H-7), 5.87 (dd, J=10.1, 2.4 Hz, 1H, H-4), 6.02 (d, J=2.4 Hz, 1H, H-3), 6.41 (d, J=8.8 Hz, 1H, NH), 7.32 (s, 1H, triazole-CH); $^{13}$C NMR (75 MHz, CDCl$_3$): δ 18.83, 19.29, 20.76, 20.92 (3 OCOCH$_3$+isobutyryl-2CH$_3$), 22.23 (isobutyl-2CH$_3$), 28.70 (isobutyl-CH), 34.68 (isobutyl-CH$_2$), 35.55 (isobutyryl-CH), 48.48 (C-5), 52.68 (COOCH$_3$), 57.47 (C-4), 62.11 (C-9), 67.69 (C-7), 70.89 (C-8), 76.44 (C-6), 107.53 (C-3), 120.36 (triazole-C-5), 145.56 (C-2), 147.53 (triazole-C-4), 161.40 (COOCH$_3$), 170.15, 170.24, 170.70 (3 OCOCH$_3$), 177.74 (isobutyryl-CO). LRMS [C$_{26}$H$_{38}$N$_4$O$_{10}$] (m/z): (+ve ion mode) 589.3 [M+Na]$^+$.

Sodium 2,6-anhydro-3,4,5-trideoxy-4-(4-isobutyl-[1,2,3,]triazol-1-yl)-5-isobutyramido-D-glycero-D-galacto-non-2-enonate

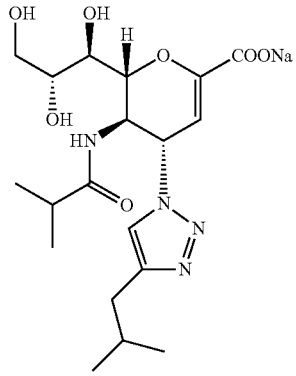

IE927-67

$^1$H NMR (300 MHz, D$_2$O): δ 0.90 (d, J=6.6 Hz, 6H, isobutyl-2CH$_3$), 0.97 (d, J=6.9 Hz, 3H, isobutyryl-CH$_3$), 1.02 (d, J=6.9 Hz, 3H, isobutyryl-CH$_3$), 1.92 (m, 1H, isobutyl-CH), 2.43 (m, 1H, isobutyryl-CH), 2.60 (d, J=6.9 Hz, 2H, isobutyl-CH$_2$), 3.62-3.74 (m, 2H, H-9, H-7), 3.93 (dd, J=11.9, 2.7 Hz, 1H, H-9'), 4.02 (ddd, J=9.3, 6.3, 2.6 Hz, 1H, H-8), 4.47 (m, 1H, H-5), 4.56 (d, J=11.1 Hz, 1H, H-6), 5.53 (dd, J=9.7, 2.2 Hz, 1H, H-4), 5.84 (d, J=2.2 Hz, 1H, H-3), 7.88 (s, 1H, triazole-CH); $^{13}$C NMR (75 MHz, D$_2$O): δ 18.45 (isobutyryl-CH$_3$), 18.61 (isobutyryl-CH$_3$), 21.31 (isobutyl-2CH$_3$), 28.17 (isobutyl-CH), 33.54 (isobutyl-CH$_2$), 35.12 (isobutyryl-CH), 48.09 (C-5), 59.53 (C-4), 63.07 (C-9), 68.14 (C-7), 69.78 (C-8), 75.47 (C-6), 102.30 (C-3), 121.99 (triazole-C-5), 147.82 (triazole-C-4), 150.05 (C-2), 168.88 (COONa), 180.46 (isobutyryl-CO). LRMS [C$_{19}$H$_{29}$N$_4$NaO$_7$] (m/z): (+ve ion mode) 471.2 [M+Na]$^+$, 449.2; HRMS (API) (m/z): [M+Na]$^+$ calcd for C$_{19}$H$_{29}$N$_4$Na$_2$O$_7$[M+Na]$^+$471.1826. found, 471.1823.

Methyl 7,8,9-tri-O-acetyl-2,6-anhydro-3,4,5-trideoxy-5-isobutyramido-4-(4-phenyl-[1,2,3,]triazol-1-yl)-D-glycero-D-galacto-non-2-enonate (IE984-4)

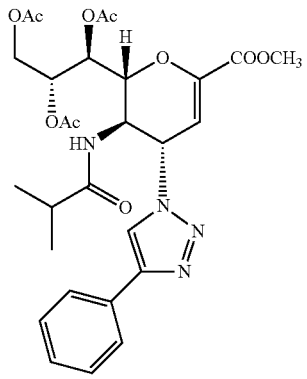

IE984-4

Purification by silica gel chromatography using ethylacetate: hexane (4:1) yielded (72 mg, 74%) of pure IE984-4. $^1$H NMR (300 MHz, CDCl$_3$): δ 0.95 (d, J=6.8 Hz, 3H, isobut-CH$_3$), 0.99 (d, J=6.9 Hz, 3H, isobut-CH$_3$), 2.06 (s, 3H, OAc), 2.09 (s, 6H, 2 OAc), 2.20-2.27 (m, 1H, isobut-CH), 3.83 (s, 3H, COOCH$_3$), 4.16-4.39 (m, 2H, H-9, H-5), 4.70 (dd, J=12.5, 2.6 Hz, 1H, H-9'), 4.88 (dd, J=10.5, 1.7 Hz, 1H, H-6), 5.40 (m, 1H, H-8), 5.52 (dd, J=5.4, 1.7 Hz, 1H, H-7), 5.99 (dd, J=10.0, 2.4 Hz, 1H, H-4), 6.08 (d, J=2.4 Hz, 1H, H-3), 6.51 (d, J=8.7 Hz, 1H, NH), 7.26-7.43 (m, 3H, Ph-H-3', Ph-H-4', Ph-H-5'), 7.74 (d, J=7.2 Hz, 2H, Ph-H-2', Ph-H-5'), 7.81 (s, 1H, triazole-CH); $^{13}$C NMR (75 MHz, CDCl$_3$): δ 18.83, 19.31, 20.76, 20.92 (3 OCO$\underline{C}$H$_3$, isobut-2CH$_3$), 35.55 (isobut-CH), 48.74 (C-5), 52.72 (COO$\underline{C}$H$_3$), 57.67 (C-4), 62.12 (C-9), 67.72 (C-7), 70.84 (C-8), 76.39 (C-6), 107.25 (C-3), 118.84 (triazole-C-5), 125.83 (Ph), 128.47 (Ph), 128.89 (Ph), 129.97 (Ph q carbon), 145.81 (C-2), 148.19 (triazole-C-4), 161.35 ($\underline{C}$OOCH$_3$), 170.18, 170.26, 170.71 (3 O$\underline{C}$OCH$_3$), 178.00 (isobut-CO). LRMS [C$_{28}$H$_{34}$N$_4$O$_{10}$] (m/z): (+ve ion mode) 608.9 [M+Na]$^+$.

Sodium 2,6-anhydro-3,4,5-trideoxy-5-isobutyramido-4-(4-phenyl-[1,2,3,]triazol-1-yl)-D-glycero-D-galacto-non-2-enonate (IE984-5)

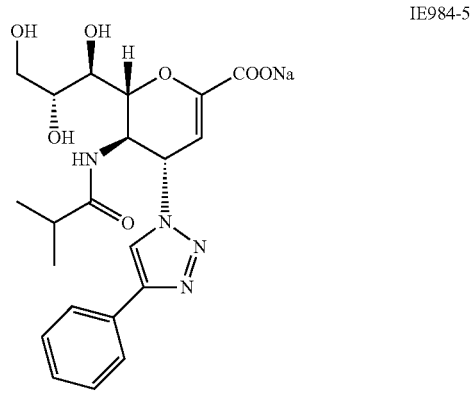

IE984-5

Yield=89%. $^1$H NMR (300 MHz, D$_2$O): δ 0.94 (d, J=6.9 Hz, 3H, isobut-CH$_3$), 0.99 (d, J=6.9 Hz, 3H, isobut-CH$_3$), 2.43 (m, 1H, isobut-CH), 3.60-3.76 (m, 2H, H-9, H-7), 3.93 (dd, J=12.0, 2.7 Hz, 1H, H-9'), 4.04 (ddd, J=9.2, 6.3, 2.6 Hz, 1H, H-8), 4.51 (m, 1H, H-5), 4.62 (d, J=11.0 Hz, 1H, H6), 5.58 (dd, J=9.7, 2.3 Hz, 1H, H-4), 5.88 (d, J=2.2 Hz, 1H, H-3), 7.42-7.54 (m, 3H, Ph-H-3', Ph-H-4', Ph-H-5'), 7.78 (d, J=7.1 Hz, 2H, Ph-H-2', Ph-H-6'), 8.36 (s, 1H, triazole-CH); $^{13}$C NMR (75 MHz, D$_2$O): δ 18.38 (isobut-CH$_3$), 18.65 (isobut-CH$_3$), 35.10 (isobut-CH), 48.23 (C-5), 59.91 (C-4), 63.07 (C-9), 68.15 (C-7), 69.76 (C-8), 75.41 (C-6), 101.96 (C-3), 120.66 (Ph), 125.67 (Ph), 128.81 (triazole-C-5), 129.16 (Ph), 129.36 (Ph q carbon), 147.71 (triazole-C-4), 150.32 (C-2), 168.80 (COONa), 180.67 (isobut-CO). LRMS [C$_{21}$H$_{25}$N$_4$NaO$_7$] (m/z): (+ve ion mode) 491.2 [M+Na]$^+$; HRMS (API) (m/z): [M+Na]$^+$ calcd for C$_{21}$H$_{25}$N$_4$Na$_2$O$_7$ [M+Na]$^+$491.1513. found, 491.1515.

Methyl 5-acetamido-7,8,9-tri-O-acetyl-2,6-anhydro-4-(4-(2-chlorophenyl)-[1,2,3,]triazol-1-yl)-3,4,5-trideoxy-D-glycero-D-galacto-non-2-enonate (IE1172-70)

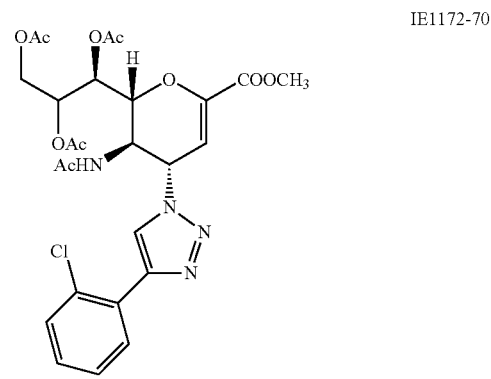 [SMILES: COC(=O)C1=C[C@H](n2cc(-c3ccccc3Cl)nn2)[C@@H](NC(C)=O)[C@H]([C@H](OC(C)=O)C(COC(C)=O)OC(C)=O)O1]

IE1172-70

Purification by silica gel chromatography using acetone: hexane (3:2) yielded (76%) of pure IE1172-70. $^1$H NMR (400 MHz, CDCl$_3$): δ 1.81 (s, 3H, NAc), 2.05 (s, 6H, 2 OAc), 2.07 (s, 3H, OAc), 3.82 (s, 3H, COOCH$_3$), 4.20 (dd, J=12.5, 7.0 Hz, 1H, H-9), 4.30 (q, J=9.8 Hz, 1H, H-5), 4.71 (dd, J=12.5, 2.7 Hz, 1H, H-9'), 4.86 (dd, J=10.7, 1.9 Hz, 1H, H-6), 5.42 (ddd, J=6.8, 5.4, 2.6 Hz, 1H, H-8), 5.55 (dd, J=5.3, 1.9 Hz, 1H, H-7), 5.91 (dd, J=10.0, 2.4 Hz, 1H, H-4), 6.09 (d, J=2.3 Hz, 1H, H-3), 6.93 (d, J=8.8 Hz, 1H, NH), 7.26 (td, J=7.8, 1.8 Hz, 1H, Ph-H), 7.34 (td, J=7.6, 1.4 Hz, 1H, Ph-H), 7.41 (dd, J=8.0, 1.3 Hz, 1H, Ph-H), 8.05 (dd, J=7.9, 1.7 Hz, 1H, Ph-H), 8.19 (s, 1H, triazole-CH); $^{13}$C NMR (101 MHz, CDCl$_3$) δ 20.75, 20.80, 20.93 (3 OCO$\underline{C}$H$_3$), 22.94 (NHCO$\underline{C}$H$_3$), 49.00 (C-5), 52.74 (COO$\underline{C}$H$_3$), 57.92 (C-4), 62.18 (C-9), 67.81 (C-7), 70.86 (C-8), 76.48 (C-6), 107.11 (C-3), 122.63 (triazole-C-5), 127.22 (Ph), 128.62 (Ph, q carbon), 129.44 (Ph), 129.80 (Ph), 130.28 (Ph), 131.42 (Ph, q carbon), 144.31 (triazole-C-4), 145.96 (C-2), 161.34 ($\underline{C}$OOCH$_3$), 170.20, 170.28, 170.79, 171.01 (NH$\underline{C}$OCH$_3$, 3 O$\underline{C}$OCH$_3$); LRMS [C$_{26}$H$_{29}$ClN$_4$O$_{10}$] (m/z): (+ve ion mode) 615.1 [M+Na]$^+$.

Sodium 5-acetamido-2,6-anhydro-4-(4-(2-chlorophenyl)-[1,2,3,]triazol-1-yl)-3,4,5-trideoxy-D-glycero-D-galacto-non-2-enonate (IE1172-78)

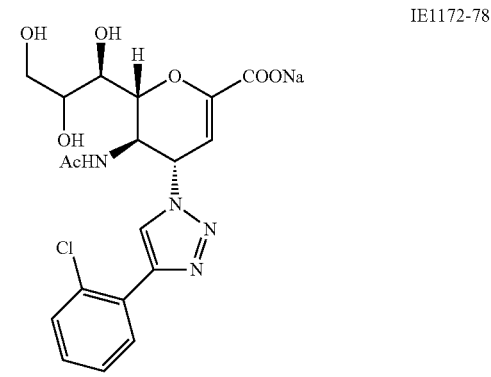

IE1172-78

Yield=89%. $^1$H NMR (400 MHz, D$_2$O): δ 1.93 (s, 3H, NAc), 3.68 (dd, J=12.0, 6.4 Hz, 1H, H-9), 3.73 (dd, J=9.7, 1.3 Hz, 1H, H-7), 3.93 (dd, J=12.0, 2.7 Hz, 1H, H-9'), 4.03 (ddd, J=9.3, 6.3, 2.6 Hz, 1H, H-8), 4.48 (t, J=10.3 Hz, 1H, H-5), 4.61 (dd, J=11.1, 1.3 Hz, 1H, H-6), 5.58 (dd, J=9.7, 2.3 Hz, 1H, H-4), 5.93 (d, J=2.2 Hz, 1H, H-3), 7.37-7.51 (m, 2H, 2Ph-H), 7.58 (dd, J=7.5, 1.9 Hz, 1H, Ph-H), 7.81 (dd, J=7.0, 2.5 Hz, 1H, Ph-H), 8.49 (s, 1H, triazole-CH); $^{13}$C NMR (101 MHz, D$_2$O): δ 21.70 (NHCO<u>C</u>H$_3$), 48.67 (C-5), 60.10 (C-4), 63.09 (C-9), 68.10 (C-7), 69.74 (C-8), 75.39 (C-6), 101.87 (C-3), 123.78 (triazole-C-5), 127.36 (Ph), 128.03 (Ph q carbon), 129.94 (Ph), 130.10 (Ph), 130.19 (Ph), 131.50 (Ph q carbon), 144.37 (triazole-C-4), 150.41 (C-2), 168.78 (COONa), 173.56 (NH<u>C</u>OCH$_3$); LRMS [C$_{19}$H$_{20}$ClN$_4$NaO$_7$] (m/z): (+ve ion mode) 497.1 [M+Na]$^+$.

Methyl 5-acetamido-7,8,9-tri-O-acetyl-2,6-anhydro-3,4,5-trideoxy-4-(4-(2-methyl phenyl)-[1,2,3,]triazol-1-yl)-D-glycero-D-galacto-non-2-enonate (IE1172-72)

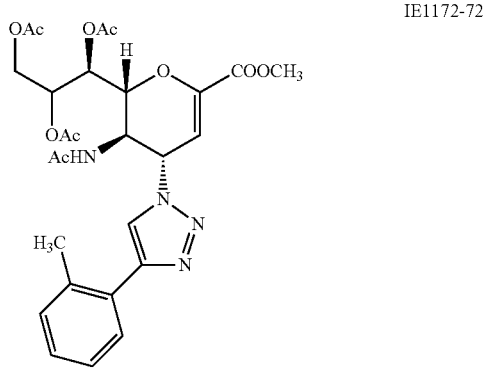 [SMILES: COC(=O)C1=C[C@H](n2cc(-c3ccccc3C)nn2)[C@@H](NC(C)=O)[C@H]([C@H](OC(C)=O)C(COC(C)=O)OC(C)=O)O1]

IE1172-72

Purification by silica gel chromatography using acetone:hexane (4:3) yielded (81%) of pure IE1172-72. $^1$H NMR (400 MHz, CDCl$_3$): δ 1.76 (s, 3H, NAc), 2.04 (s, 3H, OAc), 2.06 (s, 3H, OAc), 2.07 (s, 3H, OAc), 2.33 (s, 3H, Ph-CH$_3$), 3.82 (s, 3H, COOCH$_3$), 4.19 (dd, J=12.5, 7.1 Hz, 1H, H-9), 4.39 (q, J=9.9 Hz, 1H, H-5), 4.71 (dd, J=12.4, 2.7 Hz, 1H, H-9'), 4.82 (dd, J=10.4, 2.0 Hz, 1H, H-6), 5.41 (ddd, J=7.6, 5.1, 2.7 Hz, 1H, H-8), 5.57 (dd, J=5.2, 1.9 Hz, 1H, H-7), 5.86 (dd, J=10.2, 2.4 Hz, 1H, H-4), 6.07 (d, J=2.3 Hz, 1H, H-3), 7.16-7.30 (m, 4H, NH, 3PH—H), 7.60 (m, 1H, Ph-H), 7.70 (s, 1H, triazole-CH); $^{13}$C NMR (101 MHz, CDCl$_3$) δ 20.72, 20.81, 20.93 (3 OCO<u>C</u>H$_3$), 21.09 (Ph-CH$_3$), 22.82 (NHCO<u>C</u>H$_3$), 48.63 (C-5), 52.73 (COO<u>C</u>H$_3$), 58.03 (C-4), 62.21 (C-9), 67.76 (C-7), 70.93 (C-8), 76.72 (C-6), 107.38 (C-3), 121.28 (triazole-C-5), 126.16 (Ph), 128.58 (Ph), 128.94 (Ph), 129.23 (Ph, q carbon), 130.90 (Ph), 135.64 (Ph, q carbon), 145.85 (C-2), 147.15 (triazole-C-4), 161.37 (<u>C</u>OOCH$_3$), 170.07, 170.30, 170.80, 171.06 (NH<u>C</u>OCH$_3$, 3 O<u>C</u>OCH$_3$); LRMS [C$_{27}$H$_{32}$N$_4$O$_{10}$] (m/z): (+ve ion mode) 595.2 [M+Na]$^+$.

Sodium 5-acetamido-2,6-anhydro-3,4,5-trideoxy-4-(4-(2-methylphenyl)-[1,2,3,]triazol-1-yl)-D-glycero-D-galacto-non-2-enonate (IE1172-82)

IE1172-82

Yield=85%. $^1$H NMR (400 MHz, D$_2$O): δ 1.93 (s, 3H, NAc), 2.36 (s, 3H, Ph-CH$_3$), 3.68 (dd, J=11.9, 6.3 Hz, 1H, H-9), 3.74 (d, J=9.7 Hz, 1H, H-7), 3.93 (dd, J=12.0, 2.7 Hz, 1H, H-9'), 4.03 (ddd, J=9.3, 6.3, 2.6 Hz, 1H, H-8), 4.48 (t, J=10.3 Hz, 1H, H-5), 4.60 (dd, J=10.8, 1.3 Hz, 1H, H-6), 5.58 (dd, J=9.7, 2.3 Hz, 1H, H-4), 5.92 (d, J=2.3 Hz, 1H, H-3), 7.29-7.46 (m, 3H, 3Ph-H), 7.58 (d, J=7.4 Hz, 1H, Ph-H), 8.19 (s, 1H, triazole-CH); $^{13}$C NMR (101 MHz, D$_2$O): δ 19.77 (Ph-<u>C</u>H$_3$), 21.67 (NHCO<u>C</u>H$_3$), 48.69 (C-5), 60.06 (C-4), 63.09 (C-9), 68.10 (C-7), 69.74 (C-8), 75.39 (C-6), 101.92 (C-3), 122.60 (triazole-C-5), 126.17 (Ph), 128.94 (Ph q carbon), 129.01 (Ph), 129.03 (Ph), 130.76 (Ph), 136.45 (Ph q carbon), 146.87 (triazole-C-4), 150.42 (C-2), 168.80 (COONa), 173.52 (NH<u>C</u>OCH$_3$); LRMS [C$_{20}$H$_{23}$N$_4$NaO$_7$] (m/z): (+ve ion mode) 477.2 [M+Na]$^+$.

Methyl 5-acetamido-7,8,9-tri-O-acetyl-2,6-anhydro-3,4,5-trideoxy-4-(4-(2-(trifluoromethyl)phenyl)-[1,2,3,]triazol-1-yl)-D-glycero-D-galacto-non-2-enonate (IE1172-74)

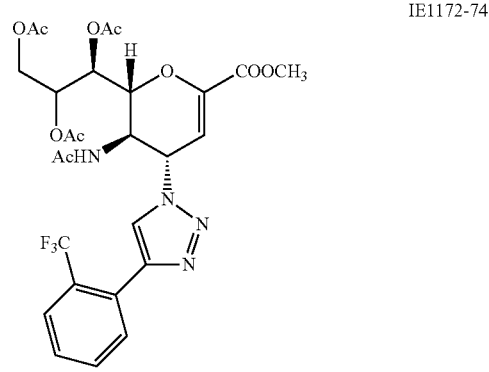 [SMILES: COC(=O)C1=C[C@H](n2cc(-c3ccccc3C(F)(F)F)nn2)[C@@H](NC(C)=O)[C@H]([C@H](OC(C)=O)C(COC(C)=O)OC(C)=O)O1]

IE1172-74

Purification by silica gel chromatography using acetone:hexane (3:2) yielded (90%) of pure IE1172-74. $^1$H NMR (400 MHz, CDCl$_3$): δ 1.75 (s, 3H, NAc), 2.04 (s, 3H, OAc), 2.05 (s, 3H, OAc), 2.08 (s, 3H, OAc), 3.83 (s, 3H, COOCH$_3$), 4.14-4.35 (m, 2H, H-9, H-5), 4.70 (dd, J=12.4, 2.6 Hz, 1H, H-9'), 4.92 (dd, J=10.6, 1.8 Hz, 1H, H-6), 5.42 (ddd, J=6.8, 5.4, 2.6 Hz, 1H, H-8), 5.54 (dd, J=5.5, 1.8 Hz, 1H, H-7), 5.97 (dd, J=10.1, 2.4 Hz, 1H, H-4), 6.08 (d, J=2.3 Hz, 1H, H-3), 6.99 (d, J=8.5 Hz, 1H, NH), 7.48 (t, J=7.7 Hz, 1H, Ph-H), 7.61 (td, J=7.7, 1.4 Hz, 1H, Ph-H), 7.72 (dd, J=8.1, 1.4 Hz, 1H, Ph-H), 7.75-7.84 (m, 2H, Ph-H, triazole- CH); $^{13}$C NMR (101 MHz, CDCl$_3$) δ 20.76, 20.79, 20.92 (3 OCO<u>CH</u>$_3$), 22.73 (NHCO<u>CH</u>$_3$), 49.38 (C-5), 52.74 (COO<u>CH</u>$_3$), 57.48 (C-4), 62.16 (C-9), 67.80 (C-7), 70.79 (C-8), 76.25 (C-6), 107.09 (C-3), 122.58 (Ph, q carbon), 122.82 (q, J=5.1, 4.6 Hz, triazole-C-5), 125.29 (Ph, q carbon), 126.22 (q, J=5.5 Hz, Ph), 127.61 (q, J=30.4 Hz, CF$_3$), 128.71 (Ph), 131.79 (Ph), 132.09 (Ph), 144.40 (triazole-C-4), 145.84 (C-2), 161.35 (<u>C</u>OOCH$_3$), 170.20, 170.26, 170.75, 171.19 (NH<u>C</u>OCH$_3$, 3 O<u>C</u>OCH$_3$); LRMS [O$_{27}$H$_{29}$F$_3$N$_4$O$_{10}$] (m/z): (+ve ion mode) 649.1 [M+Na]$^+$.

Sodium 5-acetamido-2,6-anhydro-3,4,5-trideoxy-4-(4-(2-(trifluoromethyl)phenyl)-[1,2,3,]triazol-1-yl)-D-glycero-D-galacto-non-2-enonate (IE1172-83)

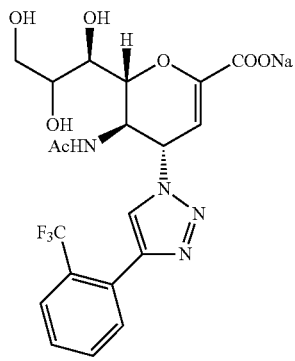

IE1172-83

Yield=77%. $^1$H NMR (400 MHz, D$_2$O): δ 1.94 (s, 3H, NAc), 3.68 (dd, J=11.8, 6.3 Hz, 1H, H-9), 3.73 (d, J=9.6 Hz, 1H, H-7), 3.93 (dd, J=11.9, 2.7 Hz, 1H, H-9'), 4.03 (ddd, J=9.3, 6.2, 2.6 Hz, 1H, H-8), 4.51 (t, J=10.2 Hz, 1H, H-5), 4.59 (d, J=10.9 Hz, 1H, H-6), 5.61 (dd, J=9.7, 2.3 Hz, 1H, H-4), 5.93 (d, J=2.2 Hz, 1H, H-3), 7.61-7.70 (m, 2H, 2Ph-H), 7.75 (t, J=7.6 Hz, 1H, Ph-H), 7.90 (d, J=7.8 Hz, 1H, Ph-H), 8.23 (s, 1H, triazole-CH); $^{13}$C NMR (101 MHz, D$_2$O): δ 21.61 (NHCO<u>CH</u>$_3$), 48.62 (C-5), 59.96 (C-4), 63.09 (C-9), 68.10 (C-7), 69.73 (C-8), 75.48 (C-6), 101.96 (C-3), 122.49 (Ph q carbon), 123.77 (q, J=3.0 Hz, triazole-C-5), 125.20 (Ph q carbon), 126.32 (q, J=5.4 Hz, Ph), 127.39-128.51 (m, CF$_3$), 129.38 (Ph), 131.99 (Ph), 132.27 (Ph), 144.83 (triazole-C-4), 150.33 (C-2), 168.75 (COONa), 173.52 (NH<u>C</u>OCH$_3$); LRMS [C$_{20}$H$_{20}$F$_3$N$_4$NaO$_7$](m/z): (+ve ion mode) 531.2 [M+Na]$^+$.

Methyl 5-acetamido-7,8,9-tri-O-acetyl-2,6-anhydro-3,4,5-trideoxy-4-(5-methoxymethyl-[1,2,3,]triazol-1-yl)-D-glycero-D-galacto-non-2-enonate (IE1172-79)

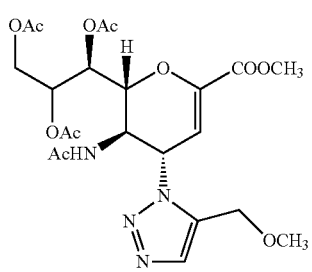

IE1172-79

Purification by silica gel chromatography using ethylacetate: acetone (6:1) yielded (68%) of pure IE1172-79. $^1$H NMR (400 MHz, CDCl$_3$): δ 1.87 (s, 3H, NAc), 2.01 (s, 3H, OAc), 2.03 (s, 3H, OAc), 2.07 (s, 3H, OAc), 3.34 (s, 3H, CH$_2$O<u>CH</u>$_3$), 3.79 (s, 3H, COOCH$_3$), 4.15-4.27 (m, 2H, H-5, H-9), 4.34-4.50 (m, 2H, CH$_2$O), 4.60 (dd, J=12.5, 2.6 Hz, 1H, H-9'), 5.09 (dd, J=10.7, 1.8 Hz, 1H, H-6), 5.42 (td, J=6.2, 2.6 Hz, 1H, H-8), 5.49 (dd, J=6.3, 1.8 Hz, 1H, H-7), 5.91 (d, J=2.4 Hz, 1H, H-3), 6.05 (dd, J=9.9, 2.5 Hz, 1H, H-4), 7.26 (d, J=7.8 Hz, 1H, NH), 7.46 (s, 1H, triazole-CH); $^{13}$C NMR (101 MHz, CDCl$_3$) δ 20.71, 20.76, 20.92 (3 OCO<u>CH</u>$_3$), 23.04 (NHCO<u>CH</u>$_3$), 50.03 (C-5), 52.60 (COO<u>CH</u>$_3$), 55.20 (C-4), 58.59 (<u>CH</u>$_2$OCH$_3$), 61.94 (<u>CH</u>$_2$OCH$_3$), 62.10 (C-9), 67.74 (C-7), 70.25 (C-8), 75.54 (C-6), 107.87 (C-3), 133.48 (triazole-C-4), 134.46 (triazole-C-5), 145.50 (C-2), 161.55 (<u>C</u>OOCH$_3$), 169.96, 170.21, 170.66, 171.54 (NH<u>C</u>OCH$_3$, 3 O<u>C</u>OCH$_3$); LRMS [C$_{22}$H$_{30}$N$_4$O$_{11}$] (m/z): (+ve ion mode) 549.3 [M+Na]$^+$.

Sodium 5-acetamido-2,6-anhydro-3,4,5-trideoxy-4-(5-methoxymethyl-[1,2,3,]triazol-1-yl)-D-glycero-D-galacto-non-2-enonate (IE1172-87)

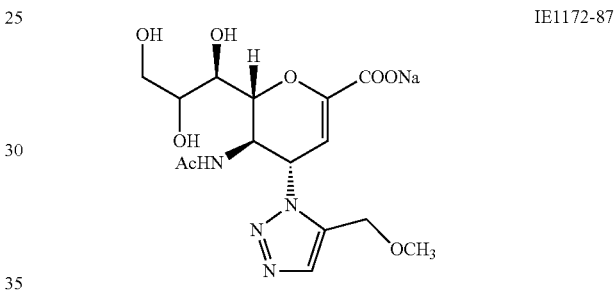

IE1172-87

Yield=83%. $^1$H NMR (400 MHz, D$_2$O): δ 1.89 (s, 3H, NAc), 3.40 (s, 3H, OCH$_3$), 3.65-3.74 (m, 2H, H-9, H-7), 3.93 (dd, J=12.0, 2.7 Hz, 1H, H-9'), 4.03 (ddd, J=9.3, 6.3, 2.6 Hz, 1H, H-8), 4.57 (d, J=10.9 Hz, 1H, H-6), 4.61-4.73 (m, 3H, H-5, OCH$_2$), 5.62 (dd, J=9.6, 2.4 Hz, 1H, H-4), 5.85 (d, J=2.4 Hz, 1H, H-3), 7.81 (s, 1H, triazole-CH); $^{13}$C NMR (101 MHz, D$_2$O): δ 21.73 (NHCO<u>CH</u>$_3$), 47.97 (C-5), 57.87 (OCH$_3$), 58.92 (C-4), 61.34 (O<u>CH</u>$_2$), 63.08 (C-9), 68.08 (C-7), 69.70 (C-8), 75.34 (C-6), 102.36 (C-3), 134.66 (triazole-C-5), 134.73 (triazole-C-4), 150.02 (C-2), 168.75 (COONa), 173.61 (NH<u>C</u>OCH$_3$); LRMS [C$_{15}$H$_{21}$N$_4$NaO$_8$] (m/z): (+ve ion mode) 431.2 [M+Na]$^+$.

Methyl 5-acetamido-7,8,9-tri-O-acetyl-2,6-anhydro-3,4,5-trideoxy-4-(5-phenyl-[1,2,3,]triazol-1-yl)-D-glycero-D-galacto-non-2-enonate (IE1172-39)

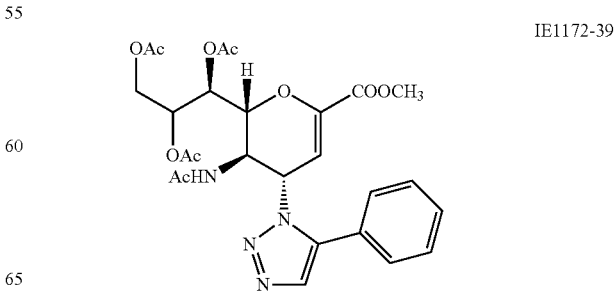

IE1172-39

Purification by silica gel chromatography using Hexane:acetone (4:3) yielded (82%) of pure IE1172-39. $^1$H NMR (400 MHz, CDCl$_3$): δ 1.74 (s, 3H, NAc), 2.02 (s, 3H, OAc), 2.04 (s, 3H, OAc), 2.08 (s, 3H, OAc), 3.80 (s, 3H, COOCH$_3$), 4.04 (td, J=10.1, 7.3 Hz, 1H, H-5), 4.21 (m, 1H, H-9), 4.51 (m, 1H, H-9'), 5.05 (d, J=10.5 Hz, 1H, H-6), 5.31-5.46 (m, 2H, H-7, H-8), 5.98 (d, J=2.5 Hz, 1H, H-3), 6.09 (dd, J=9.7, 2.5 Hz, 1H, H-4), 6.75 (d, J=7.4 Hz, 1H, NH), 7.30-7.32 (m, 2H, 2Ph-H), 7.47-7.53 (m, 3H, 3Ph-H), 7.58 (s, 1H, triazole-CH); $^{13}$C NMR (101 MHz, CDCl$_3$) δ 20.73, 20.79, 20.89 (3 OCO$\underline{C}$H$_3$), 23.03 (NHCO$\underline{C}$H$_3$), 50.85 (C-5), 52.58 (COO$\underline{C}$H$_3$), 54.24 (C-4), 62.01 (C-9), 67.63 (C-7), 69.87 (C-8), 74.78 (C-6), 108.02 (C-3), 126.01 (Ph q carbon), 129.07 (Ph), 129.23 (Ph), 130.07 (Ph), 132.70 (triazole-C-4), 139.35 (triazole-C-5), 145.49 (C-2), 161.49 ($\underline{C}$OOCH$_3$), 169.79, 170.40, 170.58, 171.03 (NH$\underline{C}$OCH$_3$, 3 O$\underline{C}$OCH$_3$); LRMS [C$_{26}$H$_{30}$N$_4$O$_{10}$] (m/z): (+ve ion mode) 581.1 [M+Na]$^+$.

Sodium 5-acetamido-2,6-anhydro-3,4,5-trideoxy-4-(5-phenyl-[1,2,3,]triazol-1-yl)-D-glycero-D-galacto-non-2-enonate (IE1172-45)

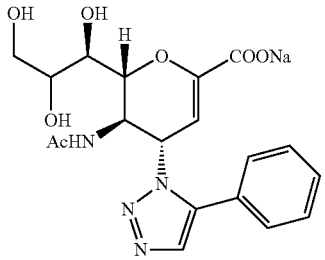

IE1172-45

Yield=88%. $^1$H NMR (400 MHz, D$_2$O): δ 1.72 (s, 3H, NAc), 3.55 (d, J=9.7 Hz, 1H, H-7), 3.62 (dd, J=12.0, 6.3 Hz, 1H, H-9), 3.87 (dd, J=11.9, 2.7 Hz, 1H, H-9'), 3.95 (ddd, J=9.3, 6.2, 2.7 Hz, 1H, H-8), 4.33-4.51 (m, 2H, H-5, H-6), 5.63 (dd, J=9.3, 2.2 Hz, 1H, H-4), 5.98 (d, J=2.3 Hz, 1H, H-3), 7.46-7.56 (m, 2H, 2Ph-H), 7.57-7.61 (m, 3H, 3Ph-H), 7.85 (s, 1H, triazole-CH); $^{13}$C NMR (101 MHz, D$_2$O): δ 21.88 (NHCO$\underline{C}$H$_3$), 48.83 (C-5), 57.52 (C-4), 63.00 (C-9), 67.95 (C-7), 69.64 (C-8), 75.01 (C-6), 103.14 (C-3), 125.71 (Ph q carbon), 129.13 (Ph), 129.28 (Ph), 130.10 (Ph), 133.02 (triazole-C-4), 139.88 (triazole-C-5), 149.90 (C-2), 168.80 (COONa), 173.30 (NH$\underline{C}$OCH$_3$); LRMS [C$_{19}$H$_{21}$N$_4$NaO$_7$] (m/z): (+ve ion mode) 462.6 [M+Na]$^+$.

Methyl 5-acetamido-7,8,9-tri-O-acetyl-2,6-anhydro-3,4,5-trideoxy-4-(4,5-diphenyl-[1,2,3,]triazol-1-yl)-D-glycero-D-galacto-non-2-enonate (IE1172-90)

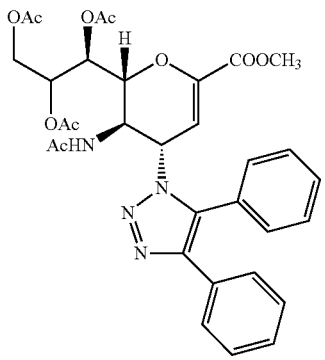

IE1172-90

Purification by silica gel chromatography using Hexane:acetone (3:2) yielded (79%) of pure IE1172-90. $^1$H NMR (400 MHz, CDCl$_3$): δ 1.82 (s, 3H, NAc), 2.03 (s, 6H, 2 OAc), 2.10 (s, 3H, OAc), 3.78 (s, 3H, COOCH$_3$), 4.17-4.27 (m, 2H, H-5, H-9), 4.52 (dd, J=12.5, 2.6 Hz, 1H, H-9'), 5.07 (d, J=10.4 Hz, 1H, H-6), 5.40 (td, J=6.3, 2.5 Hz, 1H, H-8), 5.45 (dd, J=6.8, 1.7 Hz, 1H, H-7), 5.79-5.93 (m, 2H, H-3, H-4), 7.13-7.27 (m, 6H, NH, 5Ph-H), 7.28-7.34 (m, 2H, 2Ph-H), 7.38-7.48 (m, 3H, 3Ph-H); $^{13}$C NMR (101 MHz, CDCl$_3$) δ 20.75, 20.76, 20.89 (3 OCO$\underline{C}$H$_3$), 23.33 (NHCO$\underline{C}$H$_3$), 50.56 (C-5), 52.54 (COO$\underline{C}$H$_3$), 54.97 (C-4), 62.09 (C-9), 67.54 (C-7), 69.93 (C-8), 75.13 (C-6), 108.41 (C-3), 126.48 (Ph q carbon), 127.15 (Ph), 128.09 (Ph), 128.44 (Ph), 129.31 (Ph), 130.11 (Ph), 130.14 (Ph), 130.18 (Ph q carbon), 135.11 (triazole-C), 144.35 (triazole-C), 145.49 (C-2), 161.50 ($\underline{C}$OOCH$_3$), 169.80, 170.27, 170.63, 171.37 (NH$\underline{C}$OCH$_3$, 3 O$\underline{C}$OCH$_3$); LRMS [C$_{32}$H$_{34}$N$_4$O$_{10}$] (m/z): (+ve ion mode) 657.3 [M+Na]$^+$.

Sodium 5-acetamido-2,6-anhydro-3,4,5-trideoxy-4-(4,5-diphenyl-[1,2,3,]triazol-1-yl)-D-glycero-D-galacto-non-2-enonate (IE1172-102)

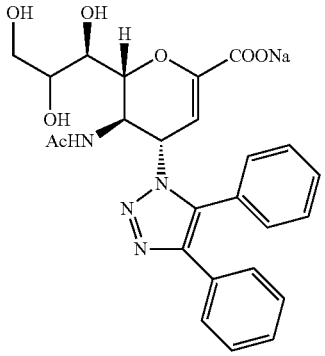

IE1172-102

Yield=84%. $^1$H NMR (400 MHz, D$_2$O): δ 1.83 (s, 3H, NAc), 3.58 (d, J=9.7 Hz, 1H, H-7), 3.63 (dd, J=12.0, 6.2 Hz, 1H, H-9), 3.88 (dd, J=12.0, 2.7 Hz, 1H, H-9'), 3.94 (ddd, J=9.4, 6.2, 2.7 Hz, 1H, H-8), 4.37 (d, J=11.0 Hz, 1H, H-6), 4.59 (dd, J=11.2, 9.2 Hz, 1H, H-5), 5.48 (d, J=9.7 Hz, 1H, H-4), 5.90 (s, 1H, H-3), 7.36-7.59 (m, 10H, Ph-H); $^{13}$C NMR (101 MHz, D$_2$O): δ 21.94 (NHCO$\underline{C}$H$_3$), 48.33 (C-5), 58.44 (C-4), 63.01 (C-9), 67.98 (C-7), 69.61 (C-8), 74.96 (C-6), 103.15 (C-3), 126.05 (Ph q carbon), 127.31 (Ph), 128.55 (Ph), 128.80 (Ph), 129.21 (Ph), 129.63 (Ph q carbon), 130.25 (Ph), 130.42 (Ph), 135.79 (triazole-C), 144.67 (triazole-C), 149.71 (C-2), 168.67 (COONa), 173.41 (NH$\underline{C}$OCH$_3$); LRMS [C$_{25}$H$_{25}$N$_4$NaO$_7$] (m/z): (+ve ion mode) 539.2 [M+Na]$^+$.

Methyl 5-acetamido-7,8,9-tri-O-acetyl-2,6-anhydro-4-(4-(2-bromophenyl)-[1,2,3,]triazol-1-yl)-3,4,5-trideoxy-D-glycero-D-galacto-non-2-enonate (IE1257-75)

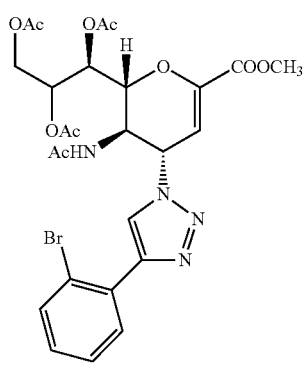

Purification by silica gel chromatography using hexane:acetone (3:2) yielded (88%) of pure IE1257-75. $^1$H NMR (400 MHz, CDCl$_3$): δ 1.85 (s, 3H, NAc), 2.06 (s, 3H, OAc), 2.08 (s, 3H, OAc), 2.09 (s, 3H, OAc), 3.84 (s, 3H, COOCH$_3$), 4.16-4.28 (m, 2H, H-5, H-9), 4.68 (dd, J=12.5, 2.6 Hz, 1H, H-9'), 4.91 (dd, J=10.7, 1.8 Hz, 1H, H-6), 5.43 (ddd, J=6.7, 5.6, 2.6 Hz, 1H, H-8), 5.53 (dd, J=5.8, 1.7 Hz, 1H, H-7), 6.00 (dd, J=9.9, 2.5 Hz, 1H, H-4), 6.11 (d, J=2.2 Hz, 1H, H-3), 6.59 (d, J=8.4 Hz, 1H, NH), 7.20 (ddd, J=8.1, 7.3, 1.6 Hz, 1H, PH—H), 7.40 (td, J=7.5, 1.3 Hz, 1H, Ph-H), 7.63 (dd, J=8.0, 1.2 Hz, 1H, Ph-H), 7.96 (dd, J=7.9, 1.7 Hz, 1H, Ph-H), 8.22 (s, 1H, triazole-CH); $^{13}$C NMR (101 MHz, CDCl$_3$) (20.80, 20.95 (3 OCOCH$_3$), 23.13 (NHCOCH$_3$), 49.56 (C-5), 52.75 (COOCH$_3$), 57.49 (C-4), 62.10 (C-9), 67.81 (C-7), 70.62 (C-8), 76.10 (C-6), 107.03 (C-3), 121.42 (Ph q carbon), 122.66 (Ph), 127.76 (Ph), 129.75 (Ph), 130.65 (Ph), 133.59 (triazole-C5), 145.61 (triazole-C4), 145.94 (C-2), 161.33 (COOCH$_3$), 170.15, 170.29, 170.71, 171.09 (NHCOCH$_3$, 3 OCOCH$_3$).

Sodium 5-acetamido-2,6-anhydro-4-(4-(2-bromophenyl)-[1,2,3,]triazol-1-yl)-3,4,5-trideoxy-D-glycero-D-galacto-non-2-enonate (IE1257-84)

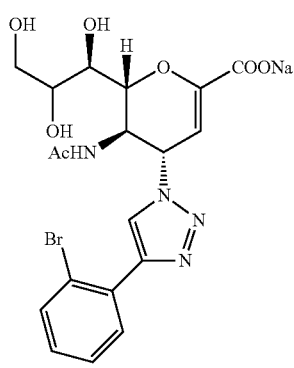

Yield=89%. $^1$H NMR (400 MHz, D$_2$O): δ 1.93 (s, 3H, NAc), 3.62-3.77 (m, 2H, H-7, H-9), 3.92 (dd, J=12.0, 2.7 Hz, 1H, H-9'), 4.02 (ddd, J=9.2, 6.2, 2.7 Hz, 1H, H-8), 4.49 (dd, J=10.9, 9.6 Hz, 1H, H-5), 4.60 (dd, J=10.9, 1.3 Hz, 1H, H-6), 5.58 (dd, J=9.7, 2.3 Hz, 1H, H-4), 5.92 (d, J=2.3 Hz, 1H, H-3), 7.36 (ddd, J=7.9, 7.3, 1.7 Hz, 1H, Ph-H), 7.49 (td, J=7.6, 1.3 Hz, 1H, Ph-H), 7.69 (dd, J=7.8, 1.7 Hz, 1H, Ph-H), 7.77 (dd, J=8.1, 1.2 Hz, 1H, Ph-H), 8.45 (s, 1H, triazole-CH); $^{13}$C NMR (101 MHz, D$_2$O): δ 21.77 (NHCOCH$_3$), 48.68 (C-5), 60.07 (C-4), 63.10 (C-9), 68.11 (C-7), 69.75 (C-8), 75.42 (C-6), 101.91 (C-3), 121.49 (Ph q carbon), 123.72 (Ph), 127.90 (Ph), 129.16 (Ph), 130.16 (Ph q carbon), 130.42 (Ph), 130.71 (Ph), 133.42 (triazole-C5), 145.89 (triazole-C4), 150.39 (C-2), 168.78 (COONa), 173.54 (NHCOCH$_3$).

Methyl 5-acetamido-7,8,9-tri-O-acetyl-2,6-anhydro-3,4,5-trideoxy-4-(4-(2-methoxycarbonyl)phenyl)-[1,2,3,]triazol-1-yl)-D-glycero-D-galacto-non-2-enonate (IE1398-25)

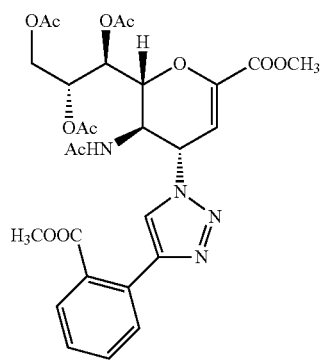

Purification by silica gel chromatography using hexane:acetone (4:3) yielded (91%) of pure IE1398-25. $^1$H NMR (400 MHz, CDCl$_3$): δ 1.76 (s, 3H, NAc), 2.02 (s, 3H, OAc), 2.04 (s, 3H, OAc), 2.05 (s, 3H, OAc), 3.75 (s, 3H, Ph-COOCH$_3$), 3.80 (s, 3H, C2-COOCH$_3$), 4.17 (dd, J=12.4, 7.1 Hz, 1H, H-9), 4.31 (q, J=9.8 Hz, 1H, H-5), 4.69 (dd, J=12.5, 2.8 Hz, 1H. H-9'), 4.78 (d, J=10.3 Hz, 1H, H-6), 5.38 (ddd, J=7.6, 5.4, 2.8 Hz, 1H, H-8), 5.52 (dd, J=5.0, 1.9 Hz, 1H, H-7), 5.78 (dd, J=10.2, 2.5 Hz, 1H, H-4), 6.03 (d, J=2.4 Hz, 1H, H-3), 7.13 (d, J=8.9 Hz, 1H, NH), 7.38 (t, J=7.8 Hz, 1H, Ph-H), 7.50 (td, J=7.7, 1.4 Hz, 1H, Ph-H), 7.65 (d, J=7.7 Hz, 1H, Ph-H), 7.76 (d, J=7.6 Hz, 1H, Ph-H), 7.84 (s, 1H, triazole-CH); $^{13}$C NMR (101 MHz, CDCl$_3$) δ 20.72, 20.79, 20.91 (3 OCOCH$_3$), 22.80 (NHCOCH$_3$), 48.65 (C-5), 52.29, 52.66 (2 COOCH$_3$), 57.96 (C-4), 62.23 (C-9), 67.78 (C-7), 70.91 (C-8), 76.66 (C-6), 107.37 (C-3), 122.06 (Ph), 128.35 (Ph), 129.85 (Ph), 129.99 (Ph q carbon), 130.15 (Ph q carbon), 130.35 (Ph), 131.62 (triazole-C5), 145.79 (triazole-C4), 145.89 (C-2), 161.36 (C2-COOCH$_3$), 168.39 (Ph-COOCH$_3$), 170.07, 170.27, 170.76, 171.02 (NHCOCH$_3$, 3 OCOCH$_3$); LRMS [C$_{28}$H$_{32}$N$_4$O$_{12}$] (m/z): (+ve ion mode) 639.3 [M+Na]$^+$.

Sodium 5-acetamido-2,6-anhydro-3,4,5-trideoxy-4-(4-(2-methoxycarbonyl)phenyl)-[1,2,3,]triazol-1-yl)-D-glycero-D-galacto-non-2-enonate (IE1398-33)

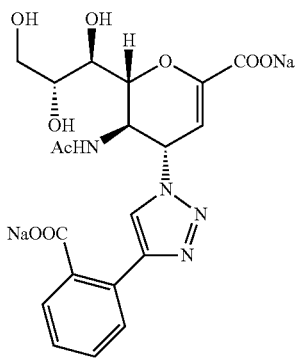

IE1398-33

Yield=68%. $^1$H NMR (400 MHz, D$_2$O): δ 1.94 (s, 3H, NAc), 3.66 (dd, J=12.2, 6.0 Hz, 1H, H-9), 3.72 (dd, J=9.8, 1.4 Hz, 1H, H-7), 3.93 (dd, J=12.0, 2.9 Hz, 1H, H-9'), 4.03 (ddd, J=9.4, 6.4, 2.7 Hz, 1H, H-8), 4.47 (t, J=10.3 Hz, 1H, H-5), 4.61 (dd, J=10.9, 1.4 Hz, 1H, H-6), 5.59 (dd, J=9.5, 2.1 Hz, 1H, H-4), 5.95 (d, J=2.2 Hz, 1H, H-3), 7.43-7.55 (m, 3H, 3 Ph-H), 7.75 (dd, J=6.6, 1.5 Hz, 1H, Ph-H), 8.18 (s, 1H, triazole-CH); $^{13}$C NMR (101 MHz, D$_2$O): δ 21.76 (NHCOCH$_3$), 48.80 (C-5), 59.69 (C-4), 63.10 (C-9), 68.13 (C-7), 69.77 (C-8), 75.40 (C-6), 102.22 (C-3), 122.33 (triazole-C5), 125.00 (Ph q carbon), 126.44 (Ph), 128.30 (Ph), 128.57 (Ph), 128.79 (Ph), 138.95 (Ph q carbon), 146.15 (triazole-C4), 150.22 (C-2), 168.85 (C2-COONa), 173.80 (NHCOCH$_3$), 178.10 (Ph-COONa); LRMS [C$_{20}$H$_{20}$N$_4$Na$_2$O$_9$] (m/z): (+ve ion mode) 528.8 [M+Na]$^+$.

Methyl 7,8,9-tri-O-acetyl-3,4,5-trideoxy-3-fluoro-5-isobutyramido-4-(4-methoxymethyl-[1,2,3,]triazol-1-yl)-D-erythro-3-L-gluco-non-2-ulopyranosylonate fluoride (IE1257-22)

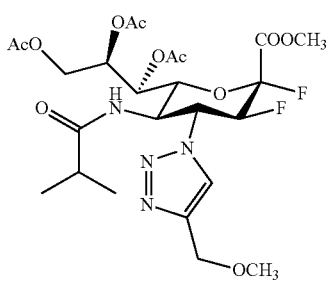

IE1257-22

Purification by silica gel chromatography using hexane/acetone (3:2) yielded (57 mg, 81%) of pure 10. $^1$H NMR (400 MHz, CDCl$_3$): δ 0.96-1.01 (m, 6H, isobut-2CH$_3$), 2.01 (s, 3H, OAc), 2.09 (s, 3H, OAc), 2.13 (s, 3H, OAc), 2.23 (dq, J=13.0, 6.8 Hz, 1H, isobut-CH), 3.36 (s, 3H, OCH$_3$), 3.90-3.96 (m, 4H, COOCH$_3$, H-5), 4.19 (dd, J=12.6, 4.6 Hz, 1H, H-9), 4.27 (dd, J=12.6, 2.5 Hz, 1H, H-9'), 4.54 (s, 2H, OCH$_2$), 4.99-5.30 (m, 3H, H-3, H-6, H-7), 5.37 (ddd, J=8.6, 4.6, 2.4 Hz, 1H, H-8), 6.19-6.29 (m, 2H, H-4, NH), 7.60 (s, 1H, triazole-CH); $^{13}$C NMR (100 MHz, CDCl$_3$): δ 18.86 (isobut-CH$_3$), 19.32 (isobut-CH$_3$), 20.59, 20.75, 20.79 (3 OCOCH$_3$), 35.53 (isobut-CH), 50.84 (d, J=5.8 Hz, C-5), 53.62 (COOCH$_3$), 58.34 (OCH$_3$), 59.00-59.40 (m, C-4), 61.86 (C-9), 65.50 (OCH$_2$), 67.08 (C-7), 68.29 (C-8), 71.51 (C-6), 90.64 (dd, J=196.1, 30.3 Hz, C-3), 105.58 (dd, J=230.3, 26.8 Hz, C-2), 124.52 (triazole-CH), 144.83 (triazole-q carbon), 164.51 (d, J=32.9 Hz, COOCH$_3$), 169.56, 170.41, 170.69 (3 OCOCH$_3$), 178.35 (isobut-CO); $^{19}$F NMR (376 MHz, CDCl$_3$): δ –118.67 (d, J=14.0 Hz, F–2α), –197.42 (d, J=13.2 Hz, F-3β); LRMS [C$_{24}$H$_{34}$F$_2$N$_4$O$_{11}$] (m/z): (+ve ion mode) 615.3 [M+Na]$^+$.

3,4,5-Trideoxy-3-fluoro-5-isobutyramido-4-(4-methoxymethyl-[1,2,3,]triazol-1-yl)-D-erythro-β-L-gluco-non-2-ulopyranosonic fluoride (IE1257-24)

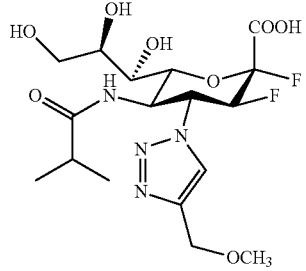

IE1257-54

$^1$H NMR (400 MHz, D$_2$O): δ 0.81 (d, J=6.9 Hz, 3H, isobut-CH$_3$), 0.94 (d, J=6.9 Hz, 3H, isobut-CH$_3$), 2.35 (p, J=6.9 Hz, 1H, isobut-CH), 3.38 (s, 3H, OCH$_3$), 3.54 (d, J=9.2 Hz, 1H, H-7), 3.61 (m, 1H, H-9), 3.78-3.91 (m, 2H, H-8, H-9'), 4.52-4.76 (m, 3H, OCH$_2$, H-6), 4.85 (m, 1H, H-5), 5.32 (ddd, J=49.5, 13.7, 9.7 Hz, 1H, H-3), 5.75 (q, J=11.2 Hz, 1H, H-4), 8.28 (s, 1H, triazole-CH); $^{13}$C NMR (100 MHz, D$_2$O): δ 18.11 (isobut-CH$_3$), 18.65 (isobut-CH$_3$), 34.87 (isobut-CH), 48.15 (d, J=6.1 Hz, C-5), 57.26 (OCH$_3$), 63.16 (C-9), 63.18-63.58 (m, C-4), 64.13 (OCH$_2$), 67.85 (C-7), 69.83 (C-8), 73.73 (d, J=3.3 Hz, C-6), 90.22 (dd, J=190.9, 32.6 Hz, C-3), 106.79 (dd, J=224.1, 27.8 Hz, C-2), 124.89 (triazole-CH), 144.09 (trizaole-q C), 169.21 (d, J=30.7 Hz, COOH), 180.88 (isobut-CO); $^{19}$F NMR (376 MHz, D$_2$O): δ –112.75 (d, J=13.8 Hz, F-2α), –199.41 (d, J=14.3 Hz, F-3β); LRMS [C$_{17}$H$_{25}$F$_2$N$_4$NaO$_8$] (m/z): (+ve ion mode) 496.8 [M+Na]$^+$; HRMS (API) (m/z): [M+1]$^+$ calcd for C$_{17}$H$_{26}$F$_2$N$_4$O$_8$[M+1]$^+$453.1791. found, 453.1810.

Methyl 5-acetamido-7,8,9-tri-O-acetyl-2,6-anhydro-4-(1-cyano-2H-isoindol-2-yl)-3,4,5-trideoxy-D-glycero-D-galacto-non-2-enonate (IE889-76)

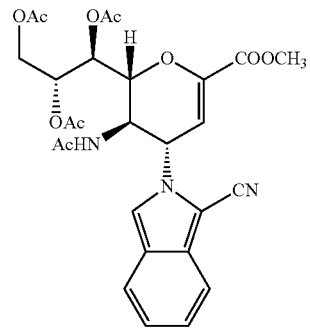

IE889-76

$^1$H NMR (300 MHz, CDCl$_3$): δ 1.60 (s, 3H, NAc), 1.82 (s, 6H, 2 OAc), 1.84 (s, 3H, OAc), 3.60 (s, 3H, COOCH$_3$), 3.96 (dd, J=12.7, 7.0 Hz, 1H, H-9), 4.19 (q, J=9.9 Hz, 1H, H-5), 4.40-4.50 (m, 2H, H-6, H-9'), 5.16 (ddd, J=7.5, 6.0, 2.4 Hz, 1H, H-8); 5.22-5.33 (m, 2H, H-4, H-7), 5.86 (d, J=1.6

Hz, 1H, H-3), 6.20 (d, J=9.6 Hz, 1H, NHAc), 6.84 (m, 1H, Ar—H), 6.99 (m, 1H, Ar—H), 7.26 (s, 1H, Ar—H-3'), 7.37 (m, 2H, Ar—H-4', Ar—H-7'); $^{13}$H NMR (75 MHz, CDCl$_3$): δ 20.76, 20.92 (3 OCO$\underline{C}$H$_3$), 22.97 (NHCO$\underline{C}$H$_3$), 49.26 (C-5), 52.79 (COO$\underline{C}$H$_3$), 58.00 (C-4), 62.08 (C-9), 67.67 (C-7), 70.86 (C-8), 77.06 (C-6), 93.82 (Ar—$\underline{C}$—CN), 107.66 (C-3), 114.69 (CN), 117.55 (Ar), 117.78 (Ar), 121.14 (Ar), 123.23 (Ar), 124.63 (Ar q carbon), 126.08 (Ar), 131.60 (Ar q carbon), 146.63 (C-2), 161.29 ($\underline{C}$OOCH$_3$), 170.17, 170.30, 170.63 (NH$\underline{C}$OCH$_3$, 3 O$\underline{C}$OCH$_3$); LRMS [C$_{27}$H$_{29}$N$_3$O$_{10}$] (m/z): (+ve ion mode) 578.1 [M+Na]$^+$.

Sodium 5-acetamido-2,6-anhydro-4-(1-cyano-2H-isoindol-2-yl)-3,4,5-trideoxy-D-glycero-D-galacto-non-2-enonate (IE889-80)

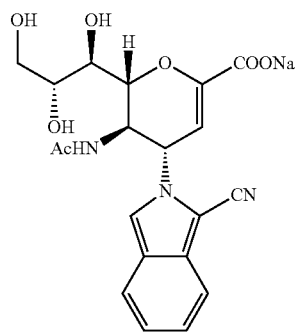

IE889-80

$^1$H NMR (300 MHz, D$_2$O): δ 1.91 (s, 3H, NAc), 3.61-3.77 (m, 2H, H-7, H-9), 3.94 (dd, J=11.9, 2.6 Hz, 1H, H-9'), 4.05 (ddd, J=9.2, 6.2, 2.6 Hz, 1H, H-8), 4.50 (m, 1H, H-5), 4.64 (d, J=11.0 Hz, 1H, H-6), 5.47 (dd, J=9.4, 2.3 Hz, 1H, H-4), 5.96 (d, J=2.3 Hz, 1H, H-3), 7.21 (m, 1H, Ar—H), 7.37 (ddd, J=8.9, 6.7, 1.1 Hz, 1H, Ar—H), 7.65-7.87 (m, 3H, Ar—H-3', Ar—H-4', Ar—H-7'); $^{13}$C NMR (75 MHz, D$_2$O): δ 21.77 (NHCO$\underline{C}$H$_3$), 49.83 (C-5), 59.20 (C-4), 63.08 (C-9), 68.09 (C-7), 69.77 (C-8), 75.41 (C-6), 92.08 (Ar—$\underline{C}$—CN), 103.30 (C-3), 115.30 (CN), 117.35 (Ar), 119.65 (Ar), 121.36 (Ar), 122.82 (Ar), 124.09 (Ar q carbon), 125.99 (Ar), 132.03 (Ar q carbon), 150.56 (C-2), 168.78 (COONa), 173.36 (NH$\underline{C}$OCH$_3$); LRMS [C$_{20}$H$_{20}$N$_3$NaO$_7$] (m/z): (+ve ion mode) 460.1 [M+Na]$^+$; HRMS (API) (m/z): [M+Na]$^+$ calcd for C$_{20}$H$_{20}$N$_3$Na$_2$O$_7$[M+Na]$^+$460.1091. found, 460.1097.

Methyl 7,8,9-tri-O-acetyl-2,6-anhydro-4-(1-cyano-2H-isoindol-2-yl)-3,4,5-trideoxy-5-isobutyramido-D-glycero-D-galacto-non-2-enonate (IE889-92)

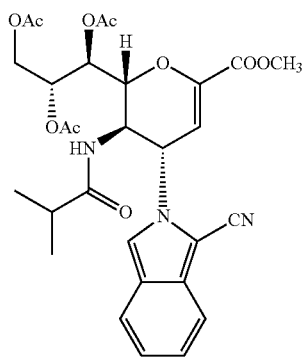

IE889-92

$^1$H NMR (300 MHz, CDCl$_3$): δ 0.92 (d, J=6.8 Hz, 3H, isobutyryl-CH$_3$), 1.00 (d, J=6.8 Hz, 3H, isobutyryl-CH$_3$), 2.07 (s, 3H, OAc), 2.09 (s, 3H, OAc), 2.10 (s, 3H, OAc), 2.27 (m, 1H, isobutyryl-CH), 3.86 (s, 3H, COOCH$_3$), 4.23 (dd, J=12.4, 6.6 Hz, 1H, H-9), 4.50 (m, 1H, H-5), 4.68 (dd, J=12.5, 2.7 Hz, 1H, H-9'), 4.77 (d, J=10.6 Hz, 1H, H-6), 5.40 (m, 1H, H-8), 5.51 (dd, J=5.6, 1.6 Hz, 1H, H-7), 5.62 (dd, J=9.7, 2.4 Hz, 1H, H-4), 6.15 (d, J=2.4 Hz, 1H, H-3), 6.24 (d, J=9.4 Hz, 1H, NH), 7.11 (dd, J=8.6, 6.7 Hz, 1H, Ar—H), 7.28 (dd, J=8.4, 6.6 Hz, 1H, Ar—H), 7.50 (s, 1H, Ar—H-3'), 7.60-7.64 (m, 2H, Ar—H-4', Ar—H-7'); $^{13}$H NMR (75 MHz, CDCl$_3$): δ 18.77, 19.05 (isobutyryl-2CH$_3$), 20.69, 20.73, 20.90 (3 OCO$\underline{C}$H$_3$), 35.51 (isobutyryl-CH), 49.11 (C-5), 52.78 (COO$\underline{C}$H$_3$), 57.88 (C-4), 62.05 (C-9), 67.61 (C-7), 70.80 (C-8), 77.01 (C-6), 93.83 (Ar—$\underline{C}$—CN), 107.56 (C-3), 114.80 (CN), 117.58 (Ar), 117.81 (Ar), 121.20 (Ar), 123.22 (Ar), 124.66 (Ar q carbon), 126.15 (Ar), 131.56 (Ar q carbon), 146.50 (C-2), 161.31 ($\underline{C}$OOCH$_3$), 170.10, 170.14, 170.57 (3 O$\underline{C}$OCH$_3$), 177.07 (isobutyryl-CO); LRMS [C$_{29}$H$_{33}$N$_3$O$_{10}$] (m/z): (+ve ion mode) 606.4 [M+Na]$^+$.

Sodium 2,6-anhydro-4-(1-cyano-2H-isoindol-2-yl)-3,4,5-trideoxy-5-isobutyramido-D-glycero-D-galacto-non-2-enonate (IE889-99)

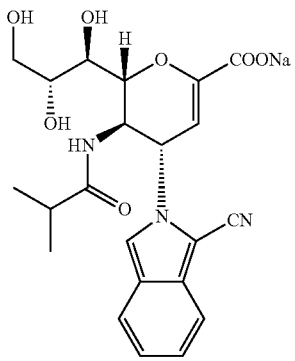

IE889-99

$^1$H NMR (300 MHz, D$_2$O): δ 0.88 (d, J=6.9 Hz, 3H, isobutyryl-CH$_3$), 0.97 (d, J=6.9 Hz, 3H, isobutyryl-CH$_3$), 2.44 (m, 1H, isobutyryl-CH), 3.62-3.75 (m, 2H, H-7, H-9), 3.93 (dd, J=12.0, 2.7 Hz, 1H, H-9'), 4.04 (ddd, J=9.3, 6.3, 2.6 Hz, 1H, H-8), 4.56-4.66 (m, 2H, H-5, H-6), 5.47 (dd, J=9.6, 2.4 Hz, 1H, H-4), 5.95 (d, J=2.2 Hz, 1H, H-3), 7.20 (ddd, J=7.8, 6.8, 1.0 Hz, 1H, Ar—H), 7.36 (ddd, J=8.3, 6.8, 1.0 Hz, 1H, Ar—H), 7.70 (dd, J=8.6, 1.1 Hz, 1H, Ar—H), 7.74-7.87 (m, 2H, 2 Ar—H); $^{13}$C NMR (75 MHz, D$_2$O): δ 18.16, 18.59 (isobutyryl-2CH$_3$), 35.06 (isobutyryl-CH), 49.13 (C-5), 59.30 (C-4), 63.07 (C-9), 68.20 (C-7), 69.81 (C-8), 75.45 (C-6), 92.08 (Ar—$\underline{C}$—CN), 103.34 (C-3), 115.47 (CN), 117.33 (Ar), 120.04 (Ar), 121.38 (Ar), 122.81 (Ar), 124.04 (Ar q carbon), 126.01 (Ar), 132.04 (Ar q carbon), 150.37 (C-2), 168.87 (COONa), 180.37 (isobutyryl-CO); LRMS [C$_{22}$H$_{24}$N$_3$NaO$_7$] (m/z): (+ve ion mode) 488.1 [M+Na]$^+$; HRMS (API) (m/z): [M+Na]$^+$ calcd for C$_{22}$H$_{24}$N$_3$Na$_2$O$_7$[M+Na]$^+$488.1404. found, 488.1400.

Methyl 7,8,9-tri-O-acetyl-2,6-anhydro-4-(1-cyano-2H-isoindol-2-yl)-3,4,5-trideoxy-5-(2,2,2-trifluoroacetamido)-D-glycero-D-galacto-non-2-enonate (IE927-93)

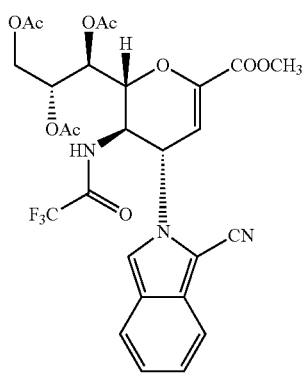

IE927-93

$^1$H NMR (300 MHz, CDCl$_3$): δ 2.07 (s, 3H, OAc), 2.08 (s, 3H, OAc), 2.10 (s, 3H, OAc), 3.86 (s, 3H, COOCH$_3$), 4.22 (dd, J=12.5, 6.6 Hz, 1H, H-9), 4.54 (q, J=9.9 Hz, 1H, H-5), 4.68 (dd, J=12.5, 2.6 Hz, 1H, H-9'), 4.82 (dd, J=10.6, 1.9 Hz, 1H, H-6), 5.43 (td, J=6.0, 5.5, 2.6 Hz, 1H, H-8), 5.52 (dd, J=5.6, 1.8 Hz, 1H, H-7), 5.62 (dd, J=9.7, 2.4 Hz, 1H, H-4), 6.17 (d, J=2.4 Hz, 1H, H-3), 7.13 (ddd, J=7.9, 6.8, 1.0 Hz, 1H, Ar—H), 7.28 (ddd, J=8.4, 6.7, 1.0 Hz, 1H, Ar—H), 7.52 (s, 1H, Ar—H-3'), 7.58-7.69 (m, 2H, Ar—H-4', Ar—H-7'), 7.91 (d, J=9.6 Hz, 1H, NH); $^{13}$H NMR (75 MHz, CDCl$_3$): δ 20.50, 20.71, 20.91 (3 OCOCH$_3$), 49.81 (C-5), 52.93 (COOCH$_3$), 57.45 (C-4), 61.93 (C-9), 67.46 (C-7), 70.64 (C-8), 76.40 (C-6), 93.61 (Ar—C—CN), 107.14 (C-3), 113.24-117.05 (CF$_3$), 114.37 (CN), 117.73 (Ar), 117.80 (Ar), 121.08 (Ar), 123.65 (Ar), 124.93 (Ar q carbon), 126.55 (Ar), 131.85 (Ar q carbon), 146.73 (C-2), 157.56 (q, J$_{C,F}$=38.8 Hz, COCF$_3$), 161.03 (COOCH$_3$), 169.91, 170.38, 170.71 (3 OCOCH$_3$); LRMS [C$_{27}$H$_{26}$—F$_3$N$_3$O$_{10}$] (m/z): (+ve ion mode) 632.1 [M+Na]$^+$.

Sodium 2,6-anhydro-4-(1-cyano-2H-isoindol-2-yl)-3,4,5-trideoxy-5-(2,2,2-trifluoroacetamido)-D-glycero-D-galacto-non-2-enonate (IE927-99)

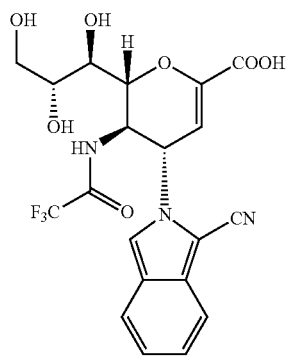

IE927-99

$^1$H NMR (300 MHz, D$_2$O): δ δ 3.60-3.75 (m, 2H, H-7, H-9), 3.93 (dd, J=11.9, 2.7 Hz, 1H, H-9'), 4.07 (ddd, J=9.4, 6.4, 2.6 Hz, 1H, H-8), 4.64-4.74 (m, 2H, H-5, H-6), 5.57 (dd, J=9.4, 2.3 Hz, 1H, H-4), 6.00 (d, J=2.3 Hz, 1H, H-3), 7.21 (m, 1H, Ar—H), 7.36 (m, 1H, Ar—H), 7.69 (d, J=8.6 Hz, 1H, Ar—H), 7.77 (d, J=8.5 Hz, 1H, Ar—H), 7.84 (s, 1H, Ar—H-3'); $^{13}$C NMR (75 MHz, D$_2$O): 50.48 (C-5), 58.73 (C-4), 63.00 (C-9), 68.08 (C-7), 69.66 (C-8), 75.05 (C-6), 91.94 (Ar—C—CN), 103.21 (C-3), 109.60-118.88 (CF$_3$), 115.01 (CN), 117.34 (Ar), 121.36 (Ar), 123.02 (Ar), 124.19 (Ar q carbon), 126.23 (Ar), 132.12 (Ar q carbon), 150.62 (C-2), 158.20 (q, J$_{C,F}$=38.8 Hz, COCF$_3$), 168.44 (COONa); LRMS [C$_{20}$H$_{17}$F$_3$N$_3$NaO$_7$] (m/z): (+ve ion mode) 514.1 [M+Na]$^+$, 492.2; HRMS (API) (m/z): [M+Na]$^+$ calcd for C$_{20}$H$_{17}$F$_3$N$_3$Na$_2$O$_7$[M+Na]$^+$514.0830. found, 514.0836.

Methyl 5-acetamido-7,8,9-tri-O-acetyl-2,6-anhydro-3,4,5-trideoxy-4-(1H-tetrazol-1-yl)-D-glycero-D-galacto-non-2-enonate (IE832-86)

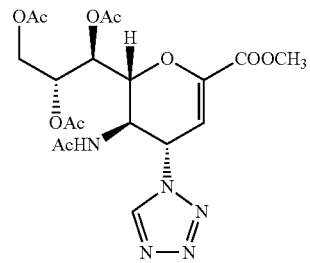

IE832-86

$^1$H NMR (300 MHz, CDCl$_3$): δ 1.95 (s, 3H, NAc), 2.06 (s, 3H, OAc), 2.09 (s, 3H, OAc), 2.10 (s, 3H, OAc), 3.84 (s, 3H, COOCH$_3$), 4.02 (m, 1H, H-5), 4.22 (dd, J=12.6, 6.4 Hz, 1H, H-9), 4.63 (dd, J=12.5, 2.6 Hz, 1H, H-9'), 4.95 (dd, J=10.5, 1.8 Hz, 1H, H-6), 5.38 (td, J=6.2, 2.6 Hz, 1H, H-8), 5.49 (dd, J=5.9, 1.8 Hz, 1H, H-7), 6.05 (d, J=2.5 Hz, 1H, H-3), 6.11 (dd, J=9.8, 2.5 Hz, 1H, H-4), 6.67 (d, J=8.2 Hz, 1H, NH), 8.70 (s, 1H, tetrazole-CH); $^{13}$H NMR (75 MHz, CDCl$_3$): δ 20.72, 20.75, 20.91 (3 OCOCH$_3$), 23.13 (NHCOCH$_3$), 49.72 (C-5), 52.87 (COOCH$_3$), 55.92 (C-4), 61.93 (C-9), 67.62 (C-7), 70.50 (C-8), 75.70 (C-6), 105.19 (C-3), 140.84 (Tetrazole-C5), 146.64 (C-2), 161.07 (COOCH$_3$), 170.17, 170.27, 170.63, 171.54 (NHCOCH$_3$, 3 OCOCH$_3$); LRMS [C$_{19}$H$_{25}$N$_5$O$_{10}$] (m/z): (+ve ion mode) 506.5 [M+Na]$^+$.

Sodium 5-acetamido-2,6-anhydro-3,4,5-trideoxy-4-(1H-tetrazol-1-yl)-D-glycero-D-galacto-non-2-enonate (IE832-98)

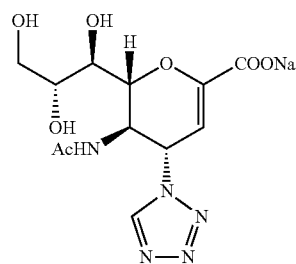

IE832-98

¹H NMR (300 MHz, D₂O): δ 1.94 (s, 3H, NAc), 3.65-3.74 (m, 2H, H-7, H-9), 3.92 (dd, J=11.9, 2.7 Hz, 1H, H-9'), 4.02 (ddd, J=9.3, 6.2, 2.7 Hz, 1H, H-8), 4.44 (dd, J=10.9, 9.7 Hz, 1H, H-5), 4.62 (dd, J=11.0, 1.4 Hz, 1H, H-6), 5.73 (dd, J=9.6, 2.3 Hz, 1H, H-4), 5.88 (d, J=2.3 Hz, 1H, H-3); ¹³C NMR (75 MHz, D₂O): δ 21.63 (NHCOCH₃), 48.44 (C-5), 58.77 (C-4), 63.04 (C-9), 67.99 (C-7), 69.67 (C-8), 75.29 (C-6), 100.61 (C-3), 143.99 (Tetrazole-C5), 150.85 (C-2), 168.53 (COOCH₃), 173.82 (NHCOCH₃); LRMS [C₁₂H₁₆N₅NaO₇] (m/z): (+ve ion mode) 388.4 [M+Na]⁺; HRMS (API) (m/z): [M+Na]⁺ calcd for C₁₂H₁₆N₅Na₂O₇ [M+Na]⁺ 388.083964. found, 388.084945.

Methyl 7,8,9-tri-O-acetyl-2,6-anhydro-3,4,5-trideoxy-5-isobutyramido-4-(1H-tetrazol-1-yl)-D-glycero-D-galacto-non-2-enonate (IE889-36)

¹H NMR (300 MHz, CDCl₃): δ 1.05 (d, J=6.9 Hz, 6H, isobutyramido-2CH₃), 2.01 (s, 3H, OAc), 2.05 (s, 6H, 2OAc), 2.34 (m, 1H, isobutyramido-CH), 3.81 (s, 3H, COOCH₃), 4.01 (m, 1H, H-5), 4.18 (dd, J=12.5, 6.3 Hz, 1H, H-9), 4.60 (dd, J=12.6, 2.6 Hz, 1H, H-9'), 5.03 (dd, J=10.5, 1.7 Hz, 1H, H-6), 5.32 (td, J=6.1, 2.5 Hz, 1H, H-8), 5.46 (dd, J=5.9, 1.8 Hz, 1H, H-7), 6.03 (d, J=2.4 Hz, 1H, H-3), 6.14 (dd, J=9.8, 2.5 Hz, 1H, H-4), 6.94 (d, J=8.1 Hz, 1H, NH), 8.65 (s, 1H, tetrazole-CH); ¹³H NMR (75 MHz, CDCl₃): δ 18.85, 19.27 (isobutyramido-2CH₃), 20.66, 20.84 (3 OCOCH₃), 35.56 (isobutyramido-CH), 49.69 (C-5), 52.79 (COOCH₃), 55.77 (C-4), 61.91 (C-9), 67.49 (C-7), 70.51 (C-8), 75.64 (C-6), 105.15 (C-3), 140.81 (Tetrazole-C5), 146.70 (C-2), 161.18 (COOCH₃), 170.04, 170.15, 170.58 (3 OCOCH₃), 178.53 (isobutyramido-CO); LRMS [C₂₁H₂₉N₅O₁₀] (m/z): (+ve ion mode) 534.3 [M+Na]⁺; HRMS (API) (m/z): [M+Na]⁺ calcd for C₂₁H₂₉N₅NaO₁ [M+Na]⁺534.180663. found, 543.1788531.

Sodium 2,6-anhydro-3,4,5-trideoxy-5-isobutyramido-4-(H-tetrazol-1-yl)-D-glycero-D-galacto-non-2-enonate (IE889-42)

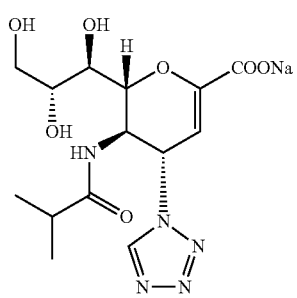

IE889-42

¹H NMR (300 MHz, D₂O): δ 0.99-1.04 (m, 6H, isobutyramido-2CH₃), 2.46 (m, 1H, isobutyramido-CH), 3.59-3.75 (m, 2H, H-7, H-9), 3.93 (dd, J=12.0, 2.6 Hz, 1H, H-9'), 4.03 (ddd, J=9.7, 6.2, 2.6 Hz, 1H, H-8), 4.49 (dd, J=10.9, 9.7 Hz, 1H, H-5), 4.65 (dd, J=10.9, 1.2 Hz, 1H, H-6), 5.76 (dd, J=9.7, 2.3 Hz, 1H, H-4), 5.88 (d, J=2.2 Hz, 1H, H-3), 9.38 (s, 1H, tetrazole-CH); LRMS [C₁₄H₂₀N₅NaO₇] (m/z): (+ve ion mode) 416.0 [M+Na]⁺; HRMS (API) (m/z): [M+Na]⁺ calcd for C₁₄H20N₅Na₂O₇ [M+Na]⁺416.115264. found, 416.116886.

Biology

Cells and Virus:

A549 cells (adenocarcinomic human alveolar basal epithelial cells) were provided by the European Collection of Cell Cultures (86012804-1VL, Sigma Aldrich). Cells were propagated in Dulbecco's Modified Eagle Medium (DMEM) (Lonza, Basel, Switzerland) supplemented with 1% Glutamine (200 mM) and 5% foetal bovine serum. For infection and post-infection procedures, A549 cells were maintained in DMEM supplemented with 1% Glutamine only. Normal human bronchial/tracheal epithelial (NHBE) cells (CC-2540, lot 313831, Lonza) were amplified in B-ALI™ growth medium (Lonza) and the same medium was used for infection and post-infection studies. LLC-MK2 cells (Rhesus monkey kidney, ATCC CCL-7) were cultured in Eagle's minimal essential medium (EMEM) (Lonza) supplemented with 1% Glutamine (200 mM) and 2% of heat-inactivated foetal bovine serum. During hPIV-3 infection and post-infection incubation, LLC-MK2 cells were maintained in EMEM supplemented with 1% glutamine. All cell lines were incubated at 37° C. in a humidified atmosphere of 5% C02.

hPIV-3 (strain C-243) was obtained from the American Type Culture Collection (ATCC, Manassas, Va.). The virus was propagated in LLC-MK2 cells with EMEM supplemented with glutamine (EMEM$_{inf}$) at 35° C. in a humidified atmosphere of 5% CO₂. Virus-containing culture supernatant was collected 3 to 4 days post-infection, while monitoring cytopathic effects, and clarified from cell debris by centrifugation (3,000 RCF for 15 min). Virus was concentrated at least 10 times using 30 kDa Amicon Ultra filter unit (Millipore, Billerica, Mass.) for use in Haemagglutination Inhibition (HI) assays. Neuraminidase Inhibition (NI) assays and STD-NMR experiments used virus that was PEG-precipitated and then purified as described above.

Clarified hPIV-3 supernatant was mixed with PEG6000 (8% final concentration) and NaCl (0.4 M final concentration) then incubated overnight at 4° C. under gentle agitation. PEG6000/hPIV-3 complex was pelleted by centrifugation at 3,000 RCF for 30 min at 4° C. The supernatant was discarded and a volume of GNTE buffer (200 mM glycine, 200 mM NaCl, 20 mM Tris-HCl, 2 mM EDTA, pH 7.4) corresponding to at least 1:40 of the initial virus suspension volume was used to resuspend the pellet overnight at 4° C. The virus suspension was homogenized by up and down pipetting followed by a mechanical disruption of the remaining virus aggregates using a douncer with "tight" pestle. The hPIV-3 homogenate was loaded on top of a 30%-60% non-linear sucrose gradient prepared in GNTE buffer and centrifuged at 100,000 RCF for 2 h 30 min at 4° C. without brake for deceleration. The virus was concentrated at the 30%-60% sucrose interface and then collected and stored at −80° C. for NI assays or at 4° C. for STD-NMR experiments.

hPIV-3 HN Inhibitors:

Compounds 2, 3, 5-10 were each provided as a lyophilized powder and then solubilized in sterile water to generate a 10 mM stock solution. Solutions were sonicated for 15 min to allow complete dissolution and then filter-sterilized. The stock solution was stored in a glass vial at −20° C. and freshly diluted in appropriate buffer before use.

For STD NMR experiments, stock solutions were prepared in $D_2O$ at 100 mM. Solutions were processed and stored as described above.

Recombinant HN Expression and Purification:

The HN protein was expressed using the Bac-to-Bac® baculovirus expression system (Invitrogen, Carlsbad, Calif.) based on a substantially modified literature procedure. Thus, the nucleotide sequence for a honeybee melittin signal peptide (HBM) was added downstream to the sequence encoding for the HN ectodomain (amino acids 125 to 572). This sequence (HBM+HN) was codon optimised for expression in Spodoptera frugiperda cells (Sf9) and ordered directly through the DNA2.0 gene synthesis service (DNA2.0, Menlo Park, Calif.) as a gene named HBM-HNhPIV-3$_{opt}$. HBM-HNhPIV-3$_{opt}$ was amplified by PCR and ligated into a pFastBacCT-TOPO® vector that provides an additional C-terminal 6-histidine tag (His-Tag) for purification and detection purposes.

The generation and amplification of recombinant baculovirus containing HBM-HNhPIV-3$_{opt}$ were performed according to the manufacturer's instructions. Sf9 cells (Invitrogen), cultured in Insect-XPRESS protein free insect cell medium (Lonza), were infected with high MOI of HBM-HNhPIV-3$_{opt}$ baculovirus. Four days post-infection the supernatant, containing recombinant HN, was collected to yield the highest protein expression. The supernatant was clarified by centrifugation (3,000 RCF for 15 min) to remove cell debris and then purified on a HisTrap excel 5 mL column (GE Healthcare life sciences, Buckinghamshire, England) following the manufacturer's protocol. Recombinant HN was eluted with 500 mM imidazole solution and collected fractions were assessed by a neuraminidase activity (NA) assay (see below). The most active fractions were pooled and concentrated with a 10 kDa Amicon Ultra filter unit (Millipore) to a final volume of 800 μL. An additional purification step was performed that employed fast protein liquid chromatography (Amersham Biosciences) over a Superdex 75 gel filtration column (GE Healthcare) at 4° C. and 1 mL fractions were collected with a Frac-920. Protein-containing fractions, as determined by monitoring fraction collection at 280 nm, were assessed in a NA assay as well as subjected to SDS-PAGE. Purified and concentrated recombinant HN protein was stored at 4° C.

Haemagglutination Inhibition Assay:

The HN inhibitors were assessed in duplicate in a U-bottom 96 well plate assay. Compounds were diluted in PBS as a 4× solution for each concentration tested (25 μL/well, 1× final). Each dilution was mixed with 4 haemagglutination units (HAU) of hPIV-3 (25 L/well, 1 HAU final) and incubated for 20 min at room temperature. The plate was transferred on ice and an equivalent volume (50 μL) of ice-cold 0.75% guinea pig red blood cells (Gp-RBC) or 1% human red blood cells (h-RBC) was added to each well. The plate was then incubated for 1 h 30 min at 4° C. before reading the extent of haemagglutination. The HI IC$_{50}$ was considered as the concentration of inhibitor that reduced the haemagglutinin activity (agglutination) by 50% compared to those of a non-treated virus suspension.

Neuraminidase Inhibition Assay

Purified hPIV-3, inhibitors and MUN were prepared and diluted in NA Reaction Buffer (NaOAc 50 mM, $CaCl_2$ 5 mM, pH 4.6). NA, employing different hPIV-3 dilutions, were initially measured to determine the lowest virus concentration to be used in the assays. The NA assays were performed with enough purified virus to obtain a maximal fluorescence signal at least 5 times higher than the background for the experiment to be considered statistically significant. Neuraminidase inhibition (NI) assays were done in triplicate. For each concentration tested, 2 μL of purified hPIV-3 and 4 μL of 2.5× inhibitor solution (1× final) was added to each well. The plate was kept at room temperature for 20 min before 4 μL of 5 mM 2'-(4-methylumbelliferyl)☐-D-N-acetylneuraminide (MUN) (2 mM final) was added to each well and then the plate incubated at 37° C. for 30 min with agitation (1000 rpm). The enzymatic reaction was stopped by the addition of 190 μL of glycine buffer (glycine 0.25 M, pH 10.4) to each well. A negative control was included by the addition of MUN to virus and then the enzymatic reaction stopped at t=0. Relative fluorescence (RF) was measured with a Victor 3 multilabel reader (PerkinElmer, Waltham, Mass.). Data were processed by background subtraction (negative control RF) and then analysed with GraphPadPrism 4 (GraphPad Software Inc., La Jolla, Calif.) to calculate IC$_{50}$ values (nonlinear regression (curve fit), Dose-response—inhibition, 3 parameter logistic). The concentration of inhibitor that reduced neuraminidase activity (relative fluorescence) by 50% compared to those of a non-treated virus suspension was considered to be the NI IC$_{50}$ value. $K_i$ values of inhibitors 6 and 10 were determined by enzyme kinetic experiments with whole hPIV-3 virus based on previously published procedures. Thus, neuraminidase activity was measured every 5 min over a 20 min period, at five substrate concentrations [S]: 2, 4, 8, 10 and 16 mM, and four inhibitor concentrations [I]: 0, 0.5, 2.5 and 5 μM for 10 or 0, 10, 20 and 60 μM for 6. All assays were performed in triplicate and the final data were fitted to the Michaelis-Menten equation for competitive inhibition using GraphPadPrism 4 (GraphPad Software Inc., La Jolla, Calif.) to determine the Michaelis-Menten constant ($K_m$), using data from the [I]=0 and variable [S] experiments, and $K_i$ values.

Virus Growth Inhibition Assay:

Before assessing the best inhibitors in cell-based assays, an MTT assay was performed to evaluate compound cytotoxicity. No cytotoxic effect was observed after incubation for 48 h of LLC-MK2 cells with 6, 8 and 10 at 30 μM, the highest concentration tested. Virus growth inhibition was assessed using a focus-forming assay by titration of progeny in the presence of 2 μM of 6, 8 and 10 in EMEM$_{inf}$ from a low MOI infected confluent LLC-MK2 monolayer in a 48 well plate format. Virus inoculum (100 FFU/well) was pre-incubated with 6, 8 and 10 for 20 min. Infection was performed in duplicate and continued for 1 h at 37° C. with gentle agitation every 15 min. Inocula were removed and replaced with 500 μL/well of each respective 2 μM compound dilution (in EMEM$_{inf}$).

A positive control for infection was included using the same conditions minus the compound. Virus proliferation on infected cell monolayers were maintained for 48 h at 37° C., 5% $CO_2$. Culture supernatants from duplicates were collected, pooled and clarified at 15,000 RCF for 10 min and stored at −80° C. Supernatants were diluted in EMEM$_{inf}$ by $10^{-3}$, $10^{-4}$ and $10^{-5}$ to avoid any remaining compound effect on the subsequent virus titration. Virus titrations were done in duplicate using the previously described conditions for virus infection. After 1 h, Avicel (FMC BioPolymer, Philadelphia, Pa.) in EMEM$_{inf}$ was directly added to the inoculum (1% final concentration) to restrict and localise virus proliferation. The plate was incubated for 36 to 40 h at 37° C., 5% $CO_2$ to allow focus formation. Avicel was gently removed and replaced with 3.7% Paraformaldehyde/PBS and the plate was then kept for 15 min at room temperature for virus inactivation and cell fixation. Cell monolayers were washed three times for 5 min each with PBS and then endogenous peroxidase inactivated with 0.3% $H_2O_2$/PBS for 30 min at 37° C. The plate was washed again three times for 5 min each with PBS and incubated with mouse monoclonal IgG anti-hPIV-3 HN (Fitzgerald, clone# M02122321, 2.0 mg/mL) at 1 µg/mL in 5% milk/PBS for 1 h at 37° C. Cell monolayers were washed 3 times for 5 min with 0.02% Tween20/PBS. Goat anti-Mouse-IgG(H+L)-HRP conjugate (BioRad, ref#170-6516) diluted at 1:1000 in 5% milk/PBS was added to each well and incubated for 1 h at 37° C. Cell monolayers were washed as previously described with 0.02% Tween20/PBS and then rinsed twice with PBS. Foci were revealed by adding TrueBlue solution (HRP substrate) on each well and incubating the plate for 1 h at 37° C. The TrueBlue solution was discarded and the plate rinsed twice with water then dried before being scanned (FIG. 2) and foci counted. The $IC_{50}$ value was considered as the concentration of inhibitor that reduced the progeny virus titre by 50% compared to a non-treated infected LLC-MK2 monolayer.

In situ ELISA:

In situ ELISA is a useful technique to evaluate virus growth inhibition. It measures, in one step, the expression level of hPIV-3 HN at the cell surface of an infected cell monolayer. The expression level is directly correlated to the ability of a non-immobilized virus to infect and re-infect target cells. Infection was performed on a confluent cell monolayer seeded in a 96 well plate. Virus (40 FFU/well) was pre-incubated for 20 min with compound 6 and 10 at a final concentration from 1000 µM to 0.001 µM as a 10-fold dilution series. Infection was done in triplicate and continued for 1 h at 37° C. with gentle agitation every 15 min. Inocula were removed and replaced with 200 µL/well of each respective compound dilution. A positive control for infection was incorporated by the use of identical experimental conditions, minus inhibitor. Infected cell monolayers were kept for 36-40 h at 37° C., 5% $CO_2$ for virus proliferation. Virus was inactivated and cells fixed by the direct addition of 100 µL of 11.1% paraformaldehyde/PBS. The plate was maintained at room temperature for 15 min and then washed 3 times for 5 min with PBS and then endogenous peroxidases were inactivated by treatment with 0.3% $H_2O_2$/PBS for 30 min at 37° C. The cell monolayers were washed and incubated with mouse monoclonal IgG anti-hPIV-3HN (Fitzgerald, clone# M02122321, 2.0 mg/mL) at 1 µg/mL in 5% milk/PBS for 1 h at 37° C. The wells were washed 3 times for 5 min with 0.02% Tween20/PBS. Goat anti-Mouse-IgG(H+L)-HRP conjugate (BioRad, ref#170-6516), diluted at 1:2000 in 5% milk/PBS, was added to each well and incubated for 1 h at 37° C. Cell monolayers were washed with 0.02% Tween20/PBS and then rinsed twice with PBS. BD OptEIATMB substrate (BD Biosciences, San Jose, Calif., 100 µL) was added to each well and the plate was then incubated at 37° C. The enzymatic reaction was stopped after 3-5 min by the addition of 50 µL of 0.6 M of $H_2SO_4$ per well. Raw data were obtained by reading the absorbance (OD) of each well at 450 nm for 0.1 sec with a Victor 3 multilabel reader (PerkinElmer, Waltham, Mass.). Final ODs were obtained by subtraction of the negative control (non-infected cells) OD from the initial OD reading and the data analysed with GraphPadPrism4 (GraphPad Software Inc., La Jolla, Calif.) to calculate $IC_{50}$ values (nonlinear regression (curve fit), Dose-response—inhibition, 4 parameter logistic). The $IC_{50}$ value was considered as the concentration of inhibitor that reduced the absorbance at 450 nm by 50%, compared to a non-treated infected cell monolayer.

Compounds of the present invention can be tested in a hPIV-3 inhibition assay on well-differentiated human airway epithelal (HAE) cells using a published model. In brief the testing procedure is as follows: Human airway epithelial (HAE) cells are isolated, cultured and differentiated as previously described (Müller et al., 2013). Briefly, human nasal airway epithelial cells are isolated, expanded and seeded on collagen-coated permeable membrane supports. Once the cells are confluent, the apical medium is removed and cells are maintained at the air-liquid interface for approximately 4 to 6 weeks to allow epithelial differentiation. Cultures containing ciliated cells are inoculated via the luminal surface with 5000 focus forming units of hPIV-3 per well for 1 hour. Test compounds of formula (I), (II), (III) and (IIIa) at various concentrations are added to the basolateral medium just after the cells have been infected with the virus. Viral load reduction is assessed at 1, 3 and 6 days post-infection by virus titration using focus forming assay or in situ ELISA in A549 or LLC-MK2 cells, as previously published (Guillon et al., 2014). These results may be compared with a prior art reference compound such as a BCX compound including BCX-2855 to give an indication of relative potency (Guillon, P., Dirr, L., El-Deeb, I. M., Winger, M., Bailly, B., Haselhorst, T., Dyason, J. C., and von Itzstein, M. (2014). Structure-guided discovery of potent and dual-acting human parainfluenza virus haemagglutinin-neuraminidase inhibitors. Nat. Commun. 5; and Müller, L., Brighton, L. E., Carson, J. L., Fischer, W. A., and Jaspers, I. (2013). Culturing of Human Nasal Epithelial Cells at Air Liquid Interface. J. Vis. Exp.)

Results

A comparison of the potency of the synthesised C4 modified Neu5Ac2en derivatives against hPIV-3 HN was undertaken and, for convenience sake, the $IC_{50}$ values were divided into two groups based on the acylamino group present at C5. Group 1 inhibitors have a C5 acetamido functionality and Group 2 inhibitors have a C5 isobutyramido functionality (FIG. 3 and FIG. 4A-C). The benchmark and well-characterised broad spectrum neuraminidase inhibitor Neu5Ac2en (2) showed the weakest inhibition with $IC_{50}$ values of 1565 M and 1438 µM for hPIV-3 HN NI and HI, respectively. The inhibition observed for 3, the C5 acetamido analogue of BCX 2798 (6), was improved when compared to 2, although it was still in the high micromolar range with $IC_{50}$ values of 138 M and 210 µM for hPIV-3 HN NI and HI, respectively. These $IC_{50}$ values were similar to those observed for our novel inhibitor 7, a C4 methoxymethyl functionalised triazole Neu5Ac2en derivative, with experimentally determined hPIV-3 HN NI and HI $IC_{50}$ values of 154 μM and 313 μM, respectively. A significant improvement in potency was observed upon replacement of the C4 triazole's methoxymethyl moiety (7) with a bulkier phenyl group (8). $IC_{50}$ values of 6.5 μM and 4.6 μM were determined for hPIV-3 HN NI and HI for 8, respectively. The values are summarized in table 2.

Figure 2:
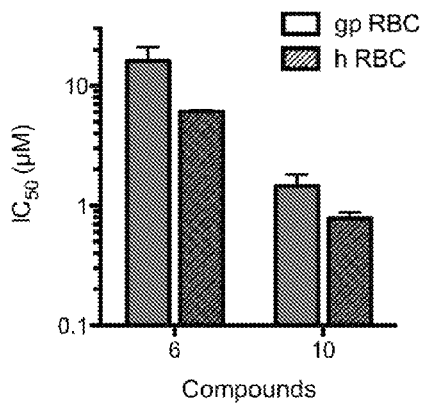
FIG. 2 is a comparison of HI $IC_{50}$ values for inhibitors 6 and 10, using guinea pig red blood cells (gp RBC, solid bar) and human red blood cells (h RBC, dashed bar)
Figure 3:
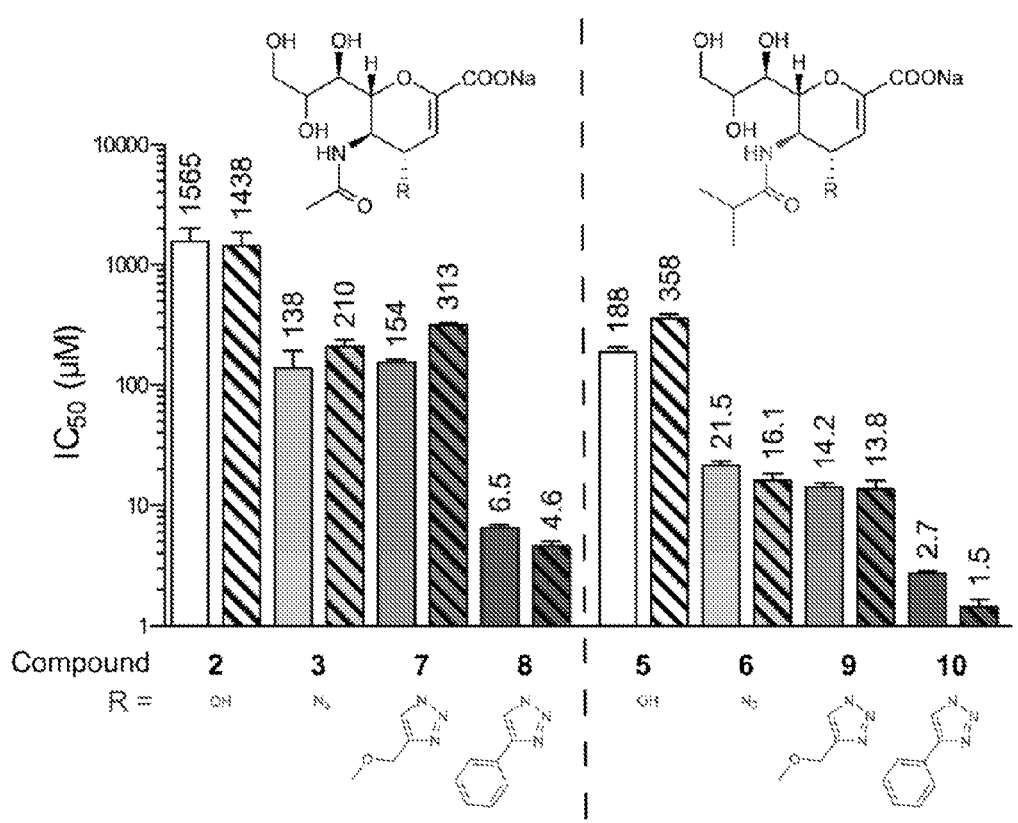
FIG. 3 is a graphical representation of NI (solid) and HI (dashed) $IC_{50}$ values for the Neu5Ac2en derivatives 2, 3, 5-10. Inhibitors 2, 3, 7, 8 with a C5 acetamido group (left panel, group 1) and inhibitors 5, 6, 9, 10 with a C5 isobutyramido group (right panel, group 2). Values are the means of determinations from 3 independent experiments and error bars correspond to calculated standard deviations.
Figure 4A:
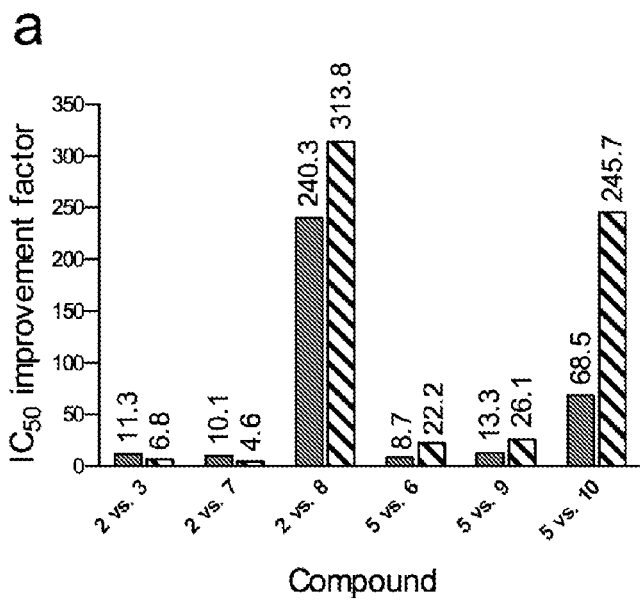
FIG. 4A-C is a graphical comparison of NI (solid bar) and HI (dashed bar) $IC_{50}$ values for selected inhibitors. (A) Comparison of NI and HI $IC_{50}$ values for compounds 3, 6-10 and their C-4 hydroxyl analogues (2 and 5). (B) Comparison of NI and HI $IC_{50}$ values for compounds 7-10 and their C-4 azido analogues (3 and 6). (C) Comparison of NI and HI $IC_{50}$ values for compounds 6, 9 and 10 and their C-5 acetamido analogues (3, 7 and 8 respectively)
Figure 4B:
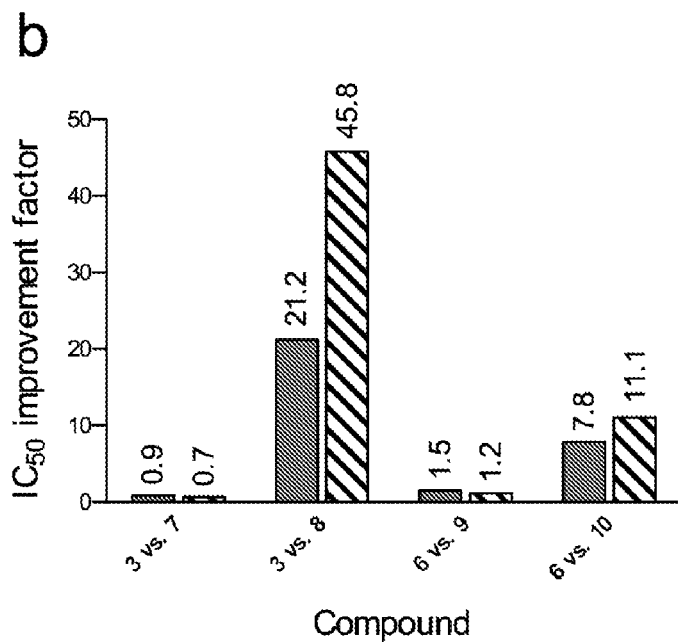
Figure 4C:
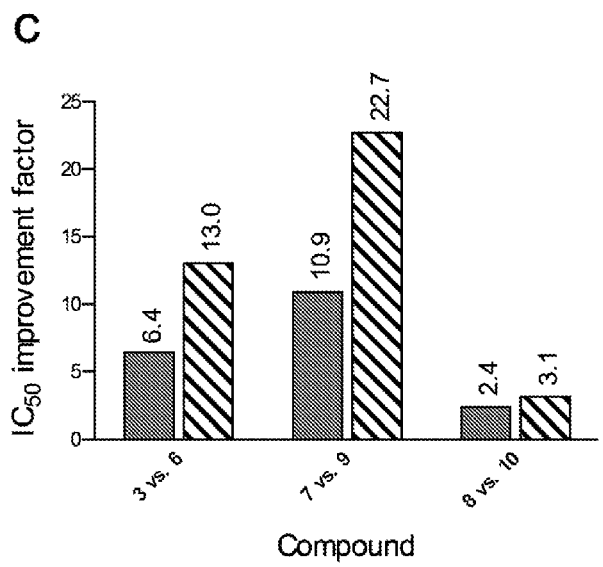

In the second group of inhibitors, that contain a C5 isobutyramido functionality, it was obvious that the affinity of each inhibitor was improved relative to its C5 acetamido analogue. The order of potency, not unexpectedly, was identical within the same group. Thus, the weakest inhibition was found for 5, the C5 isobutyramido analogue of Neu5Ac2en, with $IC_{50}$ values of 188 M and 358 M for NI and HI respectively and $IC_{50}$ values of 21.5 μM and 16.1 μM for NI and HI, respectively were determined for the reference hPIV inhibitor BCX 2798 (6). Inhibitor 9, with the relatively small methoxymethyl substituent on the triazole ring, had $IC_{50}$ values close to those determined for the C4 azido analogue 6 ($IC_{50}$=14.2 μM and 13.8 μM for NI and HI respectively). Similarly as observed in the C5 acetamido-containing Group 1 inhibitors, increasing the substituent size from the methoxymethyl group in inhibitor 9 to a bulkier phenyl moiety as in inhibitor 10, resulted in a remarkable improvement in potency with $IC_{50}$ values of 2.7 μM and 1.5 μM for NI and HI, respectively. Interestingly, an improvement in HI $IC_{50}$ values was observed when human red blood cells were used instead of guinea pig red blood cells (FIG. 2). This improvement most likely reflects sialic acid content and/or linkage presentation differences between human and guinea pig red blood cells. For example, it is well known that human tissues and cells, including red blood cells, only express N-acetylneuraminic acid-containing glycoconjugate receptors, whereas other animals also express N-glycolyl-neuraminic-acid-based receptors. Nevertheless, irrespective of the specific red blood cells used, our designer inhibitor 10 had significantly higher potency when compared to the benchmark compound 6. A $K_m$ value for MUN of 5.1 mM and $K_i$ values of 1.3 μM and 16 μM for inhibitor 10 and 6, respectively.

Cell-Based Assays

Figure 5A:
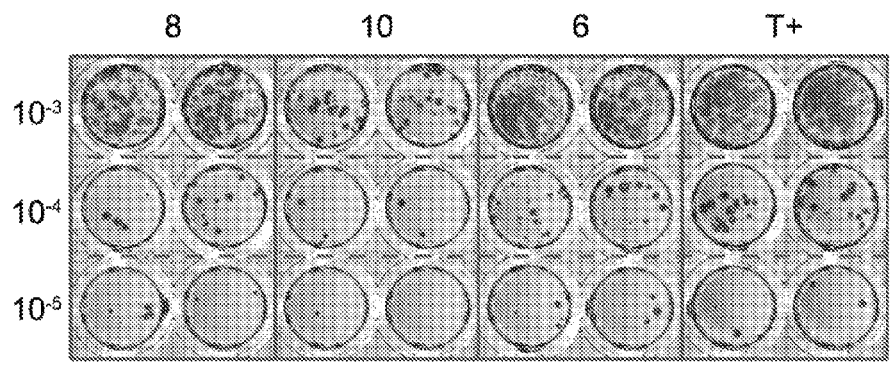
FIG. 5 is (a) Titration (focus forming assay) of progeny virus after a 48 h virus growth inhibition assay. Representative results of a progeny virus titration. Virus was harvested after 48 h amplification in the presence of 2 M of compounds 8, 10 or 6. Collected virus-culture supernatants were diluted at least 1:1000 to make sure the remaining compound has no effect on foci formation. (b) Virus growth inhibition of the reference inhibitor 6 and inhibitor 10. Virus growth inhibition was determined by titration of progeny from a low MOI infected confluent LLC-MK2 monolayer in the presence of 2 μM inhibitor. At this inhibitor concentration, 10 showed 94% inhibition compared with 14% inhibition for 6. These results are representative of 2 independent experiments performed in duplicate and error bars correspond to the calculated standard deviation.
Figure 5B:
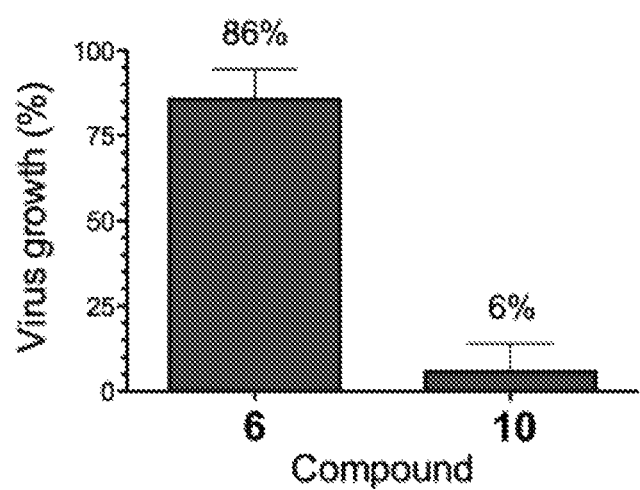
Figure 6:
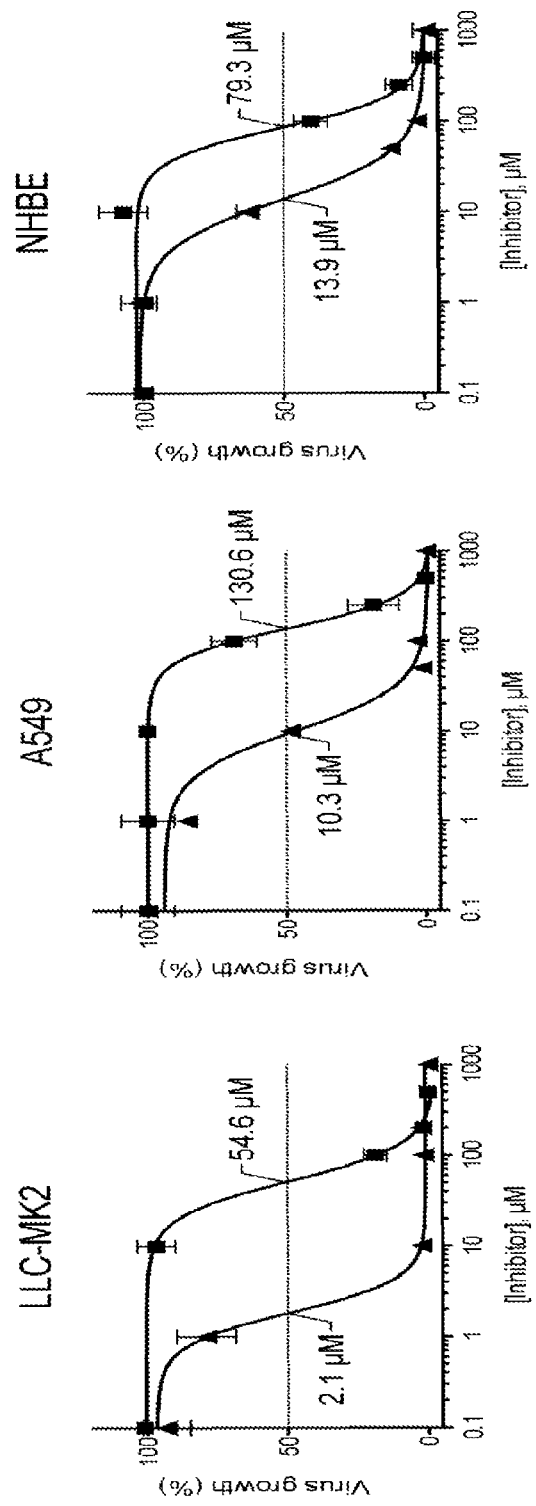
FIG. 6 shows Virus growth inhibition of the reference inhibitor 6 (□) and inhibitor 10 (▲) in various cell lines.

Following initial enzymatic screening, the most potent inhibitor 10 and the reference hPIV inhibitor (BCX 2798, 6) were then evaluated in a growth inhibition assay to compare their capacity to inhibit hPIV-3 virus infection and propagation in LLC-MK2 cells (FIGS. 5A and B). Compound 6 was chosen as a reference inhibitor as it is the most documented hPIV-3 Neu5Ac2en-based inhibitor to date and has reasonable in vitro hPIV-3 antiviral potency. In an initial assay, at an inhibitor concentration of 2 μM, the virus was propagated for 48 h in the presence of 6 or 10 and virus titres were determined. At this inhibitor concentration, a reduction of 14% and 94% in virus titre by 6 and 10 respectively was calculated (FIG. 5B). Virus growth inhibition $IC_{50}$ values were then determined for the two inhibitors in a well-established in situ ELISA technique using three different cell lines. The LLC-MK2 (monkey kidney epithelial cells) cell line was chosen as it is extensively used in hPIV-3 cell-based infection studies, as well as the hPIV-3 susceptible human respiratory cell lines A549 (lung adenocarcinoma epithelial cells) and normal human bronchial epithelial (NHBE) primary cells to investigate virus growth inhibition in natural tissue-related cells. The method itself has useful advantages over the virus titration method, as it is a faster, one-step, non-subjective technique that correlates non-immobilized virus growth to HN expression levels of a low multiplicity of infection (MOI) infected cell monolayer. Interestingly, slightly lower virus growth inhibition $IC_{50}$ values were determined for 10 and 6 with the laboratory established cell line LLC-MK2 in relation to the human cell lines. Overall, the same trend is observed for all three cell lines in that a significantly stronger antiviral effect of inhibitor 10 ($IC_{50}$=2.1-13.9 μM) is determined compared to inhibitor 6 ($IC_{50}$=54.6-130.6 μM) (FIG. 6).

Structural Biology

Sample Preparation and $^1$H NMR Experiments:

All NMR experiments were performed on a 600 MHz NMR spectrometer (Bruker) equipped with a 5-mm TXI probe with triple axis gradients. Intact virus suspension or recombinant hPIV-3 HN were buffer exchanged against 50 mM deuterated sodium acetate, 5 mM $CaCl_2$ in $D_2O$ at pD 4.6 by ultrafiltration using an Amicon Filter Unit (Millipore) with a cut-off value of 30 kDa or 10 kDa, respectively. For each experiment 20 μM hPIV-3 HN protein and a protein: ligand molar ratio of 1:100 in a final volume of 200 μL was used.

TABLE 2

NI and HI $IC_{50}$ values. Mean $IC_{50}$ values for each of the tested compounds with calculated standard deviation and standard error.

| Inhibitor | 2 | | 3 | | 7 | | 8 | |
|---|---|---|---|---|---|---|---|---|
| | NI | HI | NI | HI | NI | HI | NI | HI |
| Mean $IC_{50}$ | 1565 | 1438 | 138.1 | 210 | 154.4 | 312.5 | 6.512 | 4.583 |
| Std. deviation | 439.1 | 427 | 55.69 | 65.19 | 18.93 | 25 | 0.6305 | 0.7217 |
| Std. error | 219.6 | 213.5 | 21.05 | 29.15 | 8.467 | 12.5 | 0.364 | 0.4167 |

| Inhibitor | 5 | | 6 | | 9 | | 10 | |
|---|---|---|---|---|---|---|---|---|
| | NI | HI | NI | HI | NI | HI | NI | HI |
| Mean $IC_{50}$ | 187.7 | 358.3 | 21.46 | 16.12 | 14.16 | 13.75 | 2.74 | 1.458 |
| Std. deviation | 39.52 | 52.04 | 4.753 | 4.891 | 2.028 | 4.787 | 0.2319 | 0.3608 |
| Std. error | 19.76 | 30.05 | 1.797 | 2.187 | 1.171 | 2.394 | 0.1339 | 0.2083 |

¹H NMR spectra were acquired with 32 scans at 283 K, a 2 s relaxation delay over a spectral width of 6000 Hz. Due to the safer and easier handling of protein compared to virus and in order to provide exactly the same protein concentration in each experiment, the initial STD NMR experiment was carried out for compound 10 in complex with intact hPIV-3 virus, while all subsequent experiments were carried out using the recombinant HN protein.

Saturation Transfer Difference (STD) NMR Experiments:

The protein was saturated on-resonance at −1.0 ppm and off-resonance at 300 ppm with a cascade of 60 selective Gaussian-shaped pulses of 50 ms duration, resulting in a total saturation time of 3 s and the relaxation delay was set to 4 s. Each STD NMR experiment was acquired either with a total of 1056 scans (recombinant hPIV-3 HN) or 1512 scans (intact virus) and a WATERGATE sequence was used to suppress the residual HDO signal. A Spin-lock filter with 5 kHz strength and duration of 10 ms was applied to suppress protein background. Control STD NMR experiments were performed with an identical experimental setup and the same ligand concentration but in the absence of protein. On- and off-resonance spectra were stored and processed separately, and the final STD NMR spectra were obtained by subtracting the on-from the off-resonance spectra. All STD effects were quantified using the equation $A_{STD}=(I_0-I_{sat})/I_0=I_{STD}/I_0$. Therefore signal intensities of the STD NMR spectrum ($I_{STD}$) were compared to the corresponding signal intensities of a reference spectrum ($I_0$). The strongest STD signal in the spectrum was assigned to a value of 100% and used as a reference to calculate relative STD effects accordingly.

Saturation Transfer Difference (STD) NMR experiments of 8 in complex with recombinantly-expressed hPIV-3 HN (FIG. 7) and the most potent inhibitor 10 in complex with either recombinantly-expressed hPIV-3 HN (FIG. 8) or intact hPIV-3 virus (FIG. 9) were undertaken to further support the computational and biological studies that demonstrated specific binding and inhibition.

STD NMR signal intensities for all protons associated with 8 or 10 were clearly observed, to varying extents, when the inhibitor is in complex with either intact virus or recombinant hPIV-3 HN and clearly demonstrated that the ligand binds in both instances. The minor signals visible at 3.25, 3.5 and 4.0 ppm in the ¹H NMR spectrum of 10 acquired in the presence of intact virus particles were a consequence of impurities from the virus purification process and belong to neither the virus particles nor 10. As anticipated, none of these signals were observed in the STD NMR spectrum and clearly demonstrate that the impurities do not bind to the virus (FIG. 9). These experiments clearly demonstrate the specific binding of 10 to both intact hPIV-3 virus and hPIV-3 HN, further substantiating the inhibitor's biological relevance and potential.

Importantly, an overlay of the aromatic phenyl protons signals observed at 7.1-7.6 ppm in the STD NMR spectra for both the intact virus and recombinant HN protein also reveals that the binding epitope of inhibitor 10 is similar, if not identical, when bound either to intact hPIV-3 virus or to recombinant hPIV-3 HN protein (FIG. 10).

Epitope Mapping of Inhibitor 10

A complete ligand binding epitope was determined by the analysis of STD NMR spectra (FIG. 8) of hPIV-3 HN protein in complex with 10. All STD NMR signals of 10 were normalized to the strongest STD NMR signal observed, the inhibitor's H4′ proton at 7.18 ppm. Relative STD NMR effects for all protons of the inhibitor were then calculated (Table 2). The extent of the STD NMR signal intensity strongly depends on the proton's proximity to the protein surface and reveals how the designed inhibitor 10 engages the HN protein's binding site.

TABLE 3

Relative STD NMR effects[a] of 8 and 10 in complex with hPIV-3 HN.

| | Inhibitor 8 (%) | Inhibitor 10 (%) |
|---|---|---|
| Triazole CH | 63 | 75 |
| ArH2′ ArH6′ | 92 | 95 |
| ArH3′ ArH5′ | 100 | 100 |
| ArH4′ | 100 | 100 |
| H3 | 85 | 80 |
| H4 | 59 | 59 |
| H5 | 50 | 49 |
| H6 | 49 | 47 |
| H7 | 30 | 36 |
| H8 | 30 | 35 |
| H9 | 12 | 24 |
| H9′ | 18 | 21 |
| Isoprop-CH | — | 54 |
| Isoprop-2CH₃ | — | 42 |
| NHAc | 41 | — |

[a]STD effects calculated according to the formula $A_{STD} = (I_0 - I_{sat})/I_0 = I_{STD}/I_0$. All STD NMR effects are given relative to the strongest STD NMR intensity of the C4 triazolo ArH4′.

Notably, very strong relative STD NMR effects were observed for the phenyl group protons H2′, H3′, H4′, H5′ and H6′ between 7.1 ppm and 7.6 ppm revealing a close contact in that region of the molecule to the protein surface. Moreover, a significant STD NMR effect was likewise detected for the CH of the triazole moiety. In contrast, the C5 isobutyramido moiety's protons of the inhibitor showed less effect (relative STD NMR signal intensities in the range of 42-54%).

The protons associated with the Neu5Ac2en core structure of 10 displayed variable relative STD NMR effects. A significant H3 relative STD NMR signal intensity (80%) suggests a strong interaction of this part of the molecule with hPIV-3 HN. Furthermore, relative STD NMR signal intensities for H4, H5 and H6 of 59%, 50% and 49%, respectively, demonstrate that the ring protons of the Neu5Ac2en core structure are also involved in inhibitor engagement to the protein.

Finally, weaker relative STD NMR effects of 36%, 35%, 24% and 21%, were observed for the glycerol side chain protons H7, H8, H9 and H9′, respectively and suggest that the glycerol sidechain makes less of a contribution to the inhibitor binding event compared with the C4 triazolo functionality and the inhibitor's core ring structure (FIG. 8). The inhibitor 8 epitope map (FIG. 7) was for all intents and purposes identical to that of inhibitor 10, with the C4 triazolo moiety clearly in close contact to the protein surface.

Difluoro Analogues

The compounds may include diflouronated compounds and testing has been performed on select members of this class (I-170, I-179 and I-104 shown below). The target of such compounds is the haemagglutinin-neuraminidase of hPIV-3 and hPIV-1. A co-crystal structure of hPIV-3 HN in complex with 1-170 has been obtained. All of the below compounds have been tested in (i) NI enzymatic assays against hPIV-3 (and 170 also against hPIV-1); (ii) cell based assays with the human cell line A549 cells (adenocarcinomic human alveolar basal epithelial cells) have been evaluated using hPIV-3; (iii) cell cytotoxicity tests of the compounds against A549 cells; and (iv) NI enzymatic assays against the human Neuraminidase 2 showed no activity. No cell cytotoxicity was observed for any of the compounds at 150 µM using A549 cells as shown in FIG. 11. No activity was observed against human Neu2 as indicated in FIG. 12.

TABLE 4

Enzymatic and cell-based assays for select difluorinated compounds with I-57 and I-40 as the corresponding non-fluorinated 'en' compounds for comparison.

I-170

I-179

I-104

| µM | 6 | I-70 | I-57 | I-79 | I-40 | I-104 |
|---|---|---|---|---|---|---|
| NI hPIV-3 $IC_{50}$ | 18 | 6 | 2.5 | 63 | 12 | 4 |
| Cell-based ELISA $IC_{50}$ | 130 | 14 | 10 | 45 | 80 | 25 |

Influenza Virus Sialidase Activity Assay

In a standard 96-well plate format, by use of sialidase from Influenza A and B, the synthesized compounds can be assayed for their capacity to inhibit influenza virus sialidase by a modification (Biochim. Biophys. Acta 1991, 10, 65-71) of the fluorometric method of Potier et al. (Anal. Bio-chem. 1979, 94, 287-296) using the fluorogenic substrate 4-methylumbelliferyl N-acetyl-α-D-neuraminide (MUN). All inhibition assays can be done in triplicate over six inhibitor concentrations and at with 0.1 mM MUN. Specifically, 7 µL of 50 mM sodium acetate-6 mM CaCl2 buffer (pH 5.5) is added to each well of a 96-well solid black plate on ice, followed by 1 µL of inhibitor, 1 µL of sialidase, and finally 1 µL of the substrate MUN. The plate is then briefly centrifuged up to 1000 rpm for approximately 10 s to combine all components, and the mixture can be incubated at 37° C. with 900 rpm shaking for 20 min. To stop the reaction, 250 µL of 0.25 M glycine, pH 10, may be added to each well, and the fluorescence read (1 s per well) at an excitation of 355 nm and emission of 460 nm with a Victor 3 multilabel reader (PerkinElmer, Waltham, Mass.). Data can be processed by background subtraction (negative control RF) and then analysed with GraphPadPrism 4 (GraphPad Software Inc., La Jolla, Calif.) to calculate $IC_{50}$ values (nonlinear regression (curve fit), Dose-response—inhibition, 3 parameter logistic).

In Situ Cellular ELISA for Influenza A and B

To evaluate virus growth inhibition of Influenza A and Influenza B virus for the synthesised compounds, MDCK cells will be infected with influenza A or Influenza B virus in an in situ cellular ELISA developed based on the principles described by Berkowitz and Levin, 1985 (Antimicrob. Agents Chemother, 28, 207-210) and adapted to IAV by Myc et al, 1999 (J. Virol. Methods 77, 165-177 (1999)). MDCK cells in 100 µl Eagle's Minimum Essential Medium (EMEM) supplemented with 2 mM glutamine and 10% FBS are seeded on flat-bottom 96-well microtiter plates and incubated overnight. On the next day, the culture medium is removed and cells washed with medium. A total of 50 µl of viral inoculum (40 FFU/well) are added to the wells and incubated at 37° C., 5% $CO_2$ for 1 h with gentle agitation every 15 minutes. The viral inoculum is then removed and replaced with 100 µl of infection medium (EMEM supplemented with 2 mM glutamine and 3.0 µg/ml of TPCK treated trypsin). Infected MDCK cells are incubated for an additional 12-20 h, as necessary, and medium will be aspirated. The cells can be fixed with 3.7% paraformaldehyde in PBS. On the day of assay, fixed cells are washed and endogenous peroxidases inactivated with 0.35% H2 O2/PBS for 30 minutes at 37° C. The wells are washed again and incubated with 50 µl of 1.5 mg/ml of mouse monoclonal anti-influenza A or anti-influenza B Haemagglutinin and incubated for 45 min at 37° C. The cells are washed four times with washing buffer (PBS and 0.02% Tween-20), and incubated with 50 µl of 1:2000 dilution of goat anti-mouse IgG (H+L) HRP conjugated (BioRad, ref. 170-6516) for 45 min at 37° C. Plates are washed as previously with washing buffer and 100 µl of BD OptEIATMB substrate (BD Biosciences, San Jose, Calif.) added to each well then the plate can be incubated at 37° C.

The enzymatic reaction can be stopped after 3-5 min by the addition of 50 µL of 1 M of H2SO4 per well. Raw data is obtained by reading the absorbance (OD) of each well at 450 nm for 0.1 sec with a Victor 3 multilabel reader (PerkinElmer, Waltham, Mass.). Final ODs are obtained by subtraction of the negative control (non-infected cells) OD from the initial OD reading and the data analysed with GraphPadPrism4 (GraphPad Software Inc., La Jolla, Calif.) to calculate IC50 values (nonlinear regression (curve fit), Dose-response—inhibition, 4 parameter logistic). The $IC_{50}$ value is considered as the concentration of inhibitor that reduced the absorbance at 450 nm by 50%, compared to a non-treated infected cell monolayer.

The in situ cell based ELISA can be performed as for hPIV-3 with minor modifications including differences between hPIV-1 and 3 tests such as: Primary antibody: Mouse monoclonal anti-hPIV-3 HN (Fitzgerald, clone M02122321); Mouse monoclonal anti-hPIV-1 HN (LSbio, ref LS-C74109); hPIV-3 infection media: EMEM+2 mM glutamine; hPIV-1 infection media: EMEM+2 mM glutamine+TrypLE select 1.2%.

hPIV-3 NI and hPIV-1 NI IC50 Values for Compounds of the Invention

IC50 values for a number of compounds of the first aspect were determined by standard assay methods previously described in Guillon, P et al, Nature Communications (2014). In the below tables are IC50 values for prepared compounds wherein the chemistry ID aligns with those references and compound structures provided in the experimental characterisation section.

TABLE 5 hPIV-3 and hPIV-1 IC50 values for tested compounds

| Chemistry ID | IC50 (µM) |
|---|---|
| hPIV-3 NI (IC50 values) | |
| IE1172-78 | 2.47 |
| IE1172-82 | 3.95 |
| IE1172-83 | 5.61 |
| IE1172-87 | 77.35 |
| IE1172-45 | 315 |
| IE1172-102 | >1000 |
| IE1257-84 | 2.19 |
| IE1398-33 | 1.97 |
| IE832-8 | 54.43 |
| IE832-12 | 51.85 |
| IE832-17 | 148.5 |
| IE832-20 | 6.28 |
| IE832-26 | 67.67 |
| IE832-27 | 106.1 |
| IE832-31 | 22.92 |
| IE832-37 | 2.4 |
| IE889-34 | 3.23 |
| IE889-52 | 5.85 |
| IE927-60 | 13.13 |
| IE927-67 | 114.3 |
| IE984-5 | 1.38 |
| IE1257-24 | 8.49 |
| IE889-80 | 2.68 |
| IE889-99 | 0.599 |
| IE927-99 | 0.268 |
| IE832-98 | 27.38 |
| IE889-42 | 5.11 |
| hPIV-1 NI (IC50 values) | |
| IE1172-78 | 75.15 |
| IE1172-82 | 57.18 |
| IE1172-83 | 73.62 |
| IE1172-87 | 92.79 |
| IE1172-45 | >1000 |
| IE1172-102 | 793.4 |
| IE1257-84 | 24.88 |
| IE1398-33 | no data |
| IE832-8 | 300.6 |
| IE832-12 | 215.3 |
| IE832-17 | 19.82 |
| IE832-20 | 192.7 |
| IE832-26 | 95.49 |
| IE832-27 | 301.9 |
| IE832-31 | 303.5 |
| IE832-37 | 200.6 |
| IE889-34 | 30.3 |
| IE889-52 | 168.5 |
| IE927-60 | 0.489 |
| IE927-67 | 47.74 |
| IE984-5 | 21.88 |
| IE1257-24 | 0.36 |
| IE889-80 | 16.9 |
| IE889-99 | 6.22 |
| IE927-99 | 3.09 |
| IE832-98 | 7.44 |
| IE889-42 | 0.159 |

The invention claimed is:

1. A compound of formula (I), or a pharmaceutically acceptable salt thereof:

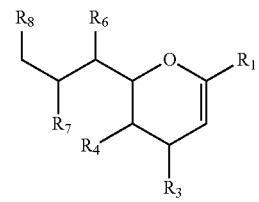

Formula (I)

wherein, $R_1$ is selected from the group consisting of COOH, or a salt thereof, $C(O)NR_9R_{10}$, $C(O)OR_{11}$ wherein $R_9$, $R_{10}$ and $R_{11}$ are independently selected from the group consisting of hydrogen and optionally substituted $C_1$-$C_6$ alkyl;

$R_3$ is selected from the group consisting of optionally substituted N-linked tetrazole, optionally substituted N-linked indole, optionally substituted N-linked isoindole, optionally substituted N-linked benzotriazole, and N-linked triazole substituted at one or both ring carbon atoms having the below structure:

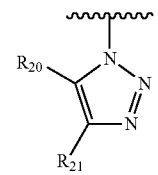

wherein, $R_{20}$ and $R_{21}$ are selected from the group consisting of hydrogen, hydroxyl, cyano, halo, $C_1$-$C_6$ alkyl, $C_1$-$C_6$ haloalkyl, $C_1$-$C_6$ alkylether, optionally substituted pyridyl and optionally substituted phenyl, with the proviso that when $R_{20}$ is hydrogen and $R_4$ is AcHN then $R_{21}$ is selected from the group consisting of hydrogen, hydroxyl, cyano, halo, $C_1$-$C_6$ alkyl, $C_1$-$C_6$ haloalkyl, $C_1$-$C_6$ alkylether, substituted pyridyl and substituted phenyl wherein substitution of pyridyl and phenyl is independently with a moiety selected from the group consisting of methyl, propyl, isopropyl, n-butyl, sec-butyl, isobutyl, tert-butyl, pentyl, isoamyl, 2-methylbutyl, 3-methylbutyl, hexyl, $C_1$-$C_6$ haloalkyl, $C_1$-$C_6$ alkylhydroxy, $C_1$-$C_2$ alkoxy, carboxy and salts thereof, $C_4$-$C_6$ alkoxy, Cl, Br, I, and —$CH_2OCH_3$;

and wherein at least one of $R_{20}$ and $R_{21}$ is not hydrogen;

$R_4$ is $NHC(O)R_{17}$ wherein $R_{17}$ is selected from the group consisting of $C_1$-$C_6$ alkyl, $C_1$-$C_6$ haloalkyl and $C_3$-$C_6$ cycloalkyl;

$R_6$, $R_7$ and $R_8$ are independently selected from the group consisting of OH, $NH_2$, $C_1$-$C_6$ alkyl, $NR_{18}R_{18}'$, $C_1$-$C_6$ alkoxy, —$OC(O)R_{18}$, —$NH(C=O)R_{18}$, and $S(O)_nR_{18}$, wherein n=0-2 and each $R_{18}$ and $R_{18}'$ are independently hydrogen or optionally substituted $C_1$-$C_6$ alkyl, and with the proviso that when $R_4$ is NHAc and $R_3$ is a triazole substituted only at the $R_{21}$ position then the triazole is not substituted with propyl, substituted propyl, substituted tert-butyl or diethoxyalkyl.

2. The compound of claim 1 wherein $R_1$ is COOH, or a salt thereof, or $C(O)OR_{11}$ wherein $R_{11}$ is selected from methyl, ethyl and propyl.

3. The compound of claim 1 wherein $R_3$ is selected from the group consisting of:

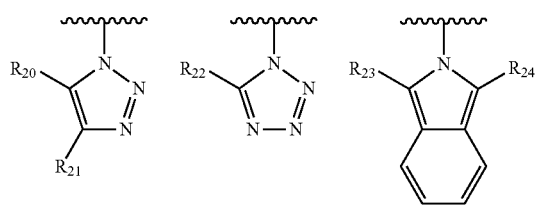

wherein, $R_{20}$ and $R_{21}$ as defined in claim 1;
$R_{22}$ is selected from the group consisting of hydrogen, $C_1$-$C_6$ alkyl and optionally substituted phenyl; and
$R_{23}$ and $R_{24}$ are independently selected from the group consisting of hydrogen, hydroxyl, cyano, halo, $C_1$-$C_6$ alkyl and $C_1$-$C_6$ haloalkyl.

4. The compound of claim 3 wherein when $R_{22}$ is optionally substituted phenyl then the substitution may be with a moiety selected from the group consisting of $C_1$-$C_6$ alkyl, $C_1$-$C_6$ haloalkyl, $C_1$-$C_6$ alkylhydroxy, $C_1$-$C_6$ alkoxy, halo, —C(O)OMe and —CH$_2$OCH$_3$.

5. The compound of claim 1 wherein $R_3$ is selected from the group consisting of:

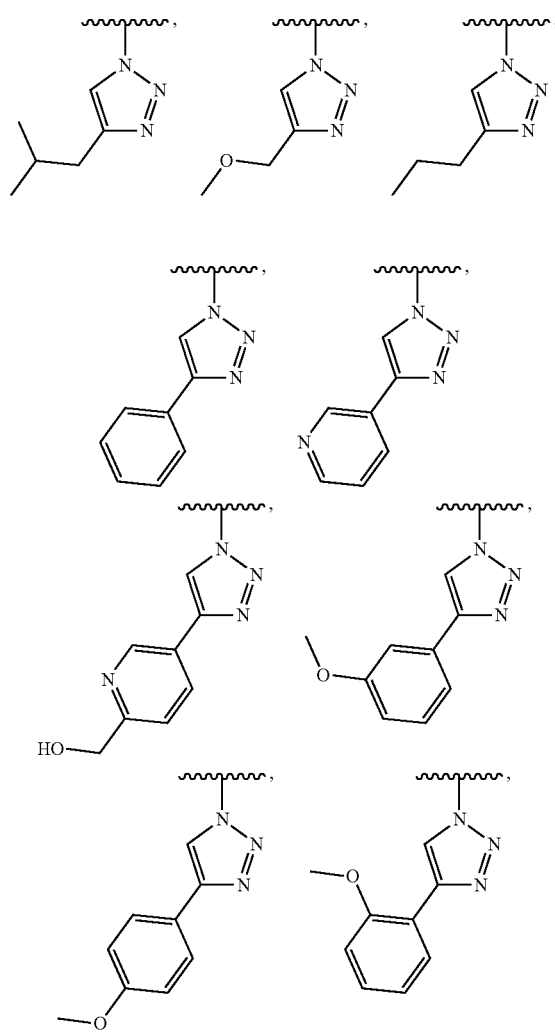

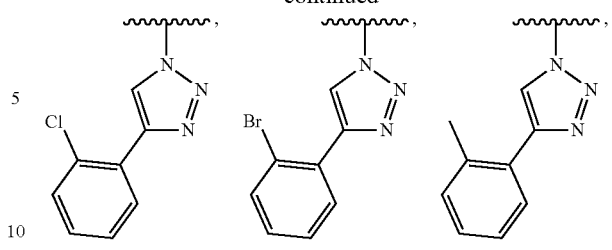

-continued

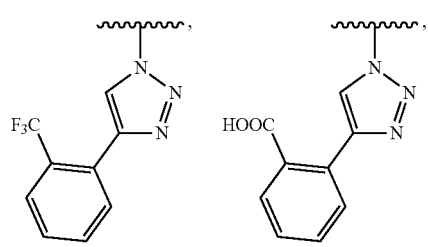

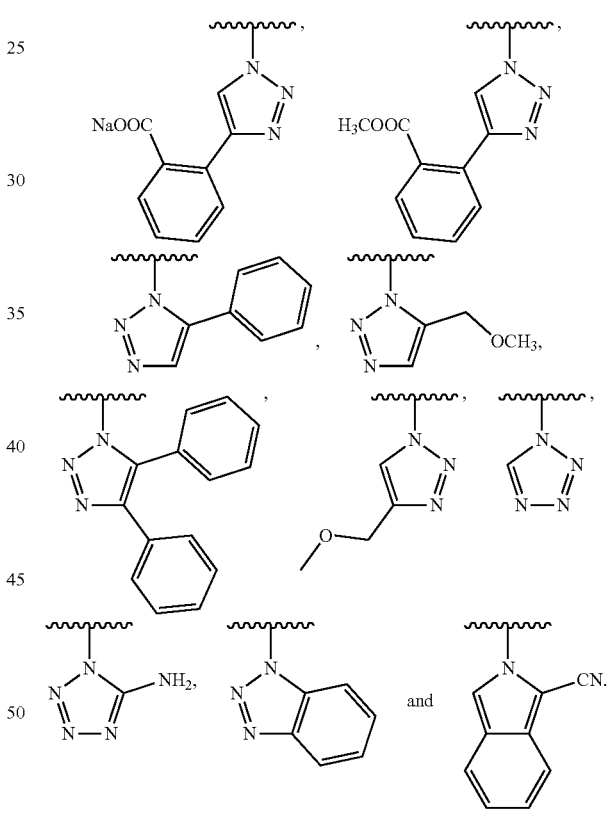

6. The compound of claim 1 wherein $R_4$ is selected from the group consisting of:

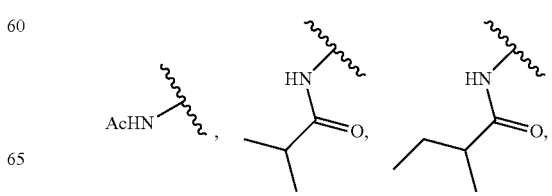

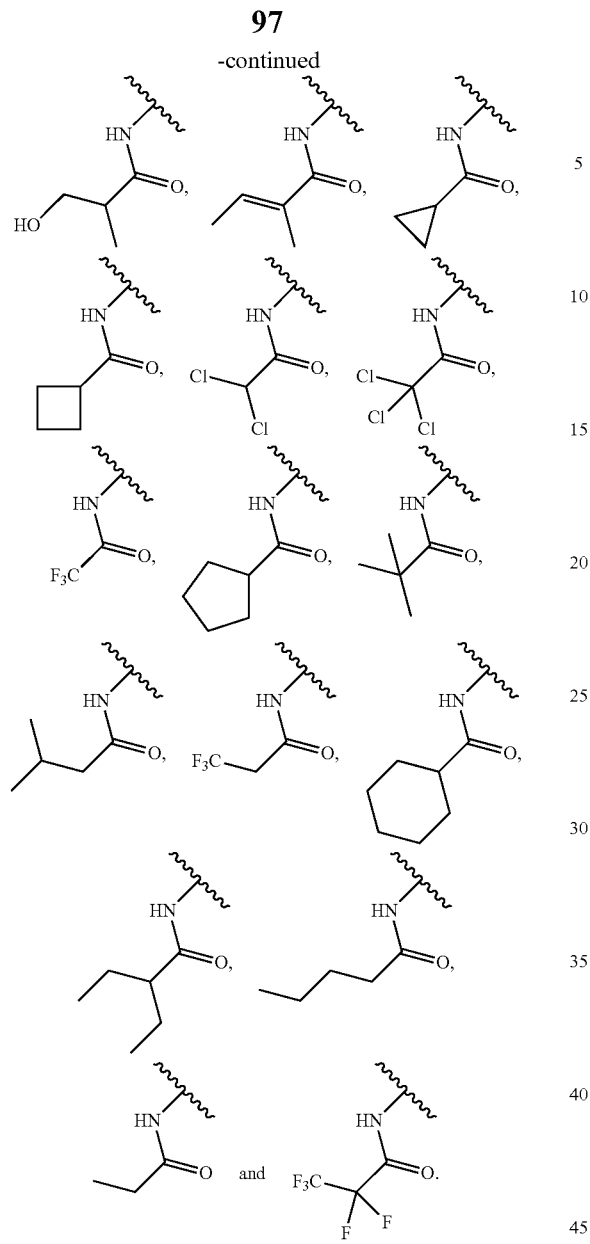

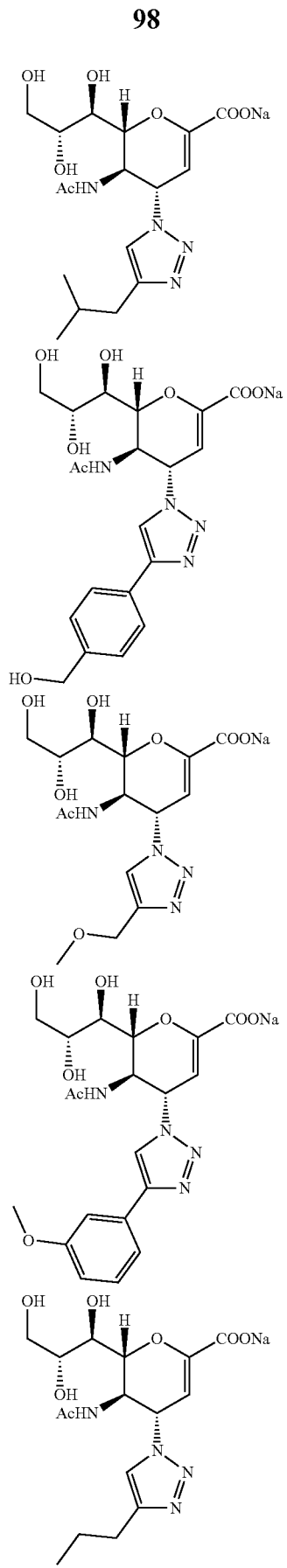

7. The compound of claim 1 wherein $R_4$ is selected from the group consisting of —NHAc, —NHC(O)CH$_2$(CH$_3$)$_2$, —NHC(O)CF$_3$ and —NHC(O)CH$_2$CH$_3$.

8. The compound of claim 1 wherein $R_6$, $R_7$ and $R_8$ are independently selected from OH and OAc.

9. The compound of claim 1 wherein the compound of formula (I) is a compound of formula (II):

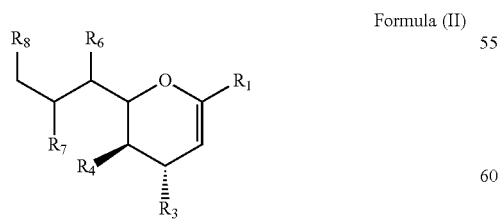

Formula (II)

wherein, $R_1$, $R_3$, $R_4$, $R_6$, $R_7$ and $R_8$ are as described in any one of the preceding claims.

10. The compound of claim 1 wherein the compound of formula (I) is a compound selected from the group consisting of:

99
-continued
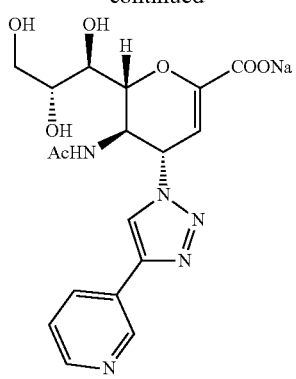
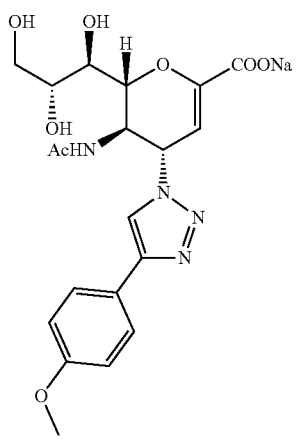
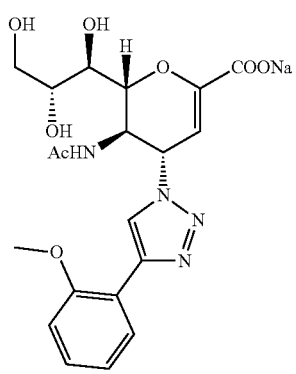
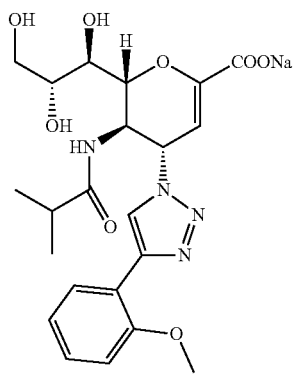
100
-continued
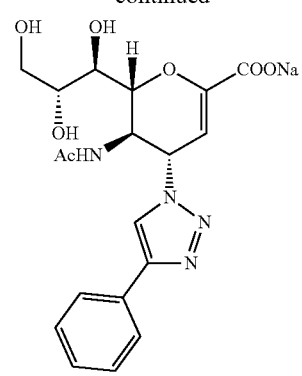
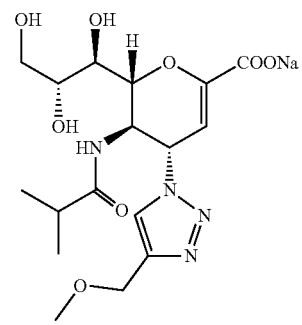
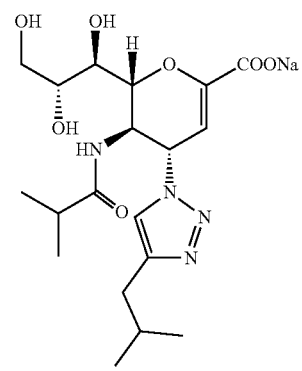
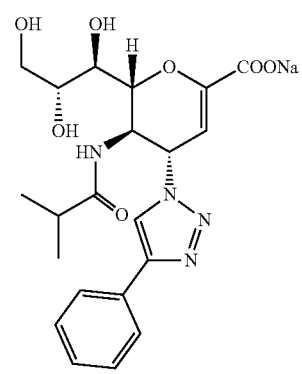

-continued
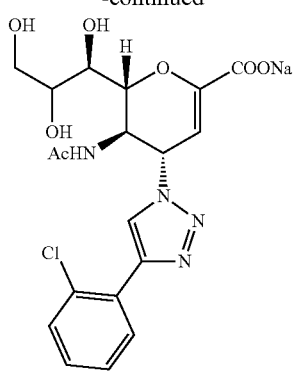
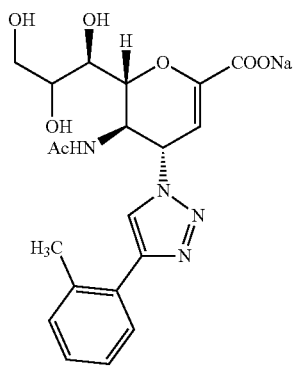
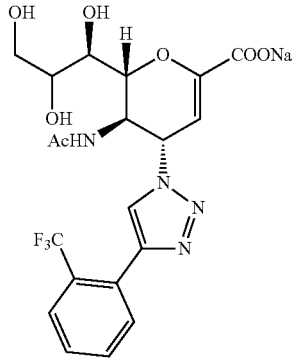
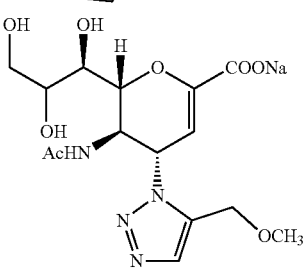
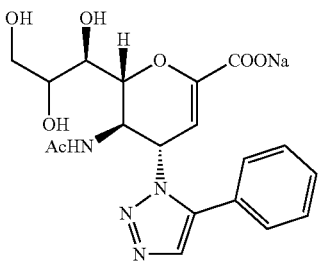
-continued
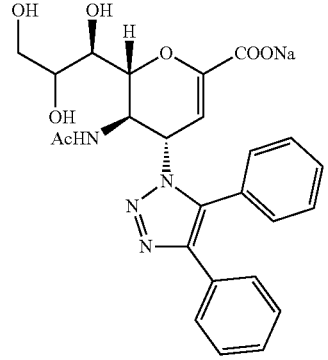
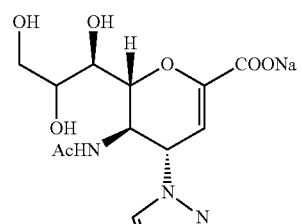
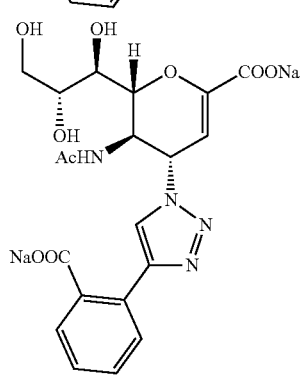
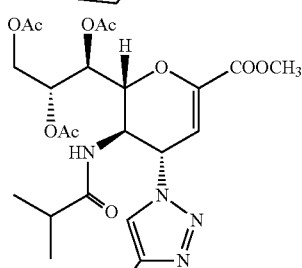
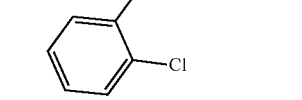
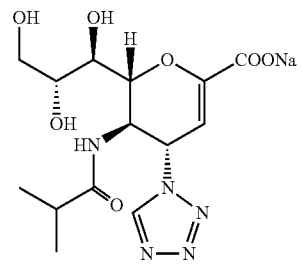

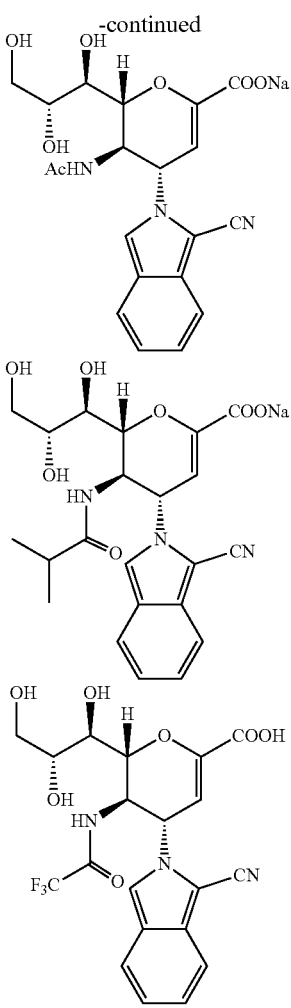

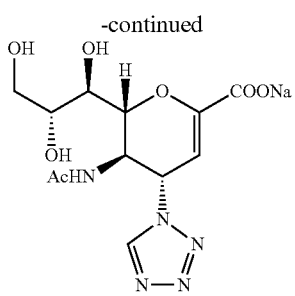

and analogues thereof wherein the C-2 carboxy group is in the protonated form, sodium salt form or $C_1$-$C_3$ ester prodrug form and wherein the $R_4$ position is substituted with any —NHC(O)R group wherein R is $C_1$-$C_4$ alkyl or haloalkyl.

11. A pharmaceutical composition comprising an effective amount of a compound of claim 1, or a pharmaceutically acceptable salt thereof, and a pharmaceutically acceptable carrier, diluent and/or excipient.

12. A method of treating a disease, disorder or condition caused by parainfluenza virus in a patient including the step of administering an effective amount of a compound of claim 1 to the patient.

13. The method of claim 12 wherein the parainfluenza virus is selected from the group consisting of the hPIV-1, 2 and 3 virus.

14. The method of claim 12 wherein the patient is a domestic or livestock animal or a human.

15. A method of inhibiting the activity of a parainfluenza viral haemagglutinin and/or neuraminidase enzyme by contacting the enzyme with a compound of claim 1, or a pharmaceutically effective salt thereof.

* * * * *